US012066432B2

(12) United States Patent
Frye et al.

(10) Patent No.: US 12,066,432 B2
(45) Date of Patent: Aug. 20, 2024

(54) PLACENTAL PROTEIN BIOMARKERS FOR GESTATIONAL AGE ASSESSMENT AND RELATED METHODS

(71) Applicant: Gynuity Health Projects, Inc., New York, NY (US)

(72) Inventors: Laura Frye, New York, NY (US); Elizabeth Raymond, New York, NY (US); Beverly Winikoff, New York, NY (US)

(73) Assignee: Gynuity Health Projects, Inc., New York, NY (US)

( * ) Notice: Subject to any disclaimer, the term of this patent is extended or adjusted under 35 U.S.C. 154(b) by 529 days.

(21) Appl. No.: 16/893,377

(22) Filed: Jun. 4, 2020

(65) Prior Publication Data
US 2020/0386745 A1    Dec. 10, 2020

Related U.S. Application Data

(60) Provisional application No. 62/857,746, filed on Jun. 5, 2019.

(51) Int. Cl.
*G01N 33/53* (2006.01)
(52) U.S. Cl.
CPC ......... *G01N 33/53* (2013.01); *G01N 33/5302* (2013.01); *G01N 2800/368* (2013.01); *G01N 2800/385* (2013.01)
(58) Field of Classification Search
None
See application file for complete search history.

(56) References Cited

U.S. PATENT DOCUMENTS

| | | | |
|---|---|---|---|
| 4,123,509 A | 10/1978 | Banik et al. | |
| 4,191,533 A | 3/1980 | Bohn et al. | |
| 5,641,870 A | 6/1997 | Rinderknecht et al. | |
| 8,491,850 B2 | 7/2013 | Baugh et al. | |
| 8,721,990 B2 | 5/2014 | Raj et al. | |
| 10,392,665 B2 | 8/2019 | Boniface et al. | |
| 10,591,480 B2 | 3/2020 | Heinz et al. | |
| 10,802,022 B1 | 10/2020 | Bradshaw et al. | |
| 2008/0131317 A1 | 6/2008 | Davis et al. | |
| 2010/0304978 A1 | 12/2010 | Deng et al. | |
| 2014/0273028 A1 | 9/2014 | Menon-Johansson | |
| 2016/0223536 A1 | 8/2016 | Johnson et al. | |
| 2019/0390272 A1 | 12/2019 | Ortogero et al. | |
| 2020/0386745 A1 | 12/2020 | Frye et al. | |

FOREIGN PATENT DOCUMENTS

| | | |
|---|---|---|
| CN | 103 235 142 | 8/2013 |
| EP | 2356464 | 4/2015 |
| WO | WO-1994/021686 | 3/1994 |
| WO | WO 2006/100415 | 9/2006 |
| WO | WO-2009/097579 | 8/2009 |
| WO | WO-2010/055355 | 5/2010 |
| WO | WO-2010/085815 | 7/2010 |
| WO | WO 2022/125710 | 6/2022 |

OTHER PUBLICATIONS

Veenstra et al., Oncogenesis (2018)7:87 (Year: 2018).*
Heeschen et al., J Am Coll Cardiol 2005;45:229-37 (Year: 2005).*
Letter to Editor by Johnson et al., The Journal of Applied Laboratory Medicine, vol. 7, Jul. 2022; 1000-1002; https://doi.org/10.1093/jalm/jfac020 (Year: 2022).*
Dumps et al., European Journal of Obstetrics & Gynecology and Reproductive Biology 100 (2002) 174-180 (Year: 2002).*
2012 American Association For Clinical Chemistry, "Development of a fully characterized picoPAPP-A chemiluminescence assay for male and female serum evaluation".
2012 American Association For Clinical Chemistry, "Development of a well characterized PAPP-A2 chemiluminescence assay to measure PAPP-A2 in maternal biological fluids".
2012 Endocrine Society Meeting, "Development of a well characterized PAPP-A2 ELISA to measure PAPP-A2 in maternal biological fluids".
2012 Endocrine Society Meeting, "Development of a well characterized Total PAPP-A chemiluminescent assay for maternal serum evaluation".
Ahmed et al. Estimation of gestational age by last menstrual period, by ultrasound scan and by SP1 concentration: comparisons with date of delivery. Br J Obstet Gynaecol. Feb. 1986;93(2):122-7.
Armbruster et al., "Limit of blank, limit of detection and limit of quantitation," Clin Biochem Rev. Aug. 2008;29 Suppl 1 (Suppl 1):S49-52. PubMed PMID: 18852857; PMCID: PMC2556583.
Bale et al., "Inducible reduction in pregnancy-associated plasma protein-A gene expression inhibits established atherosclerotic plaque progression in mice," Endocrinology, Apr. 2014; 155(4):1184-1187.
Bayes-Genis et al., Pregnancy-associated plasma protein A as a marker of acute coronary syndromes. N Engl J Med. (2001) 345: 1022-1029.
Bersinger et al., "Production and characterization of monoclonal antibodies against pregnancy-associated plasma protein A," Mol Hum Reprod. Jul. 1999;5(7):675-81. PubMed PMID: 10381824.
Bischof et al. Pregnancy-associated plasma protein-A (PAPP-A) and hCG in early pregnancy. Br J Obstet Gynaecol. Oct. 1981;88(10):973-5.
Bischof et al. Amniotic fluid and plasma concentrations of pregnancy-associated plasma protein-A (PAPP-A) throughout pregnancy: comparison with other fetoplacental products. Br J Obstet Gynaecol. May 1982;89(5):358-63. PubMed PMID: 6177337.
Bischof et al. Relationship of obstetric parameters to the concentration of pregnancy-associated plasma protein A. Am J Obstet Gynecol 1980;138:494-9.
Bonno et al. "Localization of pregnancy-associated plasma protein-A and co localization of pregnancy associated plasma protein-A messenger ribonucleic acid and eosinophil granule major basic protein messenger ribonucleic acid in placenta." Lab Invest. Oct. 1994;71(4):560-6. PubMed PMID: 7526035.

(Continued)

*Primary Examiner* — Christina M Borgeest
(74) *Attorney, Agent, or Firm* — MORRISON & FOERSTER LLP

(57) ABSTRACT

Provided herein are methods, systems and kits for detection of certain placental proteins, such as PAPP-A and ADAM-12, for example, in a serum sample from an individual to classify gestational ages above and below a specific threshold, such as for use in determining for use in determining gestational age for making clinical or personal decisions without ultrasound.

8 Claims, 8 Drawing Sheets

(56) References Cited

OTHER PUBLICATIONS

Braunstein et al. Serum human chorionic gonadotropin levels throughout normal pregnancy. Am J Obstet Gynecol. Nov. 15, 1976;126(6):678-81.

Bretthauer et al. "Effect of Colonoscopy Screening on Risks of Colorectal Cancer and Related Death." *New England Journal of Medicine* (2022).

Buhimschi et al. Analytical Comparison of Pregnancy-Associated Plasma Protein-A (PAPP-A) Immunoassays for Biochemical Determination of Gestational Age. J Appl Lab Med. 2021;6(6):1517-32.

Bulut et al., "Relationship between Pregnancy associated plasma protein A and lung cancer," Am J Med Sci. Apr. 2009; 337 (4): 241-244.

Byrnes et al., "Selecting analytical biomarkers for diagnostic applications: a first principles approach," Expert Rev Mol Diagn. 2018;18(1):19-26.

Christiansen et al. Human placental lactogen is a first-trimester maternal serum marker of Down syndrome. Prenat Diagn 2007;27:1-5.

Clifton et al., "Pregnancy-associated plasma protein-A modulates the anabolic effects of parathyroid hormone in mouse bone," Bone. Dec. 2015; 81:413-6.

Committee on Obstetric Practice, the American Institute of Ultrasound in Medicine, and the Society for Maternal-Fetal Medicine. Committee Opinion No. 700: Methods for Estimating the Due Date. Obstet Gynecol 2017;129(5):e150-4.

Conover et al., "Preferential impact of pregnancy-associated plasma protein-A deficiency on visceral fat in mice on high-fat diet," Am J Physiol Endocrinol Metab. Nov. 2013; 305(9):E1145-53.

Coskun et al., "Pregnancy-associated plasma protein A and asthma," Adv Ther. 2007; 24: 362-367.

Coskun et al. Pregnancy-associated plasma protein A: evaluation of a new biomarker in renal transplanted patients. Transplant Proc. 2007; 39:3072-3076.

Creinin et al., Committee on Practice Bulletins—Gynecology; Society of Family Planning. Medication Abortion Up to 70 Days of Gestation: ACOG Practice Bulletin, No. 225. Obstet Gynecol 2020;136(4):e31-47.

Deeks et al., "Diagnostic tests 4: likelihood ratios," BMJ. 2004;329(7458):168-169. doi:10.1136/bmj.329.7458.168.

Delong et al. "Comparing the areas under two or more correlated receiver operating characteristic curves: a nonparametric approach." (1998) Biometrics 44:837-845.

Dominitz. "Understanding the Results of a Randomized Trial of Screening Colonoscopy." *New England Journal of Medicine* (2022).

Doran et al., "Barriers and facilitators of access to first-trimester abortion services for women in the developed world: a systematic review," J Fam Plann Reprod Health Care. Jul. 2015 ;41(3):170-80. PubMed PMID: 26106103.

Ferguson et al. "Systematic Review of the Effectiveness, Safety, and Acceptability of Mifepristone and Misoprostol for Medical Abortion in Low- and Middle-Income Countries." *J Obstet Gynaecol Can JOGC J Obstet Gynecol Can JOGC*. 2020;42(12):1532-1542.e2. doi:10.1016/j.jogc.2020.04.006.

Fialova et al. Relationship of pregnancy associated plasma protein A to renal function and dialysis modalities. Kidney Blood Press Res. 2004; 27: 88-95.

Fulcher et al. State and federal abortion restrictions increase risk of COVID-19 exposure by mandating unnecessary clinic visits. Contraception 2020:S0010-7824(20)385-391.

Folkersen et al Pregnancy-associated plasma protein A: circulating levels during normal pregnancy. Am J Obstet Gynecol. Apr. 15, 1981;139(8):910-4.

Ghaemi et al., Multiomics modeling of the immunome, transcriptome, microbiome, proteome and metabolome adaptations during human pregnancy,' Bioinformatics. 2019;35(1):95-103.

Gyrup et al., "Quantification of proteolytically active pregnancy-associated plasma protein-A with an assay based on quenched fluorescence," Clin Chem. May 2007;53(5):947-54.

Hanley et al., "A method of comparing the areas under receiver operating characteristic curves derived from the same cases," Radiology. 1983 148(3):839-843. doi:10.1148/radiology.148.3.6878708.

Harrison et al. Maternal plasma, human placental lactogen, alpha-fetoprotein, prolactin and growth hormone in early pregnancy. 1980. Int J Gynaecol Obstet. 17(5):471-476.

Harstad et al., "Tissue-specific changes in pregnancy associated plasma protein-A expression with age in mice," Exp Gerontol. Sep. 2014; 57:13-7.

Honarjoo et al., "Role of pregnancy-associated plasma protein A (PAPP-A) and human-derived chorionic gonadotrophic hormone (free β-hCG) serum levels as a marker in predicting of Small for gestational age (SGA): A cohort study," J Res Med Sci. Nov. 29, 2021;26:104. doi: 10.4103/jrms.JRMS_560_20. PMID: 35126567; PMCID: PMC8765518.

Insler et al. "Monitoring of Pregnancy and Fetal Well-Being. 1979. Practical Obstetrics and Gynecology." Manual of Selected Procedures and Treatments. Basel, Karger, pp. 1-11.

Kapp et al., "Medical abortion in the late first trimester: a systematic review," Contraception. 2019;99(2):77-86. doi:10.1016/j.contraception.2018.11.002.

Kapp et al., "A research agenda for moving early medical pregnancy termination over the counter," BJOG 2017;124:1646-52.

Kirkegaard et al., "Biology of pregnancy-associated protein-A in relation to prenatal diagnostics: an overview," Acta Obstet Gynecol Scand. Sep. 2010;89(9):1118-25. Review. PubMed PMID: 20804336.

Lambert-Messerlian et al., "Examination of the pregnancy-associated plasma protein-A assay on the Beckman Coulter Access(®) platform: suitability for use in first trimester Down's syndrome screening," J Med Screen. 2010;17(3):109-13.

Lambert-Messerlian et al., "Measuring maternal serum screening markers for Down's syndrome in plasma collected for cell-free DNA testing," J Med Screen. Sep. 2017;24(3):113-119. doi: 10.1177/0969141316670193. Epub Oct. 21, 2016. PMID: 28756761.

Landis et al., "The measurement of observer agreement for categorical data," Biometrics. Mar. 1977;33(1):159-74. PubMed PMID: 843571.

Laursen et al., "Pregnancy-associated plasma protein-A (PAPP-A) cleaves insulin-like growth factor binding protein (IGFBP)-5 independent of IGF: implications for the mechanism of IGFBP-4 proteolysis by PAPP-A," FEBS Lett. Aug. 24, 2001;504(1-2):36-40. PubMed PMID: 11522292.

Laigaard et al. "ADAM12: a novel first-trimester maternal serum marker for Down syndrome." Prenat Diagn 2003;23:1086-91.

Lin. "A concordance correlation coefficient to evaluate reproducibility," Biometrics. (1989) 45(1):255-268.

Loubiere et al., "Economic evaluation of point-of-care diagnostic technologies for infectious diseases," Clin Microbiol Infect. (2010) 16(8):1070-6.

Macaulay et al., "Reliability and validity of last menstrual period for gestational age estimation in a low-to-middle-income setting," J Obstet Gynaecol Res. (2019) 45(1):217-25.

Mazer Zumaeta et al., "Screening for trisomy at 11-13 weeks' gestation: use of pregnancy-associated plasma protein-A, placental growth factor or both," Ultrasound Obstet Gynecol. (2020) 56(3):408-15.

Mazer Zumaeta et al., "Screening for pre-eclampsia at 11-13 weeks' gestation: use of pregnancy-associated plasma protein-A, placental growth factor or both," Ultrasound Obstet Gynecol 2020;56(3):400-7.

Meiramova et al. Placental growth factor and maternal characteristics in the first trimester among pregnant women of Kazakh nationality. 2018. Georgian Med News. 279:29-32.

Metz. "Basic principles of ROC analysis." Semin Nucl Med. 1978;8:283-98. [PubMed].

Naiem et al., "Comparison of pregnancy-specific β1-glycoprotein (SP1) and ultrasound in predicting the date of delivery," Br J Obstet Gynaecol (1988) 95(2):116-119.

Nicolaides. First-trimester screening for chromosomal abnormalities. Semin Perinatol. Aug. 2005;29(4):190-4. Review. PubMed PMID: 16104667.

(56) References Cited

OTHER PUBLICATIONS

Nishizawa et al., "Increased levels of pregnancy-associated plasma protein-A2 in the serum of pre-eclamptic patients," Mol Hum Reprod. Oct. 2008;14(10):595-602. doi: 10.1093/molehr/gan054. Epub Sep. 18, 2008. PMID: 18805800.
Nomogram for Bayes's Theorem. *N Engl J Med.* 1975;293(5):257-257. doi:10.1056/NEJM197507312930513.
Ong et al. "First-trimester maternal serum levels of placenta growth factor as predictor of preeclampsia and fetal growth restriction." Obstet Gynecol 2001;98:608-11.
Overgaard et al., "Pregnancy associated plasma protein-A2 (PAPP-A2), a novel insulin-like growth factor-binding protein-5 proteinase," J Biol Chem. Jun. 15, 2001;276(24):21849-53. PubMed PMID: 11264294.
Overgaard et al., "Messenger ribonucleic acid levels of pregnancy-associated plasma protein-A and the preform of eosinophil major basic protein: expression in human reproductive and nonreproductive tissue," Biol Reprod 1999; 61:1083-1089.
Oxvig et al, "Circulating human pregnancy associated plasma protein-A is disulfide-bridged to the proform of eosinophil major basic protein," J Biol Chem. Jun. 15, 1993;268(17):12243-6. PubMed PMID: 7685339.
Passing et al., "A new biometrical procedure for testing the equality of measurements from two different analytical methods. Application of linear regression procedures for method comparison studies in clinical chemistry," Part I. J Clin Chem Clin Biochem. Nov. 1983;21(11):709-20. PubMed PMID: 6655447.
Perkins et al., The inconsistency of "optimal" cutpoints obtained using two criteria based on the receiver operating characteristic curve. Am J Epidemiol 2006;163(7):670-5.
Qin et al., "Point-of-care time-resolved immunofluorometric assay for human pregnancy-associated plasma protein A: use in first-trimester screening for Down syndrome," Clin Chem 2002;48(3):473-83.
Qin et al., "Immunoassays developed for pregnancy-associated plasma protein-A (PAPP-A) in pregnancy may not recognize PAPP-A in acute coronary syndromes," Clin Chem 2006;52(3):398-404.
Qin et al., "Molecular distinction of circulating pregnancy-associated plasma protein A in myocardial infarction and pregnancy," Clin Chem 2005;51(1):75-83.
Qin et al., "Double-monoclonal immunofluorometric assays for pregnancy-associated plasma protein A/proeosinophil major basic protein (PAPP-A/proMBP) complex in first-trimester maternal serum screening for Down syndrome," Clinical Chemistry, vol. 43, Issue 12, Dec. 1, 1997, pp. 2323-2332.
Raymond et al., "First-trimester medical abortion with mifepristone 200 mg and misoprostol: a systematic review," Contraception. 2013 87(1):26-37. doi:10.1016/j.contraception.2012.06.011.
Raymond et al. Reaching women where they are: eliminating the initial in-person medical abortion visit. Contraception 2015;92:190-3.
Raymond et al. Simplified medical abortion screening: a demonstration project. Contraception 2018;97:292-6.
Raymond et al., "Sensitivity and specificity of placental proteins for gestational age screening: An exploratory study," Contraception. 2020;101(5):309-314. doi:10.1016/j.contraception.2020.01.007.
Romero et al., "The maternal plasma proteome changes as a function of gestational age in normal pregnancy: a longitudinal study," Am J Obstet Gynecol 2017;217(67):e1-e21.
Safe Abortion: Technical and Policy Guidance for Health Systems. 2nd edition. Geneva: World Health Organization; 2012. PubMed PMID: 23700650.
Schindler et al. Histochemical localization of pregnancy associated plasma protein-A in fetal, infant, and adult organs and camparison between antisera. Gynecol Obstet Invest. 1984; 18: 88-94.
Spencer et al., "The influence of ethnic origin on first trimester biochemical markers of chromosomal abnormalities," Prenat Diagn 2000;20:491-4.
Su et al. "Decreased maternal serum placenta growth factor in early second trimester and preeclampsia." Obstet Gynecol 2001;97:898-904.
Tzur et al. "Expectant vs medical management for retained products of conception after medical termination of pregnancy: a randomized controlled study." *American Journal of Obstetrics and Gynecology* 227.4 (2022): 599-e1.
Wald et al. Combining ultrasound and biochemistry in first-trimester screening for down's syndrome. Prenatal Diagnosis 1997;17:821-9.
Westergaard et al. Accurate assessment of early gestational age by measuring serum hCG and SP1. Lancet 1983;2:567-8.
Whittaker et al., "Accurate assessment of early gestational age in normal and diabetic women by serum human placental lactogen concentration," 1983. The Lancet. 2(8345):304-306.
Winikoff et al. Extending outpatient medical abortion services through 70 days of gestational age. Obstet Gynecol. Nov. 2012;120(5):1070-6. PubMed PMID: 23090524.
Xin et al. Protein-to-creatinine ratio in spot urine samples as a predictor of quantitation of proteinuria. Clin Chim Acta 2004;350:35-9.
Yang et al. PAPP-A affects tendon structure and mechanical properties. J Struct Biol. Oct. 2015; 192(1):59-66.
Youden, "Index for rating diagnostic tests," Cancer 1950;3(1):32-5.
"WHO recommendations on antenatal care for a positive pregnancy experience," World Health Organization (2016) retrieved from https://www.who.int/reproductivehealth/publications/maternal_perinatal_health/anc-positive-pregnancy-experience/en/.
Ahmed et al. Observations on the dating of pregnancy. Eur J Obstet Gynecol Reprod Biol. Dec. 1985;20(6):347-55.
Alldred et al., "First trimester serum tests for Down's syndrome screening," Cochrane Database Syst Rev (2015) 11:CD011975.
Bersinger et al., "Comparison of the concentration of schwangerschaftsprotein 1 (SP1) in the serum and urine of pregnant women," Gynecol Obstet Invest (1986) 21(3):113-116.
Bersinger et al., "Serum concentration of pregnancy specific and pregnancy-associated proteins in early gestation," Arch Gynecol (1986) 237(4):221-228.
Cowans et al. ADAM-12 stability in first trimester maternal serum. Prenat Diagn. Jun. 2010;30(6):555-60.
Czekierdowski et al. The role of 1st trimester PAPP-A, ADAM-12 and inhibin-A assessment in low-risk population of pregnant women. 2008. Archives of perinatal medicine 14(4):44-48.
Davies et al., "Antibody-antigen complexes," Annu Rev Biochem (1990) 59:439-473.
Fescina et al., "Sexual & Reproductive Health Guides For The Phc Focused Continuum Of Care Of Women And Newborns," Continuum of Care of Women and Newborns (2009) Scientific Publication CLAP/WR N'1562.02.
Johnson et al. Accuracy of a home-based device for giving an early estimate of pregnancy duration compared with reference methods. Fertility and sterility. 2013. vol. 100, Issue 6, pp. 1635-1641.e1.
Kasdaglis et al. Placental growth factor in the first trimester: relationship with maternal factors and placental Doppler studies. 2010. Ultasound Obstet Gynecol. 35:280-285.
Korevaar et al. Reference ranges and determinants of total hCG levels during pregnancy: the Generation R Study. 2015 Eur J Epidemiol. 30(9): 1057-1066.
Lagrew et al., "Determination of gestational age by serum concentrations of human chorionic gonadotropin," Obstet Gynecol (1983) 62(1):37-40.
Laigaard et al. The level of ADAM-12 in amternal serum is an early first-trimester marker of fetal trisomy 18. Prenatal Diagnosis. 2005. 25(1):45-46.
Laigaard J. et al. ADAM12: a novel first-trimester maternal serum marker for Down syndrome, Prenatal Diagnosis (2004) 23(13):1086-1091.
Larsen et al. Human chorionic gonadotropin as a measure of pregnancy duration. Int J Gynaecol Obstet. Dec. 2013;123(3):189-95.
Makrydimas et al. ADAM12-s in coelomic fluid and maternal serum in early Pregnancy. Prenat Diagn. Dec. 2006;26(13):1197-200.
Malmqvist, "Biospecific interaction analysis using biosensor technology," Nature (1993) 361:186-187.

(56) References Cited

OTHER PUBLICATIONS

Pihl et al. First trimester maternal serum pregnancy-specific beta-1-glycoprotein (SP1) as a marker of adverse pregnancy outcome. 2009. Prenat Diagn. Dec. 2009;29(13):1256-61.

Raymond et al., "Sensitivity and specificity of placental proteins for gestational age screening: An exploratory study," Contraception (2020) 101(5):P309-314.

Romero et al., "The maternal plasma proteome changes as a function of gestational age in normal pregnancy: a longitudinal study," American Journal of Obstetrics of Gynecology (2017) 217(1):67.e1-67.e21.

Shiefa et al., "First Trimester Maternal Serum Screening Using Biochemical Markers PAPP-A and Free β-hCG for Down Syndrome, Patau Syndrome and Edward Syndrome," Indian J Clin Biochem (2013) 28(1):3-12.

Stemp et al. Serum concentrations of the biomarkers CA125, CA15-3, PSA and PAPP-A in early pregnancy. Journal of Reproductive Biotechnology and Fertility. 2016. https://doi.org/10.1177/2058915816672102.

Thomson et al. The value of serum human placental lactogen and Schwangerschaftsprotein 1 to determine gestation in an ante-natal population. 1988. Hum Reprod. 3(4):463-465.

Torring et al., "First trimester screening for trisomy 21 in gestational week 8-10 by ADAM12-S as a maternal serum marker," Reprod Biol Endocrinol. (2010) 8:129.

Tsiakkas et al. Serum placental growth factor in the three trimesters of pregnancy: effects of maternal characteristics and medical history 2015. Ultrasound in obstetrics and gynecology. 45(5): 591-598.

Wright et al., "Serum pregnancy-associated plasma protein-A in the three trimesters of pregnancy: effects of maternal characteristics and medical history," Ultrasound Obstet Gynecol 2015; 46: 42-50.

Zapata et al., "Engineering linear F(ab')2 fragments for efficient production in *Escherichia coli* and enhanced antiproliferative activity," Protein Eng (1995) 8(10):1057-1062.

Yarbrough et al., "Pregnancy and its disorders." In: Rifai N, Horvath AR, Wittwer CT, editors. Tietz Textbook of Clinical Chemistry and Molecular Diagnostics. 6th Ed. St. Louis, MO: Elsevier; (2018). 1655-96.

Buhimschi et al., "In Reply to PAPP-A Results Cannot Be Used to Accurately Estimate Gestational Age," J Appl Lab Med. (2022) 7(4):1002-1004.

U.S. Appl. No. 18/266,149, filed Dec. 8, 2021, by Buhimschi et al. (Copy not submitted herewith pursuant to the waiver of 37 C.F.R. § 1.98(a)(2)(iii) issued by the Office on Sep. 21, 2004).

Buhimschi et al., "Analytical comparison of pregnancy-associated plasma protein-A (PAPP-A) immunoassays for biochemical determination of gestational age," JALM (2021) 1517-1532.

Frye et al., "PAPP-A as a screening tool for assessment of gestational age before medication abortion in an intended-use population," Biomark Med (2023) 17(2):73-85.

Anonymous et al., "Human PAPPA ELISA Kit," Cat. No. DEIA2304, Creative Diagnostics, Nov. 29, 2019, Retrieved from the Internet: https://img.creative-diagnostics.com/pdf/DEIA2304,PAPPA.pdf.

Luewan et al., "Median levels of serum biomarkers of fetal Down syndrome detected during the first trimester among pregnant Thai women," Int J Gynaecol Obstet (2012) 117(2):140-143.

Raymond et al., "Using placental proteins in urine and serum to assess gestational age: A new purpose for an old idea," Contraception. (2019) 99(5) Abstract P319.

Spencer et al., "The influence of smoking on maternal serum PAPP-A and free beta hCG levels in the first trimester of pregnancy," Prenat Diagn (1999) 19(11):1065-1066.

Varashree et al., "Influence of obesity on first trimester screening markers in singleton pregnant women enrolled at tertiary care hospital," Malaysian Journal of Biochemistry and Molecular Biology (2019) 22(1):148-151.

* cited by examiner

PLACENTAL PROTEIN BIOMARKERS FOR GESTATIONAL AGE ASSESSMENT AND RELATED METHODS

CROSS-REFERENCE TO RELATED APPLICATIONS

This application claims priority from U.S. provisional application No. 62/857,746 filed Jun. 5, 2019, entitled "PLACENTAL PROTEIN BIOMARKERS FOR GESTATIONAL AGE ASSESSMENT AND RELATED METHODS," the contents of which are incorporated by reference in their entirety.

FIELD

The present disclosure relates to methods, systems and kits for detection of certain placental proteins, such as PAPP-A and ADAM-12, for example, in a serum sample from an individual to classify gestational ages above and below a specific threshold, such as for use in determining gestational age for making clinical or personal decisions without ultrasound.

BACKGROUND

Accurate knowledge of gestational age (GA) is essential for all aspects of prenatal care. Because assessment based on menstrual history and examination of uterine size is often unreliable, clinicians currently use ultrasound routinely to estimate GA. However, ultrasound is expensive, must be performed by a trained technician, and is generally provided only in specialized medical facilities. Thus there remains a need for reagents, devices and methods for determining the gestational age of a pregnancy. In particular, reagents, devices and methods that provide a cheaper, less technical GA estimation tool could be highly beneficial, particularly in low resource settings or when providing care remotely, through telemedicine. Provided herein are embodiments that meet such needs.

SUMMARY

Provided herein is a method for classifying the gestational age (GA) of a pregnancy, the method comprising measuring the concentration of a placental protein from a sample from a pregnant subject, wherein the placental protein is selected from ADAM-12, PAPP-A, PSG1, HPL. The method further includes comparing the concentration to a predetermined threshold level for the placental protein, and determining if the gestational age of the pregnancy is greater than or equal to a predetermined GA cutpoint, thereby classifying the gestational age as predicted to be greater than or equal to the predetermined GA cutpoint or less than the predetermined GA cutpoint. The predetermined GA cutpoint is a timepoint between at or about 5 weeks and at or about 40 weeks.

In some of any of the provided embodiments, the measuring is carried out by an immunoassay. In any of the provided embodiments, the immunoassay is a solid-phase immunoassay. In some of any of the provided embodiments, the immunoassay is an Enzyme linked immunosorbent assay (ELISA). In any of the provided embodiments, the immunoassay is a sandwich ELISA.

In some of any of the provided embodiments, the method further comprises selecting the pregnant subject as a candidate for a prenatal care or a clinical treatment if the gestational age is predicted to be less than the predetermined GA cutpoint.

In some of any of the provided methods, the placental protein is ADAM-12. In some of any of the provided embodiments, the placental protein is PAPP-A. In some of any of the provided embodiments, the placental protein is PSG1. In some of any of the provided embodiments, the placental protein is HPL.

In some of any of the provided embodiments, the steps of measuring, comparing and determining are repeated for each of one or more further placental protein for the same predetermined GA cutpoint. In some of any of the provided embodiments, the steps of measuring, comparing and determining are repeated for each of one or more further placental protein for a different predetermined GA cutpoint. In any of the provided embodiments, each of the one or more further placental protein is another one or more placental protein selected from among ADAM-12, PAPP-A, PSG1, HPL. In some of any of the provided embodiments, the one or more further placental protein is 1 further placental protein or 2 further placental proteins. In any of the provided embodiments, the method further comprises selecting the pregnant subject as a candidate for a prenatal care or a clinical treatment if the gestational age is predicted to be less than the predetermined GA cutpoint for the placental protein and for each of the one or more further placental protein.

In some of any of the provided embodiments, the placental protein and the one or more further placental protein are ADAM-12/PAPP-A, ADAM-12/PSG1, ADAM-12/HPL, PAPP-A/PSG1, PAPP-A/HPL, PSG1/HPL, ADAM-12/PAPP-A/PSG1, ADAM-12/PAPP-A/HPL, ADAM-12/PSG1/HPL, PAPP-A/PSG1/HPL.

In some of any of the provided embodiments, the predetermined GA cutpoint is a timepoint between at or about 5 weeks and at or about 20 weeks, inclusive.

In some of any of the provided embodiments, the placental protein (or the one or more placental protein) is PAPP-A and the predetermined threshold level of PAPP-A is a value between 3 ng/mL and 130 ng/mL, inclusive. In some of any of the provided embodiments, the placental protein (or one of the one or more placental protein) is ADAM-12 and the predetermined threshold level of ADAM-12 is a value between at or about 0.5 ng/mL and at or about 15 ng/mL, inclusive. In any of the provided embodiments, the placental protein (or one of the one or more placental protein) is PSG1 and the predetermined threshold level of PSG1 is a value between at or about 5 ng/mL and at or about 4000 ng/mL. In some embodiments, the predetermined threshold level of PSG1 is a value between at or about 10 ng/mL and at or about 25 ng/mL or a value between at or about 3000 ng/mL and at or about 4000 ng/mL. In some of any of the provided embodiments, the placental protein (or one of the one or more placental protein) is HPL and the predetermined threshold level of HPL is a value between at or 0.02 mg/L and at or about 4 mg/L, inclusive.

In some of any of the provided embodiments, the predetermined GA cutpoint is a timepoint between 64 days and at or about 140 days, inclusive. In some embodiments, the GA cutpoint is or is about 70 days. In some of any of the provided embodiments, the placental protein (or one of the one or more placental protein) is PAPP-A and the predetermined threshold level is a value between at or about 3 ng/mL and at or about 10 ng/mL. In some embodiments, the predetermined threshold level of PAPP-A is a value between at or about 5 ng/mL and 6 ng/mL. In some of any of the provided embodiments, the placental protein (or one of the one or more placental protein) is ADAM-12 and the predetermined threshold level is a value between at or about 0.5 ng/mL and at or about 4 ng/mL. In some embodiments, the predetermined threshold level of ADAM-12 is a value between at or about 2 ng/mL and at or about 3 ng/mL. In some of any of the provided embodiments, the placental protein (or one of the one or more placental protein) is PSG1 and the predetermined threshold level is a value between at or about 5 ng/mL and at or about 500 ng/mL. In some of any of the provided embodiments, the placental protein (or one of the one or more placental protein) is HPL and the predetermined threshold level is a value between at or about 0.02 mg/L and at or about 0.1 mg/L. In some embodiments, the predetermined threshold level of HPL is a value of at or about 0.03 mg/L.

In some of any of the provided embodiments, the predetermined GA cutpoint is a timepoint between 80 days and at or about 140 days, inclusive. In some of any of the provided embodiments, the GA cutpoint is or is about 104 days. In some of any of the provided embodiments, the GA cutpoint is or is about 105 days. In some of any of the provided embodiments, the placental protein (or one of the one or more placental protein) is PAPP-A and the predetermined threshold level is a value between at or about 10 ng/mL and at or about 70 ng/mL. In some embodiments, the predetermined threshold level of PAPP-A is a value between at or about 40 ng/mL and 50 ng/mL. In some of any of the provided embodiments, the placental protein (or one of the one or more placental protein) is ADAM-12 and the predetermined threshold level is a value between at or about 3.5 ng/mL and at or about 8 ng/mL. In some embodiments, the predetermined threshold level of ADAM-12 is a value between at or about 4 ng/mL and at or about 5 ng/mL. In some of any of the provided embodiments, the placental protein (or one of the one or more placental protein) is PSG1 and the predetermined threshold level is a value between at or about 2000 ng/mL and at or about 5000 ng/mL. In some embodiments, the predetermined threshold level of PSG1 is a value between at or about 3000 ng/mL and at or about 4000 ng/mL. In some of any of the provided embodiments, the placental protein (or one of the one or more placental protein) is HPL and the predetermined threshold level is a value between at or about 0.1 mg/L and at or about 1 mg/L. In some embodiments, the predetermined threshold level of HPL is a value between at or about 0.09 mg/L and at or about 1 mg/L.

In some of any of the provided embodiments, the GA cutpoint is 140 days. In some of any of the provided embodiments, the GA cutpoint is about 140 days. In some of any of the provided embodiments, the placental protein (or one of the one or more placental protein) is PAPP-A and the predetermined threshold level is a value between at or about 60 ng/mL and at or about 130 ng/mL. In some embodiments, the predetermined threshold level of PAPP-A is a value between at or about 70 ng/mL and 80 ng/mL. In some of any of the provided embodiments, the placental protein (or one of the one or more placental protein) is ADAM-12 and the predetermined threshold level is a value between at or about 8 ng/mL and at or about 14 ng/mL. In some embodiments the predetermined threshold level of ADAM-12 is a value between at or about 9 ng/mL and at or about 10 ng/mL. In some of any of the provided embodiments, the placental protein (or one of the one or more placental protein) is PSG1 and the predetermined threshold level is a value between at or about 2000 ng/mL and at or about 5000 ng/mL. In some embodiments, the predetermined threshold level of PSG1 is a value between at or about 3000 ng/mL and at or about 4000 ng/mL. In some of any of the provided embodiments, the placental protein (or one of the one or more placental protein) is HPL and the predetermined threshold level is a value between at or about 1 mg/L and at or about 3 mg/L. In some embodiments, the predetermined threshold level of HPL is a value between at or about 1 mg/L and at or about 2 mg/L.

In some of any of the provided embodiments, the sample is a whole blood or serum sample. In any of the provided embodiments, the method is carried out using a point-of-care device. In any of the provided embodiments, the method is carried out in a laboratory. In any of the provided embodiments, the method is carried out without an ultrasound. In any of the provided embodiments, the method further comprises performing an ultrasound.

Provided herein is a method for screening a pregnant subject for a prenatal care or clinical treatment, the method comprising classifying the gestational age (GA) of a pregnancy according to any of the methods provided herein; and based on the classifying: selecting a pregnant subject as eligible for a prenatal care or clinical treatment if the classified gestational age is less than the predetermined GA cutpoint; or selecting a pregnant subject as not eligible from a prenatal care or clinical treatment and/or as a candidate for further assessment for a prenatal care or prenatal clinical treatment if the classified gestational age is greater than or equal to the predetermined GA cutpoint.

In any of the embodiments provided herein, if a pregnant subject is selected as eligible the method further includes carrying out the prenatal care or prenatal clinical treatment on the pregnant subject. In some of any of the provided embodiments, if a pregnant subject is selected as not eligible, the method further includes administering a medical assessment of the pregnant subject to determine the gestational age. In some embodiments, the medical assessment is or comprises an ultrasound.

Provided herein is a method a prenatal care or prenatal clinical treatment on a pregnant subject, the method comprising performing a prenatal care or prenatal clinical treatment of a pregnant subject selected as eligible for the prenatal care or prenatal clinical treatment according to any of the embodiments provided herein. In some of any of the provided embodiments, the prenatal care or prenatal clinical treatment is a medical abortion or early aspiration, such as wherein the GA cutpoint is at or about 10 weeks (or 70 days). In some of any of the provided embodiments, the prenatal care or clinical treatment is a test for a chromosomal abnormality or a test that involves amniocentesis, such as wherein the GA cutpoint is a timepoint between at or about 15 weeks (105 days) and 18 weeks, inclusive. In some embodiments, the GA cutpoint is at or about 104 days or at or about 105 days. In some of any of the provided embodiments, the prenatal care or prenatal clinical treatment is a glucose tolerance test, such as wherein the GA cutpoint is a timepoint at or greater than 20 weeks, for example between at or about 26 and at or about 28 weeks, inclusive, such as at or about 140 days. In some of any of the provided embodiments, the prenatal care or prenatal clinical treatment is a decision about the risk of embryotoxicity, such as wherein the GA cutpoint is a timepoint between at or about 8 weeks and at or about 10 weeks, inclusive, for example wherein the GA cutpoint is at or about 10 weeks.

Provided herein is a device for carrying out the methods of any of the embodiments described herein. In some of any of the provided embodiments, the device is hand-held device or point-of-care device.

Provided herein is a method for predicting the gestational age of a pregnant subject, the method comprising (a) measuring the concentration of a placental protein from a sample from a pregnant subject, wherein the placental protein is selected from ADAM-12, PAPP-A, PSG1, and HPL; and (b) predicting the gestational age of the pregnancy based on the concentration, wherein the predicting comprises providing the concentration as input to a process that uses concentration of the placental protein as a continuous predictor of gestational age.

Provided herein is a method for selecting a prenatal care or prenatal clinical treatment for a pregnant subject, the method comprising (a) measuring the concentration of a placental protein from a sample from a pregnant subject, wherein the placental protein is selected from ADAM-12, PAPP-A, PSG1, and HPL; (b) predicting the gestational age of the pregnancy based on the concentration, wherein the predicting comprises providing the concentration as input to a process that uses concentration of the placental protein as a continuous predictor of gestational age; and (c) selecting a prenatal care or prenatal clinical treatment for the pregnant subject based on the gestational age of the pregnancy.

Provided herein is a method for performing a prenatal care or prenatal clinical treatment on a pregnant subject, the method comprising (1) classifying the gestational age (GA) of a pregnancy according to a method comprising (a) measuring the concentration of a placental protein from a sample from a pregnant subject, wherein the placental protein is selected from ADAM-12, PAPP-A, PSG1, and HPL; (b) comparing the concentration to a predetermined threshold level for the placental protein, wherein the predetermined threshold level is for a predetermined GA cutpoint; and (c) determining if the gestational age of the pregnancy is greater than or equal to the predetermined GA cutpoint, wherein the predetermined GA cutpoint is a timepoint between at or about 5 weeks and at or about 40 weeks; the gestational age of the pregnancy is determined to be less than the predetermined GA cutpoint if the concentration is lower than the predetermined threshold level; and the gestational age of the pregnancy is determined to be greater than or equal to the predetermined GA cutpoint if the concentration is higher than or equal to the predetermined threshold level; thereby classifying the gestational age as predicted to be greater than or equal to the predetermined GA cutpoint or less than the predetermined GA cutpoint; (2) based on the classifying, selecting the pregnant subject as eligible for a prenatal care or prenatal clinical treatment if the classified gestational age is less than the predetermined GA cutpoint; and (3) performing the prenatal care or prenatal clinical treatment on the pregnant subject selected as eligible for the prenatal care or prenatal clinical treatment.

In some embodiments, the measuring is carried out by an immunoassay. In some of any of the provided embodiments, steps (a)-(c) are repeated for each of one or more further placental protein for the same predetermined GA cutpoint. In some embodiments, the pregnant subject is eligible for the prenatal care or prenatal clinical treatment if the classified gestational age for the placental protein and for each of the one or more further placental protein is less than the predetermined GA cutpoint.

Provided herein is a method for performing a prenatal care or prenatal clinical treatment on a pregnant subject, the method comprising performing a prenatal care or prenatal clinical treatment on a pregnant subject selected as eligible for the prenatal care or prenatal clinical treatment, wherein the pregnant subject is selected as eligible for the prenatal care or prenatal clinical treatment if the classified gestational age of the pregnancy is less than a predetermined GA cutpoint, wherein the predetermined GA cutpoint is a timepoint between at or about 5 weeks and at or about 40 weeks; the gestational age of the pregnancy is determined to be less than the predetermined GA cutpoint if the measured concentration of a placental protein from a sample from the pregnant subject is lower than a predetermined threshold level for the placental protein; the gestational age of the pregnancy is determined to be greater than or equal to the predetermined GA cutpoint if the concentration is higher than or equal to the predetermined threshold level; the predetermined threshold level is for a predetermined GA cutpoint; and the placental protein is selected from ADAM-12, PAPP-A, PSG1, and HPL.

In some embodiments, the concentration is measured by an immunoassay. In some of any of the provided embodiments, gestational age is classified for each of one or more further placental protein for the same predetermined GA cutpoint. In some embodiments, the pregnant subject is eligible for the prenatal care or prenatal clinical treatment if the classified gestational age for the placental protein and for each of the one or more further placental protein is less than the predetermined GA cutpoint.

In some of any of the provided embodiments, the immunoassay is a solid-phase immunoassay. In some of any of the provided embodiments, the immunoassay is an Enzyme linked immunosorbent assay (ELISA). In some of any of the provided embodiments, the immunoassay is a sandwich ELISA.

In some of any of the provided embodiments, the placental protein is ADAM-12. In some of any of the provided embodiments, the placental protein is PAPP-A. In some of any of the provided embodiments, the placental protein is PSG1. In some of any of the provided embodiments, the placental protein is HPL.

In some of any of the provided embodiments, each of the one or more further placental protein is another placental protein selected from among ADAM-12, PAPP-A, PSG1, and HPL. In some of any of the provided embodiments, the one or more further placental protein is 1 further placental protein or 2 further placental proteins. In some of any of the provided embodiments, the placental protein and the one or more further placental protein are ADAM-12/PAPP-A, ADAM-12/PSG1, ADAM-12/HPL, PAPP-A/PSG1, PAPP-1/HPL, PSG1/HPL, ADAM-12/PAPP-A/PSG1, ADAM-12/PAPP-A/HPL, ADAM-12/PSG1/HPL, or PAPP-A/PSG1/HPL.

In some of any of the provided embodiments, the predetermined GA cutpoint is a timepoint between at or about 5 weeks and at or about 20 weeks, inclusive. In some of any of the provided embodiments, the placental protein and/or the one or more placental protein is PAPP-A and the predetermined threshold level of PAPP-A is a value between 3 ng/mL and 130 ng/mL, inclusive. In some of any of the provided embodiments, the placental protein and/or the one or more placental protein is ADAM-12 and the predetermined threshold level of ADAM-12 is a value between at or about 0.5 ng/mL and at or about 15 ng/mL, inclusive. In some of any of the provided embodiments, the placental protein and/or the one or more placental protein is PSG1 and the predetermined threshold level of PSG1 is a value between at or about 5 ng/mL and at or about 4000 ng/mL, inclusive. In some of any of the provided embodiments, the placental protein and/or the one or more placental protein is HPL and the predetermined threshold level of HPL is a value between at or 0.02 mg/L and at or about 4 mg/L, inclusive.

In some of any of the provided embodiments, the predetermined GA cutpoint is a timepoint between at or about 64 days and at or about 140 days, inclusive. In some of any of the provided embodiments, the predetermined GA cutpoint is or is about 70 days. In some of any of the provided embodiments, the placental protein is PAPP-A and the predetermined threshold level is a value between at or about 3 ng/mL and at or about 10 ng/mL, inclusive; the placental protein is ADAM-12 and the predetermined threshold level is a value between at or about 0.5 ng/mL and at or about 4 ng/mL, inclusive; the placental protein is PSG1 and the predetermined threshold level is a value between at or about 5 ng/mL and at or about 500 ng/mL, inclusive; or the placental protein is HPL and the predetermined threshold level is a value between at or about 0.02 mg/L and at or about 0.1 mg/L, inclusive.

In some of any of the provided embodiments, the predetermined GA cutpoint is a timepoint between 70 days and at or about 140 days, inclusive. In some of any of the provided embodiments, the GA cutpoint is or is about 104 days. In some of any of the provided embodiments, the GA cutpoint is or is about 105 days. In some of any of the provided embodiments, the placental protein is PAPP-A and the predetermined threshold level is a value between at or about 10 ng/mL and at or about 70 ng/mL, inclusive; the placental protein is ADAM-12 and the predetermined threshold level is a value between at or about 3.5 ng/mL and at or about 8 ng/mL, inclusive; the placental protein is PSG1 and the predetermined threshold level is a value between at or about 2000 ng/mL and at or about 5000 ng/mL, inclusive; or the placental protein is HPL and the predetermined threshold level is a value between at or about 0.1 mg/L and at or about 1 mg/L, inclusive.

In some of any of the provided embodiments, the GA cutpoint is or is about 140 days. In some of any of the provided embodiments, the placental protein is PAPP-A and the predetermined threshold level is a value between at or about 60 ng/mL and at or about 130 ng/mL, inclusive; the placental protein is ADAM-12 and the predetermined threshold level is a value between at or about 8 ng/mL and at or about 14 ng/mL, inclusive; the placental protein is PSG1 and the predetermined threshold level is a value between at or about 2000 ng/mL and at or about 5000 ng/mL, inclusive; or the placental protein is HPL and the predetermined threshold level is a value between at or about 1 mg/L and at or about 3 mg/L, inclusive.

In some of any of the provided embodiments, the sample is a whole blood or serum sample. In some of any of the provided embodiments, the method is carried out using a point-of-care device. In some of any of the provided embodiments, the method is carried out in a laboratory. In some of any of the provided embodiments, the method is carried out without an ultrasound. In some of any of the provided embodiments, the method further comprises performing an ultrasound.

In some of any of the provided embodiments, the prenatal care or prenatal clinical treatment is selected from a medical abortion or early aspiration; a test for a chromosomal abnormality or a test that involves amniocentesis; a glucose tolerance test; and a decision about the risk of embryotoxicity. In some of any of the provided embodiments, the prenatal care or prenatal clinical treatment is a medical abortion or early aspiration. In some of any of the provided embodiments, the prenatal care or prenatal clinical treatment is a test for a chromosomal abnormality or a test that involves amniocentesis. In some of any of the provided embodiments, the prenatal care or prenatal clinical treatment is a glucose tolerance test. In some of any of the provided embodiments, the prenatal care or prenatal clinical treatment is a decision about the risk of embryotoxicity.

Provided herein is a device for carrying out the method of any of the provided embodiments. In some embodiments, the device is a hand-held device or a point-of-care device.

Provided herein is a method for performing a prenatal care or prenatal clinical treatment on a pregnant subject, the method comprising (a) measuring the concentration of a placental protein from a sample from a pregnant subject, wherein the placental protein is selected from ADAM-12, PAPP-A, PSG1, and HPL; (b) predicting the gestational age of the pregnancy based on the concentration, wherein the predicting comprises providing the concentration as input to a process that uses concentration of the placental protein as a continuous predictor of gestational age; (c) selecting a prenatal care or prenatal clinical treatment for the pregnant subject based on the gestational age of the pregnancy; and (d) performing the prenatal care or prenatal clinical treatment on the pregnant subject.

In some embodiments, the measuring is carried out by an immunoassay. In some of any of the provided embodiments, steps (a)-(b) are repeated for each of one or more further placental protein. In some embodiments, the prenatal care or prenatal clinical treatment is selected based on the predicted gestational ages for the placental protein and the one or more further placental protein.

Provided herein is a method for performing a prenatal care or prenatal clinical treatment on a pregnant subject, the method comprising performing on a pregnant subject a prenatal care or prenatal clinical treatment selected for the pregnant subject based on the gestational age of the pregnancy, wherein the gestational age of the pregnancy is predicted based on a measured concentration of a placental protein from a sample from the pregnant subject, wherein the predicting comprises providing the concentration as input to a process that uses concentration of the placental protein as a continuous predictor of gestational age; and the placental protein is selected from ADAM-12, PAPP-A, PSG1, and HPL.

In some embodiments, the concentration is measured by an immunoassay. In some of any of the provided embodiments, gestational age is predicted using each of one or more further placental protein. In some embodiments, the prenatal care or prenatal clinical treatment is selected based on the predicted gestational ages for the placental protein and the one or more further placental protein.

In some of any of the provided embodiments, the process comprises a regression model trained using gestational ages and concentrations of the placental protein from a plurality of pregnant subjects. In some of any of the provided embodiments, the process comprises a regression model that is a multiple regression model, and the multiple regression model is trained using gestational ages, concentrations of the placental protein, and concentrations of each of one or more further placental protein. In some of any of the provided embodiments, the regression model is a linear regression model, a piecewise linear model, a polynomial regression model, or a Bayesian model.

In some of any of the provided embodiments, the immunoassay is a solid-phase immunoassay. In some of any of the provided embodiments, the immunoassay is an Enzyme linked immunosorbent assay (ELISA). In some of any of the provided embodiments, the immunoassay is a sandwich ELISA.

In some of any of the provided embodiments, the placental protein is ADAM-12. In some of any of the provided embodiments, the placental protein is PAPP-A. In some of any of the provided embodiments, the placental protein is PSG1. In some of any of the provided embodiments, the placental protein is HPL.

In some of any of the provided embodiments, each of the one or more further placental protein is another placental protein selected from among ADAM-12, PAPP-A, PSG1 and HPL. In some of any of the provided embodiments, the one or more further placental protein is 1 further placental protein or 2 further placental proteins. In some of any of the provided embodiments, the placental protein and the one or more further placental protein are ADAM-12/PAPP-A, ADAM-12/PSG1, ADAM-12/HPL, PAPP-A/PSG1, PAPP-1/HPL, PSG1/HPL, ADAM-12/PAPP-A/PSG1, ADAM-12/PAPP-A/HPL, ADAM-12/PSG1/HPL, or PAPP-A/PSG1/HPL.

In some of any of the provided embodiments, the sample is a whole blood or serum sample. In some of any of the provided embodiments, the method is carried out using a point-of-care device. In some of any of the provided embodiments, the method is carried out in a laboratory. In some of any of the provided embodiments, the method is carried out without an ultrasound. In some of any of the provided embodiments, the method further comprises performing an ultrasound.

In some of any of the provided embodiments, the prenatal care or prenatal clinical treatment is selected from a medical abortion or early aspiration; a test for a chromosomal abnormality or a test that involves amniocentesis; a glucose tolerance test; a decision about the risk of embryotoxicity; a clinical examination; a vaccination; a risk assessment; a fetal assessment; a blood assay; a urine assay; vitamin supplementation; a test for disease; education; counseling; and any combination of any of the foregoing. In some of any of the provided embodiments, the prenatal care or prenatal clinical treatment is a medical abortion or early aspiration. In some of any of the provided embodiments, the prenatal care or prenatal clinical treatment is a test for a chromosomal abnormality or a test that involves amniocentesis. In some of any of the provided embodiments, the prenatal care or prenatal clinical treatment is a glucose tolerance test. In some of any of the provided embodiments, the prenatal care or prenatal clinical treatment is a decision about the risk of embryotoxicity.

Provided herein is a device for carrying out the method of any of the provided embodiments. In some embodiments, the device is a hand-held device or a point-of-care device.

BRIEF DESCRIPTION OF THE DRAWINGS

FIG. 2A provides a scatterplot of serum concentration across the gestational age (GA) range. FIG. 2B provides a zoomed scatterplot with a line designating an exemplary GA cutpoint (70 days) and threshold level. FIG. 2C provides a zoomed scatterplot with a line designating an exemplary GA cutpoint (104 days) and threshold level. FIG. 2D provides a zoomed scatterplot with a line designating an exemplary GA cutpoint (140 days) and threshold level. FIG. 2E provides a zoomed scatterplot with a line designating an exemplary GA cutpoint (140 days) and threshold level.

FIG. 3A provides a scatterplot of serum concentration across the gestational age (GA) range. FIG. 3B provides a zoomed scatterplot with a line designating an exemplary GA cutpoint and threshold level.

FIG. 4A provides a scatterplot of serum concentration across the gestational age (GA) range. FIG. 4B provides a zoomed scatterplot with a line designating an exemplary GA cutpoint and threshold level.

FIG. 5A provides a scatterplot of serum concentration across the gestational age (GA) range. FIG. 5B provides a zoomed scatterplot with a line designating an exemplary GA cutpoint and threshold level.

DETAILED DESCRIPTION

Figure 1:
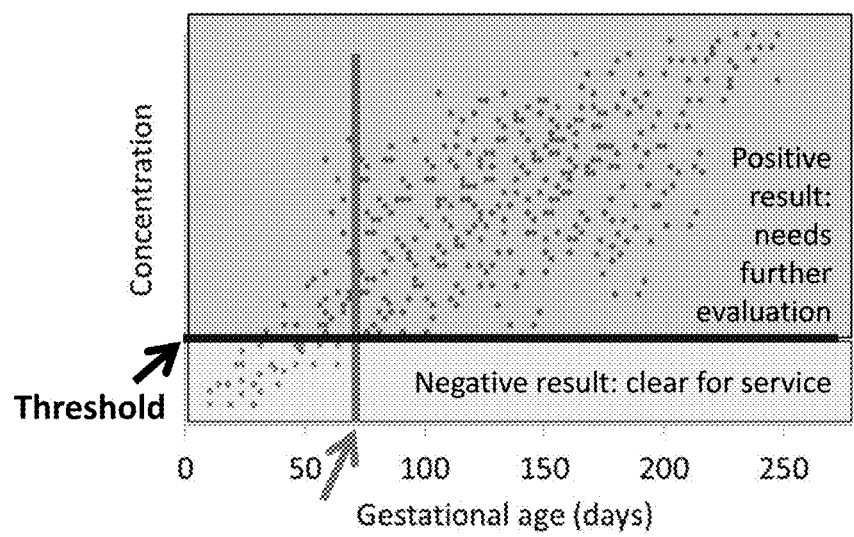
FIG. 1 shows a depiction of a hypothetical test based on concentration in a sample of a placental protein that would reliably exclude women with a gestational age (GA) above a limit (e.g. positive test) and exclude few women with GA below limit (e.g. negative test).
Figure 2A:
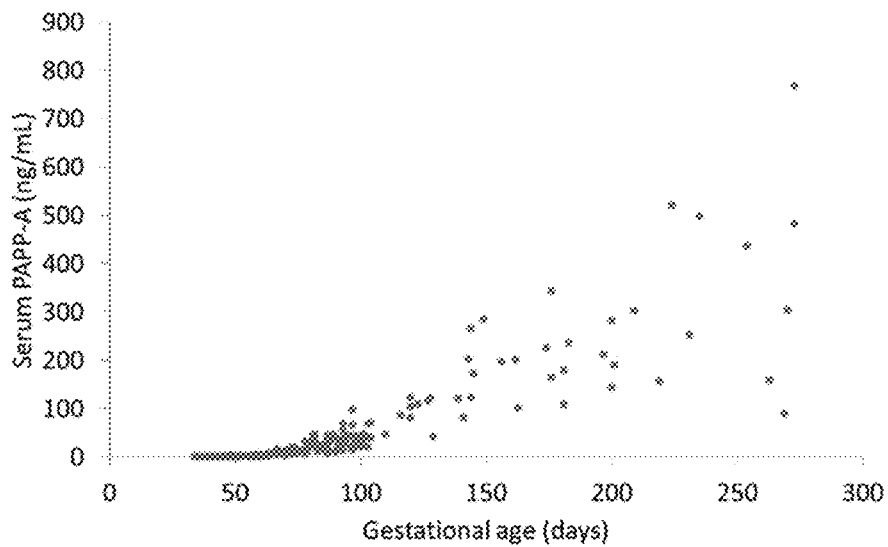
FIGS. 2A-2E show results for serum concentration of PAPP-A (ng/mL) plotted by gestational age of pregnancy of female subjects.
Figure 2B:
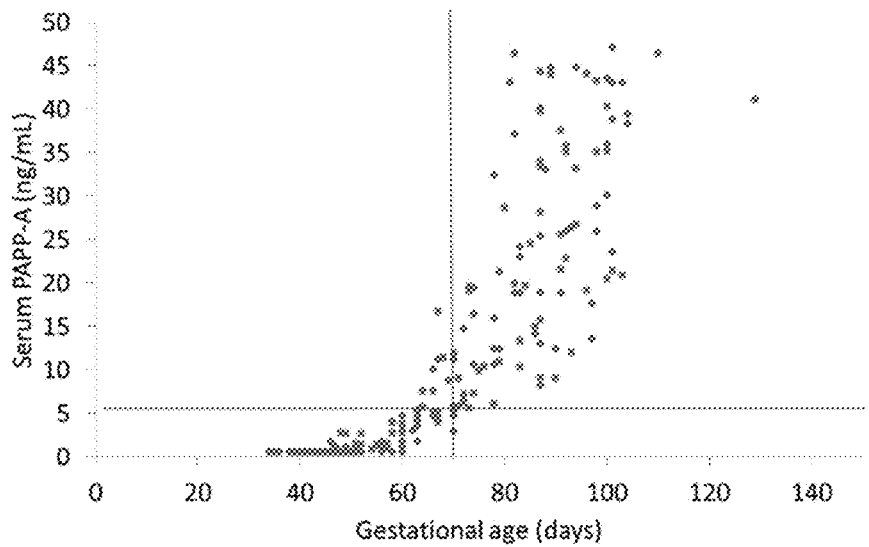
Figure 2C:
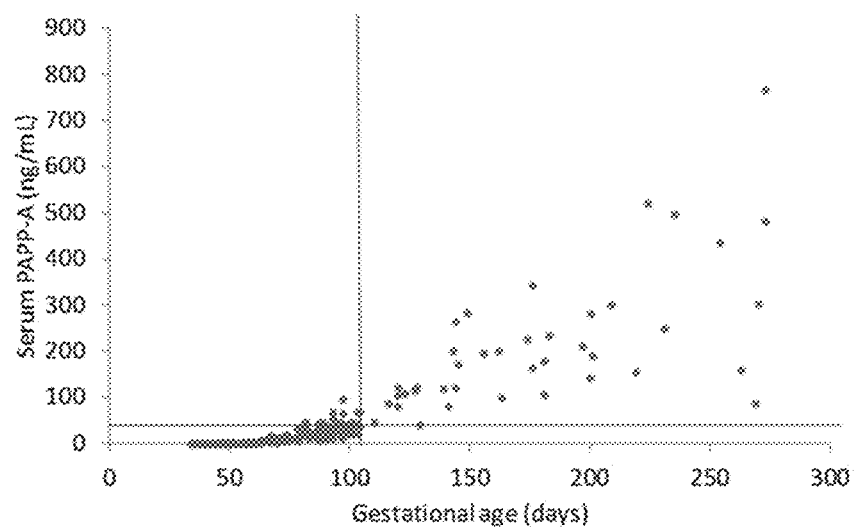
Figure 2D:
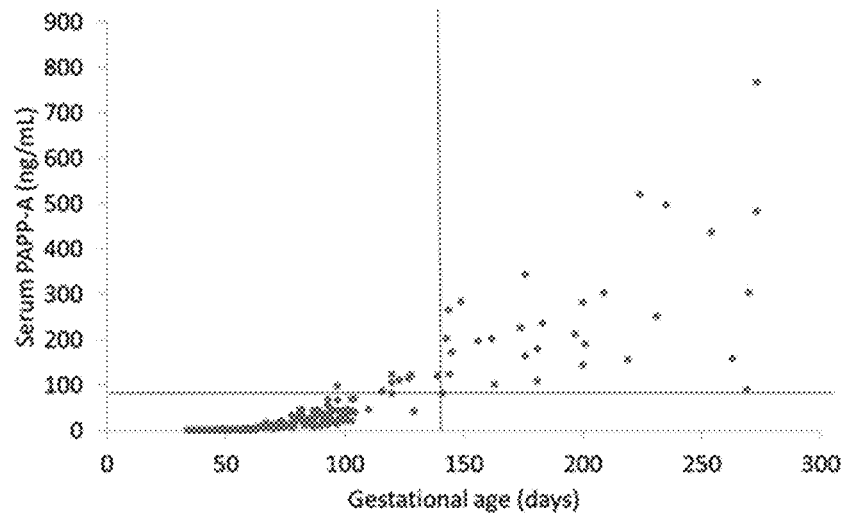
Figure 2E:
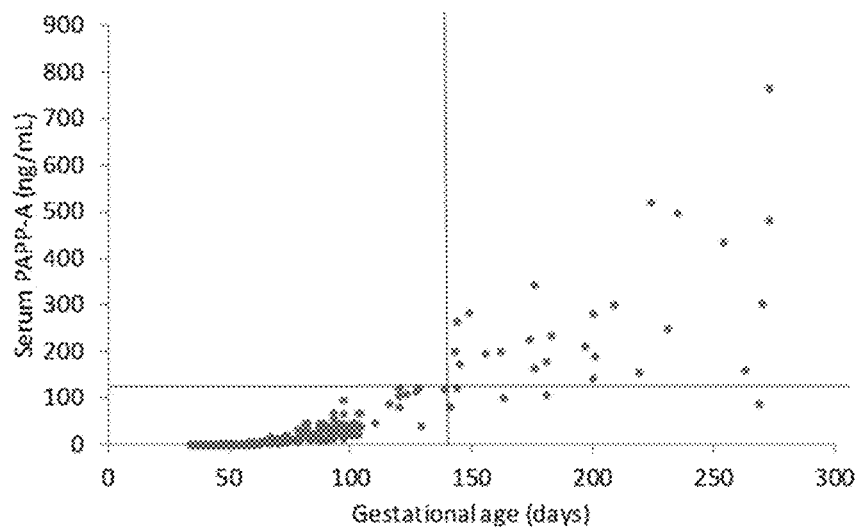

Provided herein is a blood test to estimate or classify gestational age (GA) of a pregnancy. The provided methods can be used to determine or estimate the GA of a pregnancy above or below a GA cutpoint or threshold as determined based on a concentration threshold of a particular biomarker or biomarkers in a sample from the pregnant subject, such as a serum sample. Provided embodiments also relate to predicting the GA of a pregnant subject based on a measured concentration of a particular biomarker in a sample from the pregnant subject, such as a serum sample, in which such provided biomarker or biomarkers can be a continuous predictor of the GA across a range of different GAs. In provided methods, the provided biomarker or biomarkers is a placental protein, such as ADAM-12, PAPP-A, PSG1 (SP1), and HPL, and combinations thereof. In provided embodiments, the placental protein is PAPP-A. In provided embodiments, the placental protein is ADAM-12.

In some embodiments, the provided methods involve detecting, e.g. measuring, one or more placental protein (protein expressed during pregnancy by the human placenta) from among ADAM-12, PAPP-A, PSG1 (SP1), and HPL, and combinations thereof from a sample from a pregnant subject to determine the amount (e.g. concentration) of the one or more placental protein in the sample. In some embodiments, the method is a blood test in which the sample is a serum, plasma or whole blood sample. In particular embodiments, the sample is a serum sample.

In some embodiments, the methods provided herein include after determining the amount (e.g. concentration) of the one or more placental protein in the sample, comparing the amount to a respective threshold level or value, such as a predetermined threshold level, for the placental protein based on a predetermined GA cutpoint. In some embodiments, the gestational age of the subject is determined to be above a predetermined cutpoint GA if the amount (e.g. concentration) of one or more of the one or more placental proteins is equal to or above its respective predetermined threshold level, or the subject is determined to be below a predetermined cutpoint GA if the amount (concentration) of one or more of the one or more placental proteins is below its respective predetermined threshold level.

In some embodiments, the provided methods can be used for differentiating pregnancies of less than the predetermined cutpoint GA from later pregnancies. In some embodiments, the provided methods can be used to classify a subject as having a GA below a predetermined GA cutpoint (negative test) or as having a GA above a predetermined GA cutpoint (positive test). In some embodiments, a positive test result can be used to determine if a subject is eligible or ineligible for a particular or certain prenatal care or clinical decision or treatment. In other embodiments, a negative test result can be used to determine if a subject is eligible or ineligible for a particular or certain prenatal care or clinical decision or treatment.

The provided embodiments offer an assay to reliably assess whether pregnancy has (or has not) progressed beyond a particular GA of clinical interest. In some aspects, such methods offer advantages to previous attempts to estimate GA using tests from biological samples. Development of a serum or urine test to produce an estimate of GA that is accurate and precise across the entire course of gestation is believed to be challenging because of inter-individual variation in production of the target substrate, particularly in later pregnancy (Naiem et al. (1988) Br J Obstet Gynaecol, 95:116-9; Bersinger et al. (1986) Gynecol Obstet Invest, 21:113-6). The provided methods, however, provide a test that produces a binary result to distinguish GA above and below a specified limit. Accordingly, the provided methods are easy to perform, simple to interpret and inexpensive. Likewise, the inventors herein have surprisingly discovered that certain serum biomarkers, such as PAPP-A, provide the ability to continuously predict GA across different times.

The provided methods are based on observations that the amount (e.g. concentration) of certain placental proteins in serum samples are indicative of GA as determined by ultrasound, which is the current clinical reference standard. Thus, provided methods based on measuring serum concentrations of placental proteins could obviate the need for ultrasound for determining GA, including in connection with making a prenatal care or prenatal clinical treatment decisions, for example before early aspiration or outpatient medical abortion. The provided methods also are beneficial, since an ultrasound is expensive, time-consuming, must be performed by a trained technician, and is usually available only in specialized medical facilities. A cheaper, less technical tool to assess GA could be highly beneficial, particularly in low resource environments or when providing services through telemedicine.

In addition, the determination of GA is integral to every decision made in obstetric care, including timing of evaluations (such as tests for maternal diabetes or fetal anomalies, assessment of fetal viability and growth), treatments (such as Rh Ig administration and other preventive therapies), timing of delivery and preparation for that event, and eligibility for abortion. Knowledge of GA is also relevant to multiple life decisions that a pregnant person may make over the course of the pregnancy (whether to seek an abortion, take a trip, expend money for the anticipated baby, get married, etc.). The methods provided herein provide accurate ways of determining GA, and doing so without the need for ultrasound or a specialized medical facility.

The provided methods are based on findings that serum concentrations of certain placental proteins can be used to determine or predict GA of a pregnant subject, or whether a GA is above or below a certain GA cutpoint. In particular, findings herein demonstrate that PAPP-A exhibits a high sensitivity and specificity for identifying subjects with a GA above or below a GA cutpoint, particularly for identifying GA>70 days, which is the currently accepted eligibility limit for receiving a medical abortion, such as treatment with mifepristone and misoprostol. The high sensitivity and specificity of PAPP-A can obviate the need for dating ultrasounds, particularly within the eligible GA range for a particular prenatal care or prenatal clinical treatment, while providing assurance that ineligible people will not inadvertently be treated. Serum concentrations of PAPP-A also is shown herein to be a continuous predictor of different GA timepoints. Serum concentrations of other biomarkers, particularly ADAM-12, also are shown to exhibit utility as a serum marker for predicting GA or whether a GA is above or below a certain GA cutpoint. The data also demonstrate that sensitive and specific serum tests are also possible using other placental protein markers or other GA cutpoints based on a particular prenatal care or prenatal care treatment. For example, data demonstrate that concentration thresholds for PAPP-A, ADAM-12, PSG1 (SP1), and HPL have high sensitivity and specificity for distinguishing GAs above and below 15 weeks (105 days), which could help guide obstetric and abortion care in the early second trimester as well as other pregnancy-related decisions.

In provided embodiments, the amount (e.g., concentration) of a placental protein can be used to classify a predetermined GA cutpoint based on a defined or predetermined threshold level of the respective placental biomarker. The particular choice of predetermined threshold level for classifying GA can depend on the particular purpose of the test and the desired specificity, sensitivity and/or accuracy of the test. Likewise, the exact GA cutpoint across a pregnancy can be dependent on the particular clinical endpoint or need, such as the particular prenatal care or prenatal clinical treatment that is desired or is being evaluated for a pregnant subject. For example, a predetermined GA cutpoint that is at or about 10 weeks (70 days) can distinguish pregnancies of <10 weeks from later gestations. A 10-week GA is the currently accepted eligibility limit for treatment with mifepristone and misoprostol. Thus, the provided methods can be used to identify subjects that do not meet the eligibility limit GA>70 days to thereby identify or select those subjects that are eligible for a medical abortion, such as whether a pregnant subject is eligible for treatment with mifepristone and misoprostol. This GA cutpoint at the end of embryogenesis may be relevant for a variety of clinical or prenatal care decisions. In some embodiments, such a test would be useful for assessing eligibility for early aspiration or outpatient medical abortion. Furthermore, since embryotoxicity is of primary concern within the first 8-10 weeks of gestation, a test that reliably identifies pregnancies that have progressed beyond that point may be helpful in assessing risk from potentially dangerous exposures. Exact dating of early pregnancy may be useful in legal cases or for anyone whose early pregnancy is of unknown duration. The test may also be useful for determining when a patient is eligible for certain prenatal screening tests conducted at 10 weeks or later, such as screening tests for trisomy 21 (Down syndrome).

In other provided embodiments, the amount (e.g. concentration) of a placental protein can be used to be used to predict GA across different time points as a continuous predictor across a range or band of different GAs. In provided embodiments, after determining the amount (e.g. concentration) of the one or more placental protein in the sample, the methods can include predicting the gestational age of the pregnancy based on the measured amount (e.g. concentration) for the placental protein by providing the amount (e.g. concentration) as input to a process (e.g. regression model) that uses the amount (e.g. concentration) of the placental protein as a continuous predictor of gestational age. For example, findings herein demonstrate that there is a relationship of serum concentration of certain placental biomarkers, such as PAPP-A, with gestational age, such that it is possible to continuously predict gestational age at different points of time within a band or range of different gestational ages. In some embodiments, a prenatal care or prenatal clinical treatment can be selected based on the predicted gestational ages for the placental protein or a combination of placental protein markers. Predicting GA with a serum marker can be beneficial to deciding if a patient is eligible for or can receive any of a variety of prenatal care or prenatal clinical treatments.

In some embodiments, the methods can be carried out by a skilled practitioner, such as in a laboratory. In some embodiments, the methods can be applied as a point-of-care test, such that it could be used at home to guide many personal decisions once pregnancy occurs. In some embodiments, the methods can include one or more additional test with ultrasound or other clinical measure to verify GA.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, gestational age (GA) refers to weeks or days of human development timed from fertilization to the current date, plus 14 days. A normal pregnancy can range from 38 to 42 weeks.

As used herein, "antibody" refers to immunoglobulins and immunoglobulin fragments, whether natural or partially or wholly synthetically, such as recombinantly, produced, including any fragment thereof containing at least a portion of the variable heavy chain and/or light chain region of the immunoglobulin molecule that is sufficient to form an antigen binding site and, when assembled, to specifically bind antigen. Hence, an antibody includes any protein having a binding domain that is homologous or substantially homologous to an immunoglobulin antigen-binding domain (antibody combining site). Typically, antibodies minimally include all or at least a portion of the variable heavy ($V_H$) chain and/or the variable light ($V_L$) chain. In general, the pairing of a $V_H$ and $V_L$ together form the antigen-binding site, although, in some cases, a single $V_H$ or $V_L$ domain is sufficient for antigen-binding. The antibody also can include all or a portion of the constant region. Hence, it is understood that reference to an antibody herein includes full-length antibody and antigen-binding fragments, including those that specifically bind to a respective placental protein as described. Antibodies include polyclonal antibodies or monoclonal antibodies. Antibody also includes synthetic antibodies or recombinantly produced antibodies. The term "immunoglobulin" (Ig) is used interchangeably with "antibody" herein.

Thus, the term antibody includes full-length antibodies and portions thereof including antibody fragments, wherein such contain a heavy chain or portion thereof and/or a light chain or portion thereof. An antibody can contain two heavy chains (which can be denoted H and H') and two light chains (which can be denoted L and L'). Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains (CH1, CH2 and CH3) for each of the α and γ chains and four $C_H$ domains (CH1, CH2, CH3 and CH4) for μ and ε isotypes. Each L chain has at the N-terminus, a variable domain ($V_L$) followed by a constant domain ($C_L$) at its other end. In some cases, the heavy chain can be a full-length immunoglobulin heavy chain or a portion thereof sufficient to form an antigen binding site (e.g., heavy chains include, but are not limited to, VH chains, VH-CH1 chains and VH-CH1-CH2-CH3 chains), and/or each light chain can be a full-length light chain or a portion thereof sufficient to form an antigen binding site (e.g., light chains include, but are not limited to, VL chains and VL-CL chains). For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, CT, 1994, page 71 and Chapter 6. Each heavy chain (H and H') pairs with one light chain (L and L', respectively).

The terms "full-length antibody," "intact antibody" or "whole antibody" are used interchangeably to refer to an antibody in its substantially intact form, as opposed to an antibody fragment. A full-length antibody is an antibody typically having two full-length heavy chains (e.g., VH-CH1-CH2-CH3 or VH-CH1-CH2-CH3-CH4) and two full-length light chains (VL-CL) and hinge regions, such as antibodies produced from mammalian species (e.g. human, mouse, rat, rabbit, non-human primate, etc.) by antibody secreting B cells and antibodies with the same domains that are produced synthetically. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, the antigen binding and/or the variable region of the intact antibody. Antibody fragments, include, but are not limited to, Fab fragments, Fab' fragments, F(ab')$_2$ fragments, Fv fragments, disulfide-linked Fvs (dsFv), Fd fragments, Fd' fragments; diabodies; linear antibodies (see U.S. Pat. No. 5,641,870, Example 2; Zapata et al., Protein Eng. 8(10): 1057-1062 [1995]); single-chain antibody molecules, including single-chain Fvs (scFv) or single-chain Fabs (scFab); antigen-binding fragments of any of the above and multispecific antibodies from antibody fragments.

A "monoclonal antibody" (mAb) refers to a homogeneous antibody population wherein the monoclonal antibody is comprised of amino acids (naturally occurring and non-naturally occurring) that are involved in the selective binding of an epitope. In particular, the CDRs of the monoclonal antibody are identical in all the molecules of the population. MAbs contain an antigen binding site capable of immunoreacting with a particular epitope of the antigen characterized by a unique binding affinity for it. The term "monoclonal antibody" encompasses not only intact monoclonal antibodies and full-length monoclonal antibodies, but also fragments thereof as described above.

As used herein, the terms "specific binding," or "specifically binds" is the ability of a binding molecule, such as an antibody or an antigen-binding fragment, to preferentially bind an antigen in a complex mixture of proteins and/or macromolecules. A binding molecule is said to exhibit "specific binding" or "preferential binding" if it reacts or associates more frequently, more rapidly, with greater duration and/or with greater affinity with a particular cell or target antigen than it does with alternative cells or target antigens. A binding molecule specifically binds or preferentially binds to a target if it binds with greater affinity, avidity, more readily, and/or with greater duration than it binds to other substances. In some aspects, specific binding can refer to the non-covalent interactions of the type that occur between an immunoglobulin molecule and an antigen for which the immunoglobulin is specific. It is understood that specific binding or preferential binding does not necessarily require (although it can include) exclusive binding. Various known methods can be used to quantify or assess binding. The strength, or affinity of binding interactions can be expressed in terms of the dissociation constant ($K_d$) of the interaction, wherein a smaller $K_d$ represents a greater affinity. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity and is equal to the dissociation constant $K_d$. (See, generally, Davies et al. (1990) Annual Rev Biochem 59:439-473). A binding molecule, such as an antibody or antigen binding fragment, is said to specifically bind, when the binding constant ($K_d$) is ≤1 µM, for example, in some embodiments ≤100 nM, in some embodiments ≤10 nM, and in some embodiments ≤100 pM to about 1 pM, as measured by assays such as radioligand binding assays or similar assays known to those skilled in the art.

As used herein, detection includes methods that permit visualization (by eye or equipment) of a protein. A protein can be visualized using an antibody specific to the protein. Detection of a protein can also be facilitated by fusion of a protein with a tag including an epitope tag or label.

The term "label" means any moiety which can be attached or linked, directly or indirectly, to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

As used herein, a "solid phase binding assay" refers to an in vitro assay in which an antigen is contacted with a ligand, where one of the antigen or ligand are bound to a solid support. Upon antigen-ligand interaction, the unwanted or non-specific components can be removed (e.g. by washing) and the antigen-ligand complex detected.

By "solid support" is meant a non-aqueous matrix to which an antibody according to the provided disclosure can adhere or attach. For example, solid supports include, but are not limited to, a microtiter plate, a membrane (e.g., nitrocellulose), a bead, a dipstick, a thin-layer chromatographic plate, or other solid medium.

The term "composition" refers to any mixture of two or more products, substances, or compounds, including antibodies. It may be a solution, a suspension, liquid, powder, a paste, aqueous, non-aqueous or any combination thereof. The preparation is generally in such form as to permit the biological activity of the active ingredient (e.g. antibody) to be effective.

As used herein, combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, a kit is a packaged combination that optionally includes other elements, such as additional reagents and instructions for use of the combination or elements thereof, for a purpose including, but not limited to, detection, diagnosis, and/or assessment of a biological activity or property.

As used herein, an "article of manufacture" is a product that is made and sold. As used throughout this application, the term is intended to encompass any of the antibodies provided herein, including compositions and combinations thereof, contained in articles of packaging.

II. PLACENTAL PROTEIN BIOMARKERS AND METHODS

Provided herein are methods for classifying or determining gestational age of a subject comprising the steps of (a)

determining, quantitating, or measuring the amount (e.g., concentration) of one or more placental protein markers selected from ADAM-12, PAPP-A, PSG1 (SP1), or HPL, from a sample, for instance a serum sample, from a pregnant subject, (b) comparing the amount (e.g., concentration) to a respective predetermined threshold level for the placental protein, and (c) determining if the gestational age of the pregnancy is greater than or equal to a predetermined GA cutpoint, thereby classifying the gestational age as greater than or equal to the predetermined GA cutpoint or less than the predetermined GA cutpoint. Also provided herein are methods for predicting the gestational age of a subject comprising the steps of (a) determining, quantitating, or measuring the amount (e.g., concentration) of one or more placental protein markers selected from ADAM-12, PAPP-A, PSG1 (SP1), or HPL, from a sample, for instance a serum sample, from a pregnant subject, and (b) providing the amount (e.g., concentration) as input to a process that uses the amount (e.g., concentration) as a continuous predictor of gestational age. In some embodiments, the method is carried out on 1, 2, 3, or all 4 of the placental protein markers. In some embodiments, the methods provided herein comprise further steps of performing a selected prenatal treatment on the subject.

In some embodiments, the one or more placental proteins is or includes Human Pappalysin-1 (PAPP-A). Human PAPP-A is synthesized as a prepro-precursor that contains a 22 aa signal sequence, a 58 aa pro-segment, and a 1548 aa mature region (e.g. GenBank No. NP_002572.2). PAPP-A is a 400 kDa secreted, homodimeric glycoprotein that belongs to the metzincin superfamily of metalloproteases. As a secreted metalloproteinase, active PAPP-A cleaves insulin-like growth factor binding proteins (IGFBPs) resulting in dissociation of insulin growth factors to bind and activate IGF receptors to regulate fetal growth and development.

In some embodiments, the one or more placental proteins is or includes human A Disintegrin And Metalloproteinase domain-containing protein 12 (ADAM-12). ADAM-12 (e.g. GenBank No. AF023477) is a metalloproteinase and is synthesized as a preproprotein and requires proteolytic cleavage of the pro-domain before it is transported to the cell surface and secreted as an active form. ADAM-12 is highly expressed in placenta and, among its activities as an active metalloprotease, ADAM-12 is believed to have proteolytic activity against IGFBP-3 to regulate insulin growth factor bioavailability.

In some embodiments, the one or more placental proteins is or includes human Pregnancy-Specific beta-1-Glycoprotein 1 (PSG1; previously known as SP1). PSG1 (e.g. Genbank No. NP_001171754.1) is a member of the immunoglobulin superfamily of proteins. PSG1 is highly expressed in the maternal plasma during pregnancy. It is produced by syncytiotrophoblast cells beginning with their differentiation from villous cytotrophoblast cells and has been detected in the maternal serum as early as 3 days postfertilization. PSG-1 is believed to act as an immunomodulatory protein, including to induce production of anti-inflammatory cytokines such as transforming growth factor beta 1 (TGFB1). Such activity may contribute to preventing rejection of the allogeneic fetus by the maternal immune system.

In some embodiments, the one or more placental proteins is or includes Human Placental Lactogen (HPL). hPL is also known as chorionic somatomammotropin hormone 1 or choriomammotropin lactogen. hPL (e.g. GenBank No. NP_001308) is a member of the somatotropin/prolactin family of hormones and is secreted by the syncytiotrophoblast during pregnancy. As a hormone, it acts to modify the metabolic state of the mother during pregnancy to facilitate the energy supply of the fetus. The mature protein is contains single chain of 191 amino acid residues that are linked by two disulfide bonds.

In embodiments of the provided methods, the method involves at least a first assay for measuring a first placental protein in a sample (e.g. serum) from among ADAM-12, PAPP-A, PSG1 (SP1), or HPL, and at least a second assay for measuring a second placental protein from the sample (e.g. serum) from among another or different placental protein from ADAM-12, PAPP-A, PSG1 (SP1), or HPL. In some embodiments, 2, 3, or 4 or more proteins are measured.

In some embodiments, the first and second assay or additional assays are carried out based on the same predetermined GA cutpoint. In such methods, a combined test can be used to increase the sensitivity, specificity and/or accuracy of the results. In some embodiments, each of the assessed or measured proteins is compared to the same predetermined GA cutpoint, thereby determining for each of the placental proteins if the gestational age of the pregnancy is predicted to be greater than or equal to a predetermined GA cutpoint or less than the predetermined GA cutpoint. In some embodiments, a subject is classified as having a pregnancy with a GA below a predetermined GA cutpoint if each of the assessed or measured placental proteins is below the predetermined threshold level for the respective biomarker (negative test) or a subject is classified as having a pregnancy with a GA at or above a predetermined GA cutpoint if each of the assessed or measured placental proteins is at or above the predetermined threshold level for the respective biomarker.

In some embodiments, the first and second assay or additional assays are carried out based on different predetermined GA cutpoints. In some embodiments, each of the first and second assay or additional assays are carried out based on the same placental protein but at different predetermined threshold levels. In some embodiments, each of the first and second assay or additional assays are carried out based on the different placental protein with respective predetermined threshold levels for a given GA cutpoint. In such methods, a combined test could set different thresholds for various GAs, depending on clinical need. Further, by combining tests with different thresholds, one could create an algorithm that classifies GA within categories.

In some embodiments, the GA of the subject is predicted using the results of the first and second assay or additional assays are carried out. In such methods, a combined test can be used to increase the sensitivity, specificity and/or accuracy of the results. In some embodiments, each of the assessed or measured protein amounts is provided as input to a separate process that uses the protein amount as a continuous predictor of GA. In some embodiments, all assessed or measured protein amounts are provided as input to a single process that uses all of the protein amounts as continuous predictors of GA.

In some embodiments, the methods can further include selecting or screening a subject for a certain prenatal care, clinical treatment or other decision or action based on results of the gestational age assessment. In some embodiments, the methods also can include carrying out the prenatal care, clinical treatment or other decision or action on the female subject based on the selection or screening results. In some embodiments, the prenatal care, clinical treatment or other decision or action is carried out if the subject has been classified as having a gestational age lower than the predetermined GA cutpoint. In some embodiments, the prenatal care, clinical treatment or other decision or action is carried out if the subject has been classified as having a gestational age higher than the predetermined GA cutpoint.

A. Immunoassays

In some embodiments, the provided methods involve immunoaffinity-based detection of the one or more placental proteins using an immunoassay. In some embodiments, the methods are performed in vitro. In some embodiments, the sample is obtained or isolated from the subject or individual. In some embodiments, the subject or individual is a human.

In some embodiments, methods of measuring the concentration of the one or more placental protein using an immunoassay includes the steps of (a) contacting a sample (e.g. serum) from the subject with one or more antibody that specifically binds to the one or more placental protein; and (b) determining, quantifying or measuring the amount of the one or more placental protein in the sample (e.g. serum) by assessing the amount of the one or more placental protein bound by the one or more antibody. In some embodiments, the contacted is carried out under conditions to form a complex comprising the antibody or antigen-binding fragment and its antigen (e.g. the one or more placental protein). In some embodiments, the immunoassay can be an enzyme linked immunosorbent assay (ELISA) or other similar immunoassay, including a sandwich ELISA or competitive ELISA; immunohistochemistry (IHC); flow cytometry, or western blot.

In some embodiments, the sample is serum, plasma, or blood (e.g., whole blood) sample present or obtained from an individual (e.g., human) that is pregnant or suspected of being pregnant.

In some embodiments, the sample is serum. The sample can be used directly in the methods provided herein after obtaining it from an individual or it can be processed before use in the methods provided herein. Processing of the sample includes techniques commonly used in the art to purify and/or concentrate a protein sample such as washing in a buffer, incubation, centrifugation, filtration, immunoprecipitation, adsorption and/or addition of agents that remove contaminants that can interfere with detecting the binding between antigen (e.g. one or more placental protein) and an antibody.

In some embodiments, the method is a sandwich or competitive immunoassay (e.g. sandwich ELISA or a competitive ELISA assay) and the method comprises (a) contacting a sample from the subject with one or more first antibody (e.g. capture antibody) to capture or bind the one or more placental protein in the sample (e.g., under conditions to form a complex comprising the antibody or antigen-binding fragment and the protein); and (b) detecting the bound protein in the sample by adding one or more second antibody (e.g. detection antibody) to detect the presence or absence of the one or more placental protein in the sample or associated with the complex. In some embodiments, one or more second antibody is directly or indirectly labeled for detection or is capable of detection. In some embodiments, the capture antibody is a monoclonal antibody. In some embodiments, the detection antibody is a monoclonal antibody or a polyclonal antibody. In some embodiments, the first antibody is different than the second antibody, such as binds to a distinct or non-overlapping epitope compared to the second antibody and/or does not compete for binding to the protein with the second antibody. In some embodiments, the second antibody is directly or indirectly labeled for detection. In some embodiments, the first and second antibody can be part of an antibody pair for use in determining, quantifying or measuring the one or more placental protein in the sample.

In an exemplary method, one or more first antibody that is generally unlabeled is first immobilized to a solid support (e.g. coated to wells of a microtiter plate), followed by incubation with a fluid sample containing or potentially containing the placental protein (e.g. serum) to capture any placental protein in the sample, for example, under conditions to form a complex of the first antibody and the placental protein. In some cases, the first antibody can be labeled with a reagent to facilitate its immobilization on the solid phase. In one example, the first antibody is labeled with biotin and the solid phase has immobilized thereon or is coated with a biotin-binding reagent, such as streptavidin. After washing the fluid sample with an appropriate buffer, the complex containing bound placental protein can be contacted with one or more second antibody that is labeled (e.g. HRP-conjugated antibody) to bind to the placental protein formed in a complex with the first antibody on the solid support. Following removal of the unbound labeled second antibody, the bound labeled antibody or antibodies is detected directly or by using a detection reagent.

In some embodiments, a detection antibody used in an immunoassay for determining, measuring or quantitating an amount (e.g. concentration) of a placental protein can be conjugated directly or indirectly to a moiety that is capable of detection. In some examples, one or more of the antibodies are modified to permit detection of binding. For example, antibodies can be conjugated to a detectable molecule that permits either direct detection or detection via secondary agents. In some embodiments, antibodies are directly labeled. In some examples, the antibodies can be detected using a secondary reagent, such as by a secondary antibody reagent that binds to a primary antibody and that is coupled to a detectable protein, such as a fluorescent probe or detectable enzyme, such as horseradish peroxidase. For example, in one non-limiting example, the the second antibody can be labeled with an HRP label of and can be detected by the addition of a detection substrate, such as ABTS (2,2'-Azinobis [3-ethylbenzothiazoline-6-sulfonic acid]-diammonium salt), OPD (o-phenylenediamine dihydrochloride) or TMB (3,3',5,5'-tetramethylbenzidine) detection substrate. Other detection reagents suitable for use with particular detectable labels are well known to a skilled artisan.

In some embodiments, the sample from the subject can be assessed for the presence, absence or amount of the one or more placental protein using a solid-phase binding assay. Solid-phase binding assays can detect a protein (e.g. placental protein) in a fluid sample by binding of the protein to a binding agent (e.g. a capture antibody) that is fixed or immobilized to a solid surface. In some embodiments, the contacting comprises adding the sample (e.g., serum sample) to a solid support or a device comprising a solid support, wherein the solid support comprises the first antibody (e.g. capture antibody). In some embodiments, the contacting of the sample on the solid support is carried out under conditions to form a complex comprising the antibody or antigen-binding fragment and the protein (e.g. placental protein). In some embodiments, the sample is mixed with the one or more antibody in the presence of or on or in a solid support or a device comprising a solid support. In some embodiments, the sample is mixed with the one or more antibody to produce a mixture and the mixture is subsequently applied to a solid support or a device comprising a solid support. In some of the embodiments herein, the one or more antibody is directly or indirectly attached to the solid support. In some embodiments, the sample and the one or more capture antibody are incubated under conditions to form a complex containing the antibody and protein. The incubation can be for a time that is suitable to allow the sample to contact the one or more antibody such as for at least or at least about 30 seconds, 1 minute, 5 minutes, 10 minutes, 15 minutes, 20 minutes, 30 minutes, 45 minutes, 1 hour, 2 hours, 3 hours, 6 hours, or 12 hours or more but no more than about 24 hours after contacting a sample with the one or more antibody. In some embodiments, the contacting occurs at a temperature of from or from about 0° C. to about 50° C., such as typically 2° C. to 8° C. or 23° C. to 28° C. or 37° C. to 42° C. In some embodiments, after the contacting, the method can include one or more washing under conditions to retain bound protein (e.g. one or more placental protein) on the solid support and/or to separate or remove any unbound reagents or proteins of the sample not part of the complex and/or that were not specifically bound by the antibody.

In some embodiments, the second antibody is a naked (unlabeled) antibody specific for the one or more placental protein and detection is indirect by adding a labeled secondary antibody that binds to the naked antibody. In some embodiments, the second antibody is a labeled antibody specific for the one or more placental protein and detection is direct. In some embodiments, the second antibody is a labeled antibody but it not capable of direct detection. For example, the label can be an enzyme and detection can be effected by addition of a substrate that produces a signal, e.g. a colorimetric signal. In some embodiments, the second antibody (detection antibody) is applied or contacted with the bound placental protein in the complex formed with the first antibody (e.g. capture antibody), and allowed to incubate under conditions to allow binding of the second antibody to the bound protein (e.g. the one or more placental protein) in the complex. In some embodiments, the incubations can be for a time that is suitable to allow the second antibody (detection antibody) to contact the bound placental protein in the complex with the first antibody, such as for at least or at least about 30 seconds, 1 minute, 5 minutes, 10 minutes, 15 minutes, 20 minutes, 30 minutes, 45 minutes, 1 hour, 2 hours, 3 hours, 6 hours or 12 hours or more but no more than about 24 hours after contacting a sample with the second antibody. In some embodiments, the contacting occurs at a temperature of from or from about 0° C. to about 30° C., such as typically 2° C. to 8° C. or 23° C. to 28° C. In some embodiments, after the contacting with the second antibody, the method can further include one or more washing steps under conditions to retain binding of the second antibody to the bound substrate or complex and to remove any unbound second antibody.

In some embodiments, the presence, such as signal, of the second antibody is then detected. Detection methods include, but are not limited to, colorimetric, fluorescent, luminescent or radioactive methods. The choice of detection method is dependent on the detectable label used. In some examples, a colorimetric reaction is used in which the antibody is coupled to an enzyme, such as horseradish peroxidase (HRP), alkaline phosphatase or other detectable enzyme.

In some embodiments, the method further includes determining or quantitating the amount of the one or more placental protein in the sample. In some such aspects, the amount of protein present in the sample is proportional to the amount of signal, e.g. color, produced. Methods for quantification of signals are well known in the art such as through use of a luminometer, spectrophotometer, or a digital imaging instrument. In some embodiments, a substrate standard is generally employed to quantitate or determine the amount of protein (e.g. placental protein) in the sample. In some embodiments, the standard comprises known concentrations (e.g. serial dilutions) of a recombinant or native form of the protein. In some embodiments, the amount of protein (e.g. placental protein) in a sample can be calculated as a relative amount by interpolating the data to the standard curve. In some embodiments, the amount of the one or more placental protein can be expressed as a concentration of fluid sample. Quantifying the amount of a placental protein may be the absolute quantity, in mass per unit volume, moles (e.g. nano moles) per unit volume or as international units per unit volume. In one embodiment the method employed is semi-quantitative.

In some embodiments, the immunoassay is one that has an assay range for detection of the placental protein in the sample (e.g. serum sample). In some embodiments, the assay has a range of detection (lower limit of detection to upper level of detection) of 0.100-1000000 mIU/mL. In some embodiments, the assay has a range of detection (lower limit of detection to upper level of detection) of 0.0000001-100 mg/L or any range between any of the foregoing. In some cases, the assay range can be given as an International Unit (IU) which is a unit of measurement for the amount of a substance based on a known biological activity or effect. In some embodiments, the assay has a range of detection (lower limit of detection to upper level of detection) of 0.100-10000 mIU/mL or any range between any of the foregoing. A skilled artisan knows or can determine the assay range of an immunoassay, such as by determining the range that corresponds to a linear portion of a standard curve to ensure the analyte concentration can be determined accurately. In embodiments of the provided methods, the concentration of the protein in the sample should be greater than the lower limit of detection and lower than the upper level of detection. In some aspects, the sample can be diluted with a diluent to achieve a concentration within the assay range. It is within the level of a skilled artisan to empirically determine the appropriate dilution of a sample depending on the particular assay being used. In some embodiments, the sample is diluted by at or about or 2-fold, 3-fold, 4-fold, 5-fold, 10-fold, 20-fold, 50-fold, 100-fold, 200-fold or more.

In some embodiments, the provided methods include determining, quantitating or measuring the amount (e.g. concentration) of PAPP-A in a sample (e.g. serum sample) using an immunoassay, such as a sandwich or competitive immunoassay (e.g. sandwich ELISA or a competitive ELISA assay). In some aspects, the step of measuring includes (a) contacting a sample from the subject with one or more first antibody to capture or bind the PAPP-A in the sample, such as under conditions to form a complex comprising the antibody or antigen-binding fragment and PAPP-A, and then carrying out one or more optional wash steps; (b) contacting the sample or complex containing the bound PAPP-A with one or more second antibody, and then carrying out one or more optional wash steps; and (c) determining or quantifying the amount of PAPP-A bound by the one or more second anti-PAPP-A antibody. In some embodiments, the amount of PAPP-A is determined by comparison of the detectable signal to a standard curve, such as a standard curve comprising a series of known concentrations of a recombinant or native PAPP-A. In some embodiments, the immunoassay has an assay range, e.g. linear range, of between at or about 0.5 ng/mL and at or about 100 ng/mL, such as between at or about 0.781 ng/mL and at or about 50.0 ng/mL. Antibodies and immunoassays for PAPP-A are known and include commercial assays and kits for detecting PAPP-A. Exemplary monoclonal antibodies for detecting human PAPP-A through immunoassay include, for example, clone 10A5 Abnova (Abnova; Catalog No. MAB0583), clone 10E1 (Abnova; Catalog No. MAB0570), clone 10E2 (Abnova; Catalog No. MAB0580), clone 10H9 (Abnova; Catalog No. MAB0585), clone 11E4 (Abnova, Catalog No. MAB0587), clone 18A10 (Abnova, Catalog No. MAB0586), clone 3C8 (Abnova, Catalog No. MAB0584), clone 4G11 (Abnova, Catalog No. MAB0582), clone 5H9 (Abnova, Catalog No. MAB0581), clone 242011 (R & D systems; Catalog No. MAB1668); monoclonal mouse anti-human pregnancy-associated plasma protein (PAPP-A) from HyTest (Catalog No. 4P41), or monoclonal mouse anti-human pregnancy-associated plasma protein (PAPP-A) from LSBio (Catalog No. LS-C141880). Exemplary immunoassays include, for example, the human Pappalysin-1/PAPP-A Immunoassay from R&D Systems (Catalog No. DPPA00), human PAPP-A Immunoassay from RayBio (Catalog No. ELH-PAPPA-A), human PAPP-A Immunoassay from Abcam (Catalog No. ab235647), human PAPP-A Immunoassay from ThermoFisher Scientific (Catalog No. EHPAPPA), human PAPP-A Immunoassay from MyBiosource (Catalog No. MBS268731), human PAPP-A Immunoassay from SigmaAldrich (Catalog No. RAB0720), human PAPP-A Immunoassay from LSBio (Catalog No. LS-F12256-1).

In some embodiments, the provided methods include determining, quantitating or measuring the amount (e.g. concentration) of ADAM-12 in a sample (e.g. serum sample) using an immunoassay, such as a sandwich or competitive immunoassay (e.g. sandwich ELISA or a competitive ELISA assay). In some aspects, the step of measuring includes (a) contacting a sample from the subject with one or more first antibody to capture or bind the ADAM-12 in the sample, such as under conditions to form a complex comprising the antibody or antigen-binding fragment and ADAM-12, and then carrying out one or more optional wash steps; (b) contacting the sample or complex containing the bound ADAM-12 with one or more second antibody, and then carrying out one or more optional wash steps; and (c) determining or quantifying the amount of ADAM-12 bound by the one or more second anti-ADAM-12 antibody. In some embodiments, the amount of ADAM-12 is determined by comparison of the detectable signal to a standard curve, such as a standard curve comprising a series of known concentrations of a recombinant or native ADAM-12. In some embodiments, the immunoassay has an assay range, e.g. linear range, of between at or about 0.1 ng/mL and at or about 50 ng/mL, such as between at or about 0.312 ng/mL and at or about 20.0 ng/mL. Immunoassays for ADAM-12 are known and include commercial assays and kits for detecting ADAM-12. Exemplary monoclonal antibodies for detecting human ADAM-12 through immunoassay include clone 1G3 (LSBio, Catalog No. LS-C198523 or Abnova, Catalog No. H00008038-M01) or clone 632525 (R&D Systems Catalog No. MAB44161). An exemplary polyclonal antibody for detecting human ADAM-12 through immunoassay includes clone B01 (Abnova, Catalog No. H00008038-B01). Exemplary immunoassays include the Human ADAM-12 Immunoassay from R&D Systems (Catalog No. DAD120), Human ADAM-12 Immunoassay from Abcam (Catalog No. ab171346), Human ADAM-12 Immunoassay from SigmaAldrich (Catalog No. RAB1248), Human ADAM-12 Immunoassay from MyBiosource (Catalog No. MBS704578), Human ADAM-12 Immunoassay from LSBio (Catalog No. LS-F10738-1), Human ADAM-12 Immunoassay from Rockland Inc. (Catalog No. KOA0569) and the immunoassay using ADAM-12 (Human) Matched Antibody Pair from Abnova (Catalog No. H00008038-AP51).

In some embodiments, the provided methods include determining, quantitating or measuring the amount (e.g. concentration) of PSG1 in a sample (e.g. serum sample) using an immunoassay, such as a sandwich or competitive immunoassay (e.g. sandwich ELISA or a competitive ELISA assay). In some aspects, the step of measuring includes (a) contacting a sample from the subject with one or more first antibody to capture or bind the PSG1 in the sample, such as under conditions to form a complex comprising the antibody or antigen-binding fragment and PSG1, and then carrying out one or more optional wash steps; (b) contacting the sample or complex containing the bound PSG1 with one or more second antibody, and then carrying out one or more optional wash steps; and (c) determining or quantifying the amount of PSG1 bound by the one or more second anti-PSG1 antibody. In some embodiments, the amount of PSG1 is determined by comparison of the detectable signal to a standard curve, such as a standard curve comprising a series of known concentrations of a recombinant or native PSG1. In some embodiments, the immunoassay as an assay range, e.g. linear range, of between at or about 1 ng/mL and at or about 500 ng/mL, such as between at or about 3.13 ng/mL and at or about 200 ng/mL. Immunoassays for PSG1 are known and include commercial assays and kits for detecting PSG1. Exemplary monoclonal antibodies for detecting human PSG1 through immunoassay include clone 684701 (R&D Systems, Catalog No. MAB6799), and clone 5C6G7 (Abnova, Catalog No. MAB21345). Exemplary immunoassays include the Human PSG1 Immunoassay from R&D Systems (Catalog No. DPSG10), Human PSG1 Immunoassay from LSBio (Catalog No. LS-F16359-1), Human PSG1 Immunoassay from MyBioSource (Catalog No. MBS720765), Human PSG1 Immunoassay from Abcam (Catalog No. ab243676), Human PSG1 Immunoassay from (Catalog No. ab243676.

In some embodiments, the provided methods include determining, quantitating or measuring the amount (e.g. concentration) of HPL in a sample (e.g. serum sample) using an immunoassay, such as a sandwich or competitive immunoassay (e.g. sandwich ELISA or a competitive ELISA assay). In some aspects, the step of measuring includes (a) contacting a sample from the subject with one or more first antibody to capture bind the HPL in the sample, such as under conditions to form a complex comprising the antibody or antigen-binding fragment and HPL, and then carrying out one or more optional wash steps; (b) contacting the sample or complex containing the bound HPL with one or more second antibody, and then carrying out one or more optional wash steps; and (c) determining or quantifying the amount of HPL bound by the one or more second anti-HPL antibody. In some embodiments, the amount of HPL is determined by comparison of the detectable signal to a standard curve, such as a standard curve comprising a series of known concentrations of a recombinant or native HPL. In some embodiments, the immunoassay as an assay range, e.g. linear range, of between at or about 0.1 mg/L and at or about 50 mg/L, such as between at or about 0.04 mg/L and at or about 20.0 mg/L. Immunoassays for HPL are known and include commercial assays and kits for detecting HPL. Exemplary monoclonal antibodies for detecting human hPL through immunoassay include clone 658230 (R & D systems; Catalog No. MAB5757). Exemplary immunoassays include the Human Placental Lactogen (HPL) ELISA from ALPCO (Catalog No. 20-HPLHU-E01), Human Placental Lactogen (HPL) ELISA from MyBioSource (Catalog No. MBS039402), Human Placental Lactogen (HPL) ELISA from Cusabio (Catalog No. CSB-E09665h), and Human Placental Lactogen (HPL) ELISA from OriGene (Catalog No. EA101020).

B. Placental Protein Thresholds and Gestational Age Cutpoint

The provided methods include comparing a detected amount (e.g. concentration) of a placental protein biomarker to a respective predetermined threshold level for the biomarker. The predetermined threshold level can be empirically determined based on knowledge of the amount of the protein in a sample from female subjects across a range of GA. In some embodiments, the predetermined threshold level or value can be determined from a plurality of subjects previously assessed for the correlation or association of the biomarker to a particular GA as confirmed or determined by a clinically validated method, such as ultrasound.

In embodiments of the provided methods, the predetermined threshold value is for classifying GA based on a predetermined GA cutpoint that is a timepoint between 5 weeks and 40 weeks. In some embodiments, the predetermined GA cutpoint is a timepoint between at or about 5 weeks and at or about 20 weeks. In some embodiments, the predetermined GA cutpoint is a timepoint between at or about 5 weeks and at or about 15 weeks (105 days). In some embodiments, the predetermined GA cutpoint is a timepoint between at or about 9 weeks and at or about 12 weeks. In particular embodiments, the predetermined GA cutpoint is at or about 8 weeks. In particular embodiments, the predetermined GA cutpoint is at or about 9 weeks. In particular embodiments, the predetermined GA cutpoint is at or about 10 weeks. In other embodiments, the predetermined GA cutpoint is at or about 11 weeks. In further embodiments, the predetermined GA cutpoint is at or about 12 weeks. In particular embodiments, the predetermined GA cutpoint is at or about 13 weeks. In particular embodiments, the predetermined GA cutpoint is at or about 14 weeks. In particular embodiments, the predetermined GA cutpoint is at or about 15 weeks (105 days). In particular embodiments, the predetermined GA cutpoint is at or about 16 weeks. In particular embodiments, the predetermined GA cutpoint is at or about 17 weeks. In particular embodiments, the predetermined GA cutpoint is at or about 18 weeks. In particular embodiments, the predetermined GA cutpoint is at or about 19 weeks. In particular embodiments, the predetermined GA cutpoint is at or about 20 weeks.

In embodiments of the provided methods, the predetermined GA cutpoint is a timepoint between at or about 56 days and at or about 280 days. In some embodiments, the GA cutpoint is a timepoint between at or about 56 days and at or about 140 days. In some embodiments, the predetermined GA cutpoint is a timepoint between at or about 56 days and at or about 112 days. In some embodiments, the predetermined GA cutpoint is a timepoint between at or about 63 days and at or about 105 days. In provided embodiments, the predetermined GA cutpoint is at or about 64 days, at or about 66 days, at or about 68 days, at or about 70 days, at or about 72 days, at or about 74 days, at or about 76 days, at or about 78 days, at or about 80 days, at or about 82 days, at or about 84 days, at or about 86 days, at or about 88 days, at or about 90 days, at or about 92 days, at or about 94 days, at or about 96 days, at or about 98 days, at or about 100 days, at or about 102 days, at or about 104 days, at or about 106 days, at or about 108 days or at or about 110 days, at or a bout 120 days, at or about 130 days, at or about 140 days, at or about 160 days, at or about 180 days, at or about 200 days, at or about 220 days, at or about 240 days or at or about 280 days, or is any time point between any of the foregoing. In particular embodiments, the predetermined GA cutpoint is at or about 70 days. In particular embodiments, the predetermined GA cutpoint is at or about 104 days. In particular embodiments, the predetermined GA cutpoint is at or about 105 days. In other embodiments, the predetermined GA cutpoint is at or about 140 days.

In some embodiments, the threshold level or value is determined from women who are known to have a pregnancy of 5-40 weeks gestation, such as determined by ultrasound. In some cases, the particular population is chosen using quotas to ensure an estimate of the concentration across the full duration of pregnancy to identify biomarkers that have high sensitivity and specificity in a population of interest, however, oversampling at particular GA of interest can be included. In some embodiments, the population includes an oversampling of women within five gestational weeks before and after the particular predetermined GA cutpoint. For example, for a predetermined GA cutpoint of 10 weeks (70 days) the population includes an oversampling of women at 5-15 weeks GA. In some aspects, the threshold level is determined based on an amount or concentration of the biomarker being assessed, detected or measured in a sample (e.g. serum sample) among a population of such female subjects. In some embodiments, the predetermined threshold level of the one or more placental protein is determined from a scatterplot of the concentration of the placental protein in the sample (e.g. serum) plotted by GA as determined by ultrasound.

Any of a variety of methods can be used to set or identify a predetermined threshold level at which there is a good predictive value (e.g. accuracy, sensitivity, specificity and/or AUC). In some embodiments, the predetermined threshold level is chosen to maximize sensitivity (i.e. the ability of the test to correctly identify subjects with a positive test results as having GA above the predetermined GA cutpoint) or to maximize the positive predictive value (i.e. no or few subjects with a positive test result has a GA lower than the predetermined GA cutpoint). In some embodiments, the predetermined threshold level is chosen to maximize specificity (i.e. the ability of the test to correctly identify subjects with a negative test results as having GA below the predetermined GA cutpoint) or to maximize the negative predictive value (i.e. no or few subjects with a negative test result has a GA greater than the predetermined GA cutpoint).

In some embodiments, the predetermined threshold level or value is one in which there is a good predictive value of the outcome. In particular embodiments, the value is one in which there is a good negative predictive value in which no or few subjects with a negative test result actually has a GA greater than the predetermined GA cutpoint.

In some embodiments, a predetermined threshold level is chosen to maximize sensitivity in identifying GAs greater than or equal to a predetermined GA cutpoint (e.g ≥10 weeks). In some aspects, a predetermined threshold level is an amount (e.g. concentration) such that virtually all pregnancies at greater than or equal to the predetermined GA cutpoint (e.g. ≥10 weeks) will show a positive result (i.e. amount of placental protein biomarker greater than or equal to threshold level). Thus, a subject with a negative result would mean that the GA could be or is likely to be or is less than the predetermined GA cutpoint (e.g. <10 weeks).

In some embodiments, a predetermined threshold level is chosen to maximize accuracy in identifying GAs greater than or equal to a predetermined GA cutpoint (e.g ≥10 weeks). In some embodiments, a predetermined threshold level is chosen to minimize false positives. In other embodiments, a predetermined threshold levels is chosen to minimize false negatives. For example, in some aspects, the utility of the test can be maximized by minimizing the likelihood of false negatives, i.e., situations in which a subject with a negative test result has a GA greater than or equal to the predetermined GA cutpoint (e.g., ≥10 weeks).

In some embodiments, the threshold level or value is based on a receiver operating characteristic (ROC) curve of the placental protein biomarker in a population of subjects having or suspected being pregnant or of having a pregnancy with a GA within a defined sample window. In some cases, the threshold value is determined by the Youden Index, which, in some cases, is the value in which sensitivity and specificity are maximal.

In some embodiments, the predetermined threshold level can be a concentration of the placental protein, such as among a population of female subjects having a generally evenly distributed GA (in some cases with oversampling as described above), at which a minority of or no or few subjects at that concentration or lower have a GA that is greater than or equal to the predetermined GA cutpoint. In some embodiment, the predetermined threshold level is chosen as a concentration value in which at that concentration or lower, such as among a population of subjects having a generally evenly distributed GA (in some cases with oversampling as described above), less than or less than about 20% of such population, such as less than or less than about 15%, less than or less than about 10% or less than or less than about 5%, have a GA that is greater than or equal to the predetermined GA cutpoint.

In some embodiments, the predetermined threshold level can be a concentration of the placental protein, such as among a population of female subjects having a generally evenly distributed GA (in some cases with oversampling as described above), at which a majority or all subjects at that concentration or lower have a GA that is lower than the predetermined GA cutpoint. In some embodiment, the predetermined threshold level is chosen as a concentration value in which at that concentration or lower, such as among a population of subjects having a generally evenly distributed GA (in some cases with oversampling as described above), greater than or greater than about 80% of such population, such as greater than or greater than about 85%, greater than or greater than about 90% or greater than or greater than about 95%, have a GA that is lower than the predetermined GA cutpoint.

In some embodiments, the predetermined threshold level can be determined as a concentration of the placental protein, such as among a population of female subjects having a generally evenly distributed GA (in some cases with oversampling as described above), at which a majority of or all subjects at that concentration or higher have a GA that is greater than or equal to the predetermined GA cutpoint. In some embodiment, the predetermined threshold level is chosen as a concentration value in which at that concentration or higher, such as among a population of subjects having a generally evenly distributed GA (in some cases with oversampling as described above), greater than or greater than about 80% of such population, such as greater than or greater than about 85%, greater than or greater than about 90% or greater than or greater than about 95%, have a GA that is greater than or equal to the predetermined GA cutpoint.

In some embodiments, the predetermined threshold level of each of the one or more placental protein is a value that has been predetermined or selected to or that does provide a sensitivity or net sensitivity of greater than 0.50, greater than 0.60, greater than 0.70, greater than 0.80, greater than 0.90 or greater than 0.95 for predicting or determining a predetermined GA cutpoint. In some cases, the predetermined threshold level of each the one or more placental protein is a value that has been predetermined or selected to or that does provide a specificity or net specificity of greater than 0.25, greater than 0.30, greater than 0.40, greater than 0.50, greater than 0.60, greater than 0.70, greater than 0.80, greater than 0.90 or greater than 0.95 for predicting or determining a predetermined GA cutpoint. In some aspects, the predetermined threshold level for each of the one or more placental protein has been selected to or does provide an area under the curve (AUC), such as in a ROC analysis, of greater than or greater than about 0.65, greater than or greater than about 0.70, greater than or greater than about 0.75, greater than or greater than about 0.80, greater than or greater than about 0.85, greater than or greater than about 0.90 or greater than or greater than about 0.95 for predicting or determining a predetermined GA cutpoint.

In some embodiments, the one or more placental protein biomarker PAPP-A. In some embodiments, the predetermined threshold level of PAPP-A (hereinafter "PAPP-A predetermined threshold level") is a value between at or about 3 ng/mL and at or about 130 ng/mL, between at or about 3 ng/mL and at or about 90 ng/mL, between at or about 3 ng/mL and at or about 45 ng/mL, between at or about 3 ng/mL and at or about 20 ng/mL, between at or about 3 ng/mL and at or about 10 ng/mL, between at or about 3 ng/mL and at or about 5 ng/mL, between at or about 5 ng/mL and at or about 130 ng/mL, between at or about 5 ng/mL and at or about 90 ng/mL, between at or about 5 ng/mL and at or about 45 ng/mL, between at or about 5 ng/mL and at or about 20 ng/mL, between at or about 5 ng/mL and at or about 10 ng/mL, between at or about 10 ng/mL and at or about 130 ng/mL, between at or about 10 ng/mL and at or about 90 ng/mL, between at or about 10 ng/mL and at or about 45 ng/mL, between at or about 10 ng/mL and at or about 20 ng/mL, between at or about 20 ng/mL and at or about 130 ng/mL, between at or about 20 ng/mL and at or about 90 ng/mL, between at or about 20 ng/mL and at or about 45 ng/mL, between at or about 45 ng/mL and at or about 130 ng/mL, between at or about 45 ng/mL and at or about 90 ng/mL, or between at or about 90 ng/mL and at or about 130 ng/mL, each inclusive.

The particular PAPP-A predetermined threshold level can depend on the particular GA cutpoint, such as a particular GA cutpoint selected or chosen for screening or determining eligibility for a prenatal care or clinical treatment decision. In some embodiments, the predetermined GA cutpoint is a timepoint as described herein. In some embodiments, the GA cutpoint that is a timepoint between at or about 5 weeks and at or about 40 weeks. In particular embodiments, the predetermined GA cutpoint is a GA cutpoint that is at or about 63 days (or 9 weeks), at or about 70 days (or 10 weeks), at or about 77 days (or 11 weeks), at or about 84 days (or 12 weeks), at or about 91 days (or 13 weeks), at or about 98 days (or 14 weeks), at or about 105 days (or 15 weeks), at or about 112 days (16 weeks), at or about 119 days (or 17 weeks), at or about 126 days (or 18 weeks), at or about 133 days (or 19 weeks), or at or about 140 days (or 20 weeks), or any timepoint between any of the foregoing.

In some embodiments, the predetermined GA cutpoint is a timepoint between at or about 64 days and at or about 140 days, inclusive. In some embodiments, the predetermined GA cutpoint is at or about 70 days or 10 weeks. In some of any such embodiments, the PAPP-A predetermined threshold level is a value between at or about 3 ng/mL and 10 ng/mL, such as a value between at or about 3 ng/mL and at or about 8 ng/mL, between at or about 3 ng/mL and at or about 6 ng/mL, between at or about 3 ng/mL and at or about 5 ng/mL, between at or about 5 ng/mL and at or about 10 ng/mL, between at or about 5 ng/mL and at or about 8 ng/mL, between at or about 5 ng/mL and at or about 6 ng/mL, between at or about 6 ng/mL and at or about 10 ng/mL, between at or about 6 ng/mL and 8 ng/mL or between at or about 8 ng/mL and at or about 10 ng/mL. In some of any such embodiments, the PAPP-A predetermined threshold level is at or about 3.2 ng/mL, at or about 3.4 ng/mL, at or about 3.6 ng/mL, at or about 3.8 ng/mL, at or about 4.0 ng/mL, at or about 4.2 ng/mL, at or about 4.4 ng/mL, at or about 4.6 ng/mL, at or about 4.8 ng/mL, at or about 5.0 ng/mL, at or about 5.2 ng/mL, at or about 5.4 ng/mL, at or about 5.6 ng/mL, at or about 5.8 ng/mL or at or about 6.0 ng/mL or any value between any of the foregoing. In some of any such embodiments, the PAPP-A predetermined threshold levels is at or about 5.6 ng/mL.

In some embodiments, the predetermined GA cutpoint is a timepoint between at or about 80 days and at or about 140 days, inclusive. In some embodiments, the predetermined GA cutpoint is a timepoint between at or about 15 weeks (105 days) and at or about 18 weeks. In some embodiments, the predetermined GA cutpoint is a timepoint between at or about 100 days and at or about 130 days. In some embodiments, the predetermined GA cutpoint is at or about 112 days. In some embodiments, the predetermined GA cutpoint is at or about 104 days. In some embodiments, the predetermined GA cutpoint is at or about 105 days. In some of any such embodiments, the PAPP-A predetermined threshold level is a value between at or about 3 ng/mL and at or about 80 ng/mL, such as a value between at or about 3 ng/mL and at or about 70 ng/mL, between at or about 3 ng/mL and at or about 60 ng/mL, between at or about 3 ng/mL and at or about 50 ng/mL, between at or about 3 ng/mL and at or about 40 ng/mL, between at or about 3 ng/mL and at or about 30 ng/mL, between at or about 3 ng/mL and at or about 20 ng/mL, between at or about 3 ng/mL and at or about 10 ng/mL, between at or about 10 ng/mL and at or about 80 ng/mL, between at or about 10 ng/mL and at or about 70 ng/mL, between at or about 10 ng/mL and at or about 60 ng/mL, between at or about 10 ng/mL and at or about 50 ng/mL, between at or about 10 ng/mL and at or about 40 ng/mL, between at or about 10 ng/mL and at or about 30 ng/mL, between at or about 10 ng/mL and at or about 20 ng/mL, between at or about 20 ng/mL and at or about 80 ng/mL, between at or about 20 ng/mL and at or about 70 ng/mL, between at or about 20 ng/mL and at or about 60 ng/mL, between at or about 20 ng/mL and at or about 50 ng/mL, between at or about 20 ng/mL and at or about 40 ng/mL, between at or about 20 ng/mL and at or about 30 ng/mL, between at or about 30 ng/mL and at or about 80 ng/mL, between at or about 30 ng/mL and at or about 70 ng/mL, between at or about 30 ng/mL and at or about 60 ng/mL, between at or about 30 ng/mL and at or about 50 ng/mL, between at or about 30 ng/mL and at or about 40 ng/mL, between at or about 40 ng/mL and at or about 80 ng/mL, between at or about 40 ng/mL and at or about 70 ng/mL, between at or about 40 ng/mL and at or about 60 ng/mL, between at or about 40 ng/mL and at or about 50 ng/mL, between at or about 50 ng/mL and at or about 80 ng/mL, between at or about 50 ng/mL and at or about 70 ng/mL, between at or about 50 ng/mL and at or about 60 ng/mL, between at or about 60 ng/mL and at or about 80 ng/mL, between at or about 60 ng/mL and at or about 70 ng/mL, or between at or about 70 ng/mL and at or about 80 ng/mL, each inclusive. In some of any such embodiments, the PAPP-A predetermined threshold level is at or about 10 ng/mL, at or about 14 ng/mL, at or about 18 ng/mL, at or about 22 ng/mL, at or about 26 ng/mL, at or about 30 ng/mL, at or about 34 ng/mL, at or about 38 ng/mL, at or about 42 ng/mL, at or about 46 ng/mL, at or about 50 ng/mL, at or about 54 ng/mL, at or about 60 ng/mL, at or about 64 ng/mL or at or about 68 ng/mL or any value between any of the foregoing. In some of any such embodiments, the PAPP-A predetermined threshold levels is at or about 41.1 ng/mL.

In some embodiments, the predetermined GA cutpoint is at or about 140 days or 20 weeks. In some of any such embodiments, the PAPP-A predetermined threshold level is a value between at or about 3 ng/mL and at or about 130 ng/mL, between at or about 10 ng/mL and at or about 130 ng/mL, between at or about 20 ng/mL and at or about 130 ng/mL, between at or about 40 ng/mL and at or about 130 ng/mL, between at or about 60 ng/mL and at or about 130 ng/mL, between at or about 80 ng/mL and at or about 130 ng/mL, or between at or about 100 ng/mL and at or about 130 ng/mL, each inclusive. In some of any such embodiments, the PAPP-A predetermined threshold level is a value between at or about 60 ng/mL and at or about 130 ng/mL, between at or about 60 ng/mL and at or about 100 ng/mL, between at or about 60 ng/mL and at or about 90 ng/mL, between at or about 60 ng/mL and at or about 80 ng/mL, between at or about 60 ng/mL and at or about 70 ng/mL, between at or about 70 ng/mL and at or about 130 ng/mL, between at or about 70 ng/mL and at or about 100 ng/mL, between at or about 70 ng/mL and at or about 90 ng/mL, between at or about 70 ng/mL and at or about 80 ng/mL, between at or about 80 ng/mL and at or about 130 ng/mL, between at or about 80 ng/mL and at or about 100 ng/mL, between at or about 80 ng/mL and at or about 90 ng/mL, between at or about 90 ng/mL and at or about 130 ng/mL, between at or about 90 ng/mL and at or about 100 ng/mL, or between at or about 90 ng/mL and at or about 130 ng/mL, each inclusive. In some of any such embodiments, the PAPP-A predetermined threshold level is at or about 60 ng/mL, at or about 64 ng/mL, at or about 68 ng/mL, at or about 72 ng/mL, at or about 76 ng/mL, at or about 80 ng/mL, at or about 84 ng/mL, at or about 88 ng/mL, at or about 92 ng/mL, at or about 96 ng/mL, at or about 100 ng/mL, at or about 104 ng/mL, at or about 108 ng/mL, at or about 112 ng/mL or at or about 116 ng/mL or any value between any of the foregoing. In some of any such embodiments, the PAPP-A predetermined threshold levels is at or about 80.3 ng/mL.

In some embodiments, the one or more placental protein biomarker is ADAM-12. In some embodiments, the predetermined threshold level of ADAM-12 (hereinafter "ADAM-12 predetermined threshold level") is a value between at or about 0.5 ng/mL and at or about 15 ng/mL, such as a value between at or about 0.5 ng/mL and at or about 12 ng/mL, between at or about 0.5 ng/mL and at or about 10 ng/mL, between at or about 0.5 ng/mL and at or about 8 ng/mL, between at or about 0.5 ng/mL and at or about 6 ng/mL, between at or about 0.5 ng/mL and at or about 4 ng/mL, between at or about 0.5 ng/mL and at or about 2 ng/mL, between at or about 0.5 ng/mL and at or about 1 ng/mL, between at or about 1 ng/mL and at or about 15 ng/mL, between at or about 1 ng/mL and at or about 12 ng/mL, between at or about 1 ng/mL and at or about 10 ng/mL, between at or about 1 ng/mL and at or about 8 ng/mL, between at or about 1 ng/mL and at or about 6 ng/mL, between at or about 1 ng/mL and at or about 4 ng/mL, between at or about 1 ng/mL and at or about 2 ng/mL, between at or about 2 ng/mL and at or about 15 ng/mL, between at or about 2 ng/mL and at or about 12 ng/mL, between at or about 2 ng/mL and at or about 10 ng/mL, between at or about 2 ng/mL and at or about 8 ng/mL, between at or about 2 ng/mL and at or about 6 ng/mL, between at or about 2 ng/mL and at or about 4 ng/mL, between at or about 4 ng/mL and at or about 15 ng/mL, between at or about 4 ng/mL and at or about 12 ng/mL, between at or about 4 ng/mL and at or about 10 ng/mL, between at or about 4 ng/mL and at or about 8 ng/mL, between at or about 4 ng/mL and at or about 6 ng/mL, between at or about 6 ng/mL and at or about 15 ng/mL, between at or about 6 ng/mL and at or about 12 ng/mL, between at or about 6 ng/mL and at or about 10 ng/mL, between at or about 6 ng/mL and at or about 8 ng/mL, between at or about 8 ng/mL and at or about 15 ng/mL, between at or about 8 ng/mL and at or about 12 ng/mL, between at or about 8 ng/mL and at or about 10 ng/mL, between at or about 10 ng/mL and at or about 15 ng/mL, between at or about 10 ng/mL and at or about 12 ng/mL, and between at or about 12 ng/mL and at or about 15 ng/mL, each inclusive.

The particular ADAM-12 predetermined threshold level can depend on the particular GA cutpoint, such as a particular GA cutpoint selected or chosen for screening or determining eligibility for a prenatal care or clinical treatment decision. In some embodiments, the predetermined GA cutpoint is a timepoint as described herein. In some embodiments, the GA cutpoint that is a timepoint between at or about 5 weeks and at or about 40 weeks. In particular embodiments, the predetermined GA cutpoint is a GA cutpoint that is at or about 63 days (or 9 weeks), at or about 70 days (or 10 weeks), at or about 77 days (or 11 weeks), at or about 84 days (or 12 weeks), at or about 91 days (or 13 weeks), at or about 98 days (or 14 weeks), at or about 105 days (or 15 weeks), at or about 112 days (16 weeks), at or about 119 days (or 17 weeks), at or about 126 days (or 18 weeks), at or about 133 days (or 19 weeks), or at or about 140 days (or 20 weeks), or any timepoint between any of the foregoing.

In some embodiments, the predetermined GA cutpoint is a timepoint between at or about 64 days and at or about 140 days, inclusive. In some embodiments, the predetermined GA cutpoint is at or about 70 days or 10 weeks. In some of any such embodiments, the ADAM-12 predetermined threshold level is a value between at or about 0.5 ng/mL and at or about 4 ng/mL, between at or about 0.5 ng/mL and at or about 3 ng/mL, between at or about 0.5 ng/mL and at or about 2 ng/mL, between at or about 0.5 ng/mL and at or about 1 ng/mL, between at or about 1 ng/mL and at or about 4 ng/mL, between at or about 1 ng/mL and at or about 3 ng/mL, between at or about 1 ng/mL and at or about 2 ng/mL, between at or about 2 ng/mL and at or about 4 ng/mL, between at or about 2 ng/mL and at or about 3 ng/mL, or between at or about 3 ng/mL and at or about 4 ng/mL, inclusive. In some of any such embodiments, the ADAM-12 predetermined threshold level is at or about 0.5 ng/mL, at or about 0.75 ng/mL, at or about 1 ng/mL, at or about 1.25 ng/mL, at or about 1.5 ng/mL, at or about 1.75 ng/mL, at or about 1 ng/mL, at or about 2.25 ng/mL, at or about 2.5 ng/mL, at or about 2.75 ng/mL, at or about 3 ng/mL, at or about 3.25 ng/mL, at or about 3.5 ng/mL, at or about 3.75 ng/mL, at or at or about 4 ng/mL or any value between any of the foregoing. In some of any such embodiments, the ADAM-12 predetermined threshold levels is at or about 2.33 ng/mL.

In some embodiments, the predetermined GA cutpoint is a timepoint between at or about 80 days and at or about 140 days, inclusive. In some embodiments, the predetermined GA cutpoint is a timepoint between at or about 15 weeks (105 days) and at or about 18 weeks. In some embodiments, the predetermined GA cutpoint is a timepoint between at or about 100 days and at or about 130 days. In some embodiments, the predetermined GA cutpoint is at or about 112 days. In some embodiments, the predetermined GA cutpoint is at or about 104 days. In some embodiments, the predetermined GA cutpoint is at or about 105 days. In some of any such embodiments, the ADAM-12 predetermined threshold level is a value between at or about 3.5 ng/mL and 8 ng/mL, between at or about 3.5 ng/mL and at or about 7 ng/mL, between at or about 3.5 ng/mL and at or about 6 ng/mL, between at or about 3.5 ng/mL and at or about 5 ng/mL, between at or about 3.5 ng/mL and at or about 4 ng/mL, between at or about 4 ng/mL and at or about 8 ng/mL, between at or about 4 ng/mL and at or about 7 ng/mL, between at or about 4 ng/mL and at or about 6 ng/mL, between at or about 4 ng/mL and at or about 5 ng/mL, between at or about 5 ng/mL and at or about 8 ng/mL, between at or about 5 ng/mL and at or about 7 ng/mL, between at or about 5 ng/mL and at or about 6 ng/mL, between at or about 6 ng/mL and at or about 8 ng/mL, between at or about 6 ng/mL and at or about 7 ng/mL or between at or about 7 ng/mL and at or about 8 ng/mL, inclusive. In some of any such embodiments, the ADAM-12 predetermined threshold is at or about 3.5 ng/mL, at or about 4 ng/mL, at or about 4.25 ng/mL, at or about 4.5 ng/mL, at or about 4.75 ng/mL, at or about 5 ng/mL, at or about 5.25 ng/mL, at or about 5.5 ng/mL, at or about 6 ng/mL, at or about 6.25 ng/mL, at or about 6.5 ng/mL, at or about 6.75 ng/mL, at or about 7 ng/mL, at or about 7.25 ng/mL, at or about 7.5 ng/mL, at or about 7.75 ng/mL or at or about 8 ng/mL, or any value between any of the foregoing. In some of any such embodiments, the ADAM-12 predetermined threshold levels is at or about 4.82 ng/mL.

In some embodiments, the predetermined GA cutpoint is at or about 140 days or 20 weeks. In some of any such embodiments, the ADAM-12 predetermined threshold level is a value between at or about 8 ng/mL and at or about 14 ng/mL, between at or about 8 ng/mL and at or about 12 ng/mL, between at or about 8 ng/mL and at or about 10 ng/mL, between at or about 10 ng/mL and at or about 14 ng/mL, between at or about 10 ng/mL and at or about 12 ng/mL or between at or about 12 ng/mL and at or about 14 ng/mL, each inclusive. In some of any such embodiments, the ADAM-12 predetermined threshold is at or about 8 ng/mL, at or about 8.5 ng/mL, at or about 9 ng/mL, at or about 9.5 ng/mL, at or about 10 ng/mL, at or about 10.5 ng/mL, at or about 11 ng/mL, at or about 11.5 ng/mL, at or about 12 ng/mL, at or about 12.5 ng/mL, at or about 13 ng/mL, at or about 13.5 ng/mL, or at or about 14 ng/mL, or any value between any of the foregoing. In some embodiments, the ADAM-12 predetermined threshold levels is at or about 9.135 ng/mL.

In some embodiments, the one or more placental protein biomarker is PSG1. In some embodiments, the predetermined threshold level of PSG1 (hereinafter "PSG1 predetermined threshold level") is a value between at or about 5 ng/mL and at or about 5000 ng/mL, such as a value between at or about 5 ng/mL and at or about 4000 ng/mL, between at or about 10 ng/mL and at or about 3000 ng/mL, each inclusive.

The particular PSG1 predetermined threshold level can depend on the particular GA cutpoint, such as a particular GA cutpoint selected or chosen for screening or determining eligibility for a prenatal care or clinical treatment decision. In some embodiments, the predetermined GA cutpoint is a timepoint as described herein. In some embodiments, the GA cutpoint that is a timepoint between at or about 5 weeks and at or about 40 weeks. In particular embodiments, the predetermined GA cutpoint is a GA cutpoint that is at or about 63 days (or 9 weeks), at or about 70 days (or 10 weeks), at or about 77 days (or 11 weeks), at or about 84 days (or 12 weeks), at or about 91 days (or 13 weeks), at or about 98 days (or 14 weeks), at or about 105 days (or 15 weeks), at or about 112 days (16 weeks), at or about 119 days (or 17 weeks), at or about 126 days (or 18 weeks), at or about 133 days (or 19 weeks), or at or about 140 days (or 20 weeks), or any timepoint between any of the foregoing.

In some embodiments, the predetermined GA cutpoint is a timepoint between at or about 64 days and at or about 140 days, inclusive. In some embodiments, the predetermined GA cutpoint is at or about 70 days or 10 weeks. In some of any such embodiments, the PSG1 predetermined threshold level is a value between at or about 5 ng/mL and at or about 500 ng/mL, between at or about 5 ng/mL and at or about 250 ng/mL, between at or about 5 ng/mL and at or about 100 ng/mL between at or about 5 ng/mL and at or about 50 ng/mL, between at or about 5 ng/mL and at or about 25 ng/mL, between at or about 5 ng/mL and at or about 10 ng/mL, between at or about 10 ng/mL and at or about 500 ng/mL, between at or about 10 ng/mL and at or about 250 ng/mL, between at or about 10 ng/mL and at or about 100 ng/mL, between at or about 10 ng/mL and at or about 50 ng/mL, between at or about 10 ng/mL and at or about 25 ng/mL, between at or about 25 ng/mL and at or about 500 ng/mL, between at or about 25 ng/mL and at or about 250 ng/mL, between at or about 25 ng/mL and at or about 100 ng/mL, between at or about 25 ng/mL and at or about 50 ng/mL, between at or about 50 ng/mL and at or about 500 ng/mL, between at or about 50 ng/mL and at or about 250 ng/mL, between at or about 50 ng/mL and at or about 100 ng/mL, between at or about 100 ng/mL and at or about 500 ng/mL, between at or about 100 ng/mL and at or about 250 ng/mL, between at or about 250 ng/mL and at or about 500 ng/mL, each inclusive. In some of any such embodiments, the PSG1 predetermined threshold level is at or about 10 ng/mL, at or about 25 ng/mL, at or about 50 ng/mL, at or about 100 ng/mL, at or about 250 ng/mL or at or about 500 ng/mL or is any value between any of the foregoing. In some embodiments, the PSG1 predetermined threshold level is at or about 10.3 ng/mL.

In some embodiments, the predetermined GA cutpoint is a timepoint between at or about 64 days and at or about 140 days, inclusive. In some embodiments, the predetermined GA cutpoint is a timepoint between at or about 80 days and at or about 140 days, inclusive. In some embodiments, the predetermined GA cutpoint is a timepoint between at or about 15 weeks (105 days) and at or about 18 weeks. In some embodiments, the predetermined GA cutpoint is a timepoint between at or about 100 days and at or about 130 days. In some embodiments, the predetermined GA cutpoint is at or about 140 days or 20 weeks. In some embodiments, the predetermined GA cutpoint is at or about 112 days. In some embodiments, the predetermined GA cutpoint is at or about 104 days. In some embodiments, the predetermined GA cutpoint is at or about 105 days. In some of any such embodiments, the PSG1 predetermined threshold level is a value between at or about 2000 pg/mL and at or about 5000 pg/mL, between at or about 2000 pg/mL and at or about 4000 pg/mL, between at or about 2000 pg/mL and at or about 4500 pg/mL, between at or about 2000 pg/mL and at or about 4000 pg/mL, between at or about 2000 pg/mL and at or about 3500 pg/mL, between at or about 2000 pg/mL and at or about 3000 pg/mL, between at or about 3000 pg/mL and at or about 5000 pg/mL, between at or about 3000 pg/mL and at or about 4000 pg/mL, between at or about 3000 pg/mL and at or about 4500 pg/mL, between at or about 3000 pg/mL and at or about 4000 pg/mL, between at or about 3000 pg/mL and at or about 3500 pg/mL, between at or about 3500 pg/mL and at or about 5000 pg/mL, between at or about 3500 pg/mL and at or about 4000 pg/mL, between at or about 3500 pg/mL and at or about 4500 pg/mL, between at or about 3500 pg/mL and at or about 4000 pg/mL, between at or about 4000 pg/mL and at or about 5000 pg/mL, between at or about 4000 pg/mL and at or about 4500 pg/mL or between at or about 4500 pg/mL and at or about 5000 pg/mL, each inclusive. In some embodiments, the PSG1 predetermined threshold level is at or about 2000 pg/mL, at or about 2500 pg/mL, at or about 3000 pg/mL, at or about 3500 pg/mL, at or about 4000 pg/mL, at or about 4500 pg/mL or at or about 5000 pg/mL or any value between any of the foregoing. In some embodiments, the PSG1 predetermined threshold level is at or about 3537 mg/mL.

In some embodiments, the one or more placental protein biomarker is HPL. In some embodiments, the predetermined threshold level of HPL (hereinafter "HPL predetermined threshold level") is a value between at or about 0.02 mg/L and at or about 4 mg/L, such as between at or about 0.02 mg/L and at or about 3 mg/L, between at or about 0.02 mg/L and at or about 2 mg/L, between at or about 0.02 mg/L and at or about 1 mg/L, between at or about 0.02 mg/L and at or about 0.5 mg/L, between at or about 0.02 mg/L and at or about 0.1 mg/L, between at or about 0.02 mg/L and at or about 0.05 mg/L, between at or about 0.05 mg/L and at or about 4 mg/L, between at or about 0.05 mg/L and at or about 3 mg/L, between at or about 0.05 mg/L and at or about 2 mg/L, between at or about 0.05 mg/L and at or about 1 mg/L, between at or about 0.05 mg/L and at or about 0.5 mg/L, between at or about 0.05 mg/L and at or about 0.1 mg/L, between at or about 0.1 mg/L and at or about 4 mg/L, between at or about 0.1 mg/L and at or about 3 mg/L, between at or about 0.1 mg/L and at or about 2 mg/L, between at or about 0.1 mg/L and at or about 1 mg/L, between at or about 0.1 mg/L and at or about 0.5 mg/L, between at or about 0.5 mg/L and at or about 4 mg/L, between at or about 0.5 mg/L and at or about 3 mg/L, between at or about 0.5 mg/L and at or about 2 mg/L, between at or about 0.5 mg/L and at or about 1 mg/L, between at or about 1 mg/L and at or about 4 mg/L, between at or about 1 mg/L and at or about 3 mg/L, between at or about 1 mg/L and at or about 2 mg/L, between at or about 2 mg/L and at or about 4 mg/L, between at or about 2 mg/L and at or about 3 mg/L, or between at or about 3 mg/L and at or about 4 mg/L, each inclusive.

The particular HPL predetermined threshold level can depend on the particular GA cutpoint, such as a particular GA cutpoint selected or chosen for screening or determining eligibility for a prenatal care or clinical treatment decision. In some embodiments, the predetermined GA cutpoint is a timepoint as described herein. In some embodiments, the GA cutpoint that is a timepoint between at or about 5 weeks and at or about 40 weeks. In particular embodiments, the predetermined GA cutpoint is a GA cutpoint that is at or about 63 days (or 9 weeks), at or about 70 days (or 10 weeks), at or about 77 days (or 11 weeks), at or about 84 days (or 12 weeks), at or about 91 days (or 13 weeks), at or about 98 days (or 14 weeks), at or about 105 days (or 15 weeks), at or about 112 days (16 weeks), at or about 119 days (or 17 weeks), at or about 126 days (or 18 weeks), at or about 133 days (or 19 weeks), or at or about 140 days (or 20 weeks), or any timepoint between any of the foregoing.

In some embodiments, the predetermined GA cutpoint is a timepoint between at or about 64 days and at or about 140 days, inclusive. In some embodiments, the predetermined GA cutpoint is at or about 70 days or 10 weeks. In some of any such embodiments, the HPL predetermined threshold level is a value between at or about 0.02 mg/L and at or about 0.1 mg/L, between at or about 0.02 mg/L and at or about 0.08 mg/L, between at or about 0.02 mg/L and at or about 0.06 mg/L, between at or about 0.02 mg/L and at or about 0.04 mg/L, between at or about 0.04 mg/L and at or about 0.1 mg/L, between at or about 0.04 mg/L and at or about 0.08 mg/L, between at or about 0.04 mg/L and at or about 0.06 mg/L, between at or about 0.06 mg/L and at or about 0.1 mg/L, between at or about 0.06 mg/L and at or about 0.08 mg/L, or between at or about 0.08 mg/L and 0.1 mg/L, each inclusive. In some of any such embodiments, the HPL predetermined threshold is at or about 0.02 mg/L, at or about 0.025 mg/L, at or about 0.03 mg/L, at or about 0.035 mg/L, at or about 0.04 mg/L, at or about 0.045 mg/L, at or about 0.05 mg/L, at or about 0.055 mg/L, at or about 0.06 mg/L, at or about 0.065 mg/L, at or about 0.07 mg/L, at or about 0.075 mg/L or at or about 0.08 mg/L or any value between any of the foregoing. In some of any such embodiments, the HPL predetermined threshold is at or about 0.03 mg/L.

In some embodiments, the predetermined GA cutpoint is a timepoint between at or about 80 days and at or about 140 days, inclusive. In some embodiments, the predetermined GA cutpoint is a timepoint between at or about 15 weeks (105 days) and at or about 18 weeks. In some embodiments, the predetermined GA cutpoint is a timepoint between at or about 100 days and at or about 130 days. In some embodiments, the predetermined GA cutpoint is at or about 112 days. In some embodiments, the predetermined GA cutpoint is at or about 104 days. In some embodiments, the predetermined GA cutpoint is at or about 105 days. In some of any such embodiments, the HPL predetermined threshold level is a value between at or about 0.1 mg/L and at or about 1 mg/L, between at or about 0.1 mg/L and at or about 0.9 mg/L, between at or about 0.1 mg/L and at or about 0.75 mg/L, between at or about 0.1 mg/L and at or about 0.5 mg/L, between at or about 0.1 mg/L and at or about 0.25 mg/L, between at or about 0.25 mg/L and at or about 1 mg/L, between at or about 0.25 mg/L and at or about 0.9 mg/L, between at or about 0.25 mg/L and at or about 0.75 mg/L, between at or about 0.25 mg/L and at or about 0.5 mg/L, between at or about 0.5 mg/L and at or about 1 mg/L, between at or about 0.5 mg/L and 0.9 mg/L, between at or about 0.5 mg/L and at or about 0.75 mg/L, between at or about 0.75 mg/L and at or about 1 mg/L, between at or about 0.75 mg/L and at or about 0.9 mg/L, or between at or about 0.9 mg/L and at or about 1 mg/L, each inclusive. In some of any such embodiments, the HPL predetermined threshold level is at or about 0.1 mg/L, at or about 0.2 mg/L, at or about 0.3 mg/L, at or about 0.4 mg/L, at or about 0.5 mg/L, at or about 0.6 mg/L, at or about 0.7 mg/L, at or about 0.8 mg/L, at or about 0.9 mg/L or at or about 1 mg/L, or any value between any of the foregoing. In some of any such embodiments, the HPL predetermined threshold is at or about 0.913 mg/L.

In some embodiments, the predetermined GA cutpoint is at or about 140 days or 20 weeks. In some of any such embodiments, the HPL predetermined threshold level is a value between at or about 1 mg/L and at or about 3 mg/L, between at or about 1 mg/L and at or about 2.5 mg/L, between at or about 1 mg/L and at or about 2 mg/L, between at or about 1 mg/L and at or about 1.5 mg/L, between at or about 1.5 mg/L and at or about 3 mg/L, between at or about 1.5 mg/L and at or about 2.5 mg/L, between at or about 1.5 mg/L and at or about 2 mg/L, between at or about 2 mg/L and at or about 3 mg/L, between at or about 2 mg/L and at or about 2.5 mg/L, between at or about 2.5 mg/L and at or about 3 mg/L, each inclusive. In some of any such embodiments, the hPL predetermined threshold level is at or about 1 mg/L, at or about 1.3 mg/L, at or about 1.5 mg/L, at or about 1.7 mg/L, at or about 1.9 mg/L, at or about 2 mg/L, at or about 2.25 mg/L, at or about 2.5 mg/L, at or about 2.75 mg/L or at or about 3 mg/L or any value between any of the foregoing. In some of any such embodiments, the hPL predetermined threshold level is at or about 1.95 mg/L.

C. Gestational Age Assessment

The provided methods include predicting the GA of a subject using a detected or measured amount (e.g. concentration) of a placental protein biomarker. Such prediction can be accomplished by providing the detected amount as input to a process that uses detected amounts of the placental protein biomarker as a continuous predictor of GA. Based on the detected amount provided as input, the process supplies a predicted GA. In some embodiments, the process is based on knowledge of the amount of the protein in a sample from pregnant subjects across a range of GAs. In some embodiments, the process is based on knowledge of protein amounts from a plurality of pregnant subjects previously assessed for the correlation or association of the biomarker to GAs as confirmed or determined by another clinical method, such as ultrasound.

In some embodiments, the process is a regression model that uses the amounts of one or more proteins as continuous predictors for GA. Regression models are known in the art and include linear and non-linear models. In some embodiments, the process comprises a plurality of regression models, for instance regression models using different protein amounts as predictors for GA or regression models trained to predict GA within specific windows or time periods. In some embodiments, the regression model is, or the plurality of regression models comprises, a linear regression model, a piecewise linear model, a polynomial regression model, a Bayesian model, or any combination of any of the foregoing.

In some embodiments, the process is based on protein amounts from a plurality of pregnant subjects whose GAs fall within a particular range. In embodiments of the provided methods, the range is between at or about 5 weeks and at or about 40 weeks. In some embodiments, the range is between at or about 5 weeks and at or about 20 weeks. In some embodiments, the range is between at or about 5 weeks and at or about 15 weeks (105 days). In some embodiments, the range is between at or about 9 weeks and at or about 12 weeks. In embodiments of the provided methods, the range is between at or about 56 days and at or about 280 days. In some embodiments, the range is between at or about 56 days and at or about 140 days. In some embodiments, the range is between at or about 56 days and at or about 112 days. In some embodiments, the range is between at or about 63 days and at or about 105 days.

In some embodiments, the process is based on protein amounts of women who are known to have a pregnancy of 5-40 weeks gestation, such as determined by ultrasound. In some cases, the particular population is chosen using quotas to ensure an estimate of the concentration across the full duration of pregnancy to identify biomarkers that have high sensitivity and specificity in a population of interest. However, oversampling at particular GA of interest can be included. In some embodiments, the population includes an oversampling of women within five gestational weeks before and after a particular predetermined GA cutpoint. For example, for a predetermined GA cutpoint of 10 weeks (70 days), the population includes an oversampling of women at 5-15 weeks GA. In some aspects, the process is based on an amount or concentration of the biomarker being assessed, detected or measured in a sample (e.g. serum sample) among a population of such female subjects.

Any of a variety of methods can be used to set or identify a process, for instance one or more regression models, with good accuracy in modeling and/or predicting GA. In some embodiments, whether or not the process is considered to have good accuracy in modeling GA is based on one or more evaluation metrics. Such evaluation metrics are known in the art and include, but are not limited to, R-squared, Root Mean Squared Error (RMSE), Residual Standard Error (RSE), Mean Absolute Error (MAE), Adjusted R-squared, Akaike's Information Criteria (AIC), corrected AIC, Bayesian Information Criteria (BIC), and Mallows Cp. In some embodiments, high accuracy for modeling GAs within a particular range is prioritized.

In some embodiments, the process (e.g. regression model) has high accuracy in predicting GA using measured protein amounts, for instance serum protein concentrations, from pregnant subjects. In some embodiments, the GA predicted by the process (e.g. regression model) using one or more measured protein amounts of a placental protein (e.g. PAPP-A), for instance serum protein concentrations, is or is on average within or within about 20% of the GA as determined by another clinical technique, for instance ultrasound. In some embodiments, the GA predicted by the process is or is on average within or within about 18% of the GA as determined by another clinical technique. In some embodiments, the GA predicted by the process is or is on average within or within about 16% of the GA as determined by another clinical technique. In some embodiments, the GA predicted by the process is or is on average within or within about 14% of the GA as determined by another clinical technique. In some embodiments, the GA predicted by the process is or is on average within or within about 12% of the GA as determined by another clinical technique. In some embodiments, the GA predicted by the process is or is on average within or within about 10% of the GA as determined by another clinical technique. In some embodiments, the GA predicted by the process is or is on average within or within about 9% of the GA as determined by another clinical technique. In some embodiments, the GA predicted by the process is or is on average within or within about 8% of the GA as determined by another clinical technique. In some embodiments, the GA predicted by the process is or is on average within or within about 7% of the GA as determined by another clinical technique. In some embodiments, the GA predicted by the process is or is on average within or within about 6% of the GA as determined by another clinical technique. In some embodiments, the GA predicted by the process is or is on average within or within about 5% of the GA as determined by another clinical technique. In some embodiments, the GA predicted by the process is or is on average within or within about 4% of the GA as determined by another clinical technique. In some embodiments, the GA predicted by the process is or is on average within or within about 3% of the GA as determined by another clinical technique. In some embodiments, the GA predicted by the process is or is on average within or within about 2% of the GA as determined by another clinical technique. In some embodiments, the GA predicted by the process is or is on average within or within about 1% of the GA as determined by another clinical technique.

D. Screening for Clinical or Prenatal Care

Also provided herein are methods of selecting or screening for a subject as a candidate for or eligible for a clinical or prenatal care based on results of assessing or classifying the GA of the pregnancy of a subject, such as in accord with any of the above provided methods. In some embodiments, the methods of selecting or screening a subject for a prenatal care or clinical treatment includes carrying out any of the provided methods to classify, determine, or assess the GA age of a pregnancy. Information about the GA age of the pregnancy can inform or facilitate decisions about the particular prenatal care or clinical care of the subject, such as by excluding subjects who would not be a suitable candidate or eligible for a particular care by virtue of GA of the pregnancy. It is within the level of skill of a medical professional to determine particular predetermined GA cutpoints that would be useful to assess if a subject eligible or not eligible for particular prenatal care or clinical treatments or assessments. Exemplary methods and GA cutpoints are provided.

In some embodiments, the provided screening methods can be carried out as part of a point-of-care test. In some embodiments, the provided screening methods can be carried out by a skilled technician in a laboratory is carried out as part of a laboratory test. In some embodiments, the methods of screening or selecting a subject can be carried out without an ultrasound or other intrusive or expensive clinical assessment.

In some embodiments, if a subject is classified to have a GA below the predetermined cutpoint GA (e.g. negative test) the subject is eligible for certain clinical or prenatal care decision. In other embodiments, if a subject is classified to have a GA above the predetermined cutpoint GA (e.g. positive test) the subject is excluded or ineligible from certain decisions related to prenatal care and/or requires further tests or assessment prior to certain prenatal care actions.

In some embodiments, if a subject is classified to have a GA below the predetermined cutpoint GA (e.g. negative test) the subject is excluded or is ineligible for certain clinical or prenatal care decisions and/or requires further tests or assessment prior to certain prenatal care actions. In other embodiments, if a subject is classified to have a GA above the predetermined GA (e.g. positive test) the subject is eligible for certain decisions related to prenatal care.

In some embodiments, if the subject is classified as having a GA predicted to be less than the predetermined GA cutpoint the subject is eligible for or selected for a particular prenatal care or clinical treatment or assessment. Thus, also provided are methods for screening a subject for eligibility for a prenatal care or clinical treatment or assessment involving classifying the GA of a pregnancy of the subject according to any of the provided methods, and if the subject is classified as having a GA predicted to be less than the predetermined GA cutpoint the subject is selected for a particular prenatal care or clinical treatment or assessment.

In some embodiments, the GA cutpoint is dependent on the particular prenatal care, clinical treatment or other medically related decision. In some aspects, the GA cutpoint can be chosen depending on the endpoint of a test in which a positive or negative result is desired. The test can be a test related to or that may aid or facilitate certain decisions related to care or treatment, such as related to a decision about a particular level of health care that may be desired (e.g. tertiary care setting), a decision about appropriateness of particular diagnostic or clinical tests (e.g. aminocentesis, glucose tolerance test or ultrasound), a decision about eligibility for a medical abortion, a decision about appropriateness of certain social programs, or a life decision (e.g. buying a house or getting married), In some embodiments, the provided methods are used for anyone whose early pregnancy is of unknown duration. Thus, the provided methods can provide some information about the relative date of pregnancy. In some embodiments, a test based on a predetermined GA cutpoint or cutpoints can be used to estimate the GA of the pregnancy, e.g. as less than one or more of the predetermined GA cutpoint or cutpoints or as greater than or equal to one or more of the predetermined GA cutpoint or cutpoints. In some embodiments, a test based on a predetermined GA cutpoint (e.g. 10 weeks) can distinguish pregnancies of such duration or less from later gestations. In such screening methods, the GA cutpoint can be empirically determined depending on the particular purpose of a desired test. Any GA cutpoint can be used as a guide to classify a pregnancy as being or likely being longer or shorter than the duration of the set predetermined GA cutpoint.

In some embodiments, the provided methods are used to guide decisions related to prenatal care activities or prenatal clinical treatments to be performed during various GA time windows throughout pregnancy, for instance during one or more prenatal visits to a medical provider. Prenatal care activities or prenatal clinical treatments and their associated GA time windows are known in the art (see, e.g., Fescina et al., Montevideo: CLAP/WP; 2009 (CLAP/WR. Scientific Publication; 1562.2); and "WHO recommendations on antenatal care for a positive pregnancy experience", World Health Organization; both of which are incorporated by reference herein in their entirety). In some embodiments, the GA time window is any time before a GA of at or about 20 weeks, and the activities include but are not limited to pregnancy testing, amenorrhea calculation, perinatal clinical record and risk assessment, exhaustive clinical examination, body weight assessment, height assessment, risky lifestyle investigation, rubeolla susceptibility detection, anti-tetanic vaccine administration, oral examination, breast examination, gynecological examination, PAP, colposcopy, blood group and RH factor assessment, toxoplasmosis detection, HIV detection, hemoglobin assays, iron and folic acid supplementation, syphilis detection, Chagas' Disease detection, malaria detection, urine culture, diabetes detection, education for childbirth and breastfeeding, and any combination of any of the foregoing. In some embodiments, the GA time window is any time between a GA of at or about 22 weeks and a GA of at or about 24 weeks, and the activities include but are not limited to amenorrhea calculation, perinatal clinical record and risk assessment, body weight assessment, risky lifestyle investigation, anti-tetanic vaccine administration, iron and folic acid supplementation, education for childbirth and breastfeeding, blood pressure assessment, fetal growth assessment, fetal livelihood diagnosis, and any combination of any of the foregoing. In some embodiments, the GA time window is any time between a GA of at or about 27 weeks and a GA of at or about 29 weeks, and the activities include but are not limited to amenorrhea calculation, perinatal clinical record and risk assessment, body weight assessment, anti-tetanic vaccine administration, toxoplasmosis detection, hemoglobin assays, iron and folic acid supplementation, urine culture, education for childbirth and breastfeeding, blood pressure assessment, fetal growth assessment, fetal livelihood diagnosis, and any combination of any of the foregoing. In some embodiments, the GA time window is any time between a GA of at or about 33 weeks and a GA of at or about 35 weeks, and the activities include but are not limited to amenorrhea calculation, perinatal clinical record and risk assessment, body weight assessment, risky lifestyle investigation, hemoglobin assays, iron and folic acid supplementation, syphilis detection, diabetes detection, B. *Streptococcus* infection detection, education for childbirth and breastfeeding, blood pressure assessment, fetal growth assessment, fetal livelihood diagnosis, and any combination of any of the foregoing. In some embodiments, the GA time window is any time between a GA of at or about 38 weeks and a GA of at or about 40 weeks, and the activities include but are not limited to amenorrhea calculation, perinatal clinical record and risk assessment, body weight assessment, iron and folic acid supplementation, education for childbirth and breastfeeding, blood pressure assessment, fetal growth assessment, fetal livelihood diagnosis, pelvic capacity assessment, contraceptive counseling and provision, and any combination of any of the foregoing.

In some embodiments, the provided methods are used to guide decisions related to screening based on a GA cutpoint at the end of embryogenesis, i.e. at or about 10 weeks or 70 days. In particular aspects, information about whether a pregnancy is at the end of embryogenesis is relevant for a variety of clinical or prenatal care decisions. In some embodiments, such a test would be useful for assessing eligibility for early aspiration or outpatient medical abortion. In some embodiments, the provided screening methods are used to assess eligibility for medical abortions. In some embodiments, the medical abortion is early aspiration. In some embodiments, the medical abortion is outpatient medical abortion. In particular embodiments, a test with a GA cutpoint of at or about 10 weeks or at or about 70 days could be used to screen female subjects for eligibility or ineligibility for a medical abortion.

In some embodiments, the provided methods can be used to screen subjects that may be susceptible to or at risk of embryotoxicity. In particular embodiments, embryotoxicity is of primary concern within the first 8-10 weeks of gestation. In provided embodiments, the methods provide a test that can identify pregnancies that have progressed beyond that point in order to clear a female subject from being able to engage in certain activities which may not be desired at earlier weeks of gestation, such as due to risk from potentially dangerous exposures. In such embodiments, a test with a GA cutpoint of at or about 8 weeks, at or about 9 weeks or at or about 10 weeks, or any value between any of the foregoing, would be useful to distinguish earlier and later pregnancies based on embryotoxicity risk.

In some embodiments, the provided methods can be used to screen or select subjects that may be eligible or ineligible for certain diagnostic or clinical tests or procedures. For example, early in pregnancy, such as prior to the end of embryogenesis, it may not be desirable to carry out certain tests or procedures. In some embodiments, the test or procedure relates to a fetal or maternal screening. In some embodiments, the test or procedure is amniocentesis. In some embodiments, the test or procedure is a glucose tolerance test. In some embodiments, the test or procedure is or includes an ultrasound.

In particular embodiments, the provided methods can be used to screen or select subjects that may be eligible or ineligible for a test to see if a woman is at increased risk of chromosomal abnormalities, such as women who are over age 35 years of age at delivery, or those who have had an abnormal maternal serum screening test. In some embodiments, the provided methods can be carried out to determine if a woman is suitable for amniocentesis, which, in some cases, is offered to women between 15 and IX weeks of gestation age. In some embodiments, the test can be used to assess suitability for certain prenatal screening tests, including screening for a chromosomal abnormality chromosomal such as trisomy-13, trisomy-18, Turner syndrome, and Klinefelter syndrome, or trisomy 21 (Down syndrome). In some of any such embodiments, a test with a GA cutpoint of at or about 10 weeks or later, such as at or about 15 weeks (105 days), at or about 16 weeks, at or about 17 weeks, or at or about 18 weeks, or any value between any of the foregoing, can be useful to distinguish earlier and later pregnancies based on suitability of the female subject for being eligible for tests to assess chromosomal abnormalities or that involve an amniocentesis. In some of any such embodiments, a test with a GA cutpoint of at or about 104 days or at or about 105 days or later can be useful to distinguish earlier and later pregnancies based on suitability of the female subject for being eligible for tests to assess chromosomal abnormalities or that involve an amniocentesis.

In particular embodiments, the provided methods can be used to screen or select subjects that many be eligible or ineligible for glucose tolerance test, which is a test that is normally not carried out until 26-28 weeks of gestation. In such embodiments, a test with a GA cutpoint of at or about 20 weeks (140 days) or later, such as at or about 26 weeks, at or about 27 weeks, at or about 28 weeks, or any value between any of the foregoing, can be useful to distinguish earlier and later pregnancies based on suitability of the female subject for being eligible for a glucose tolerance test.

In some embodiments, the accurate determination of the GA of a pregnant subject allows for the selection of prenatal treatments suitable for the pregnant subject at that GA. Exemplary prenatal treatments include but are not limited to nutritional interventions, maternal and/or fetal assessment, preventive measures, and interventions for common physiological symptoms.

III. DEVICES, KITS, ARTICLES OF MANUFACTURE AND SYSTEMS

Provided herein is a device for carrying out any of the provided methods. In some embodiments, the device is a diagnostic device. In some embodiments, the device includes a solid support to which is attached or immobilized antibodies or antigen-binding fragments for detecting the placental protein biomarker. In some embodiments, a solid support may be a bead, column, an array, an assay plate, microwell, a cartridge, a stick, a filter, or a strip that is inserted into a device or attached to a device and is used as part of the device in order for the device to be operable. In some embodiments, the solid support is the device. In some embodiments, the device is a portable device such as a handheld device. In some embodiments, the device is a stationary device. The device may be manually operated or automatically operated. In some embodiments, the device is an electronic device. Any suitable device for use with the solid supports provided herein or use in the methods provided herein may be used. Non-limiting examples of suitable devices are described below and include commercially available devices such as, but not limited to, i-STAT® handheld (Abbott), Minicare I-20 (Phillips) and similar handheld devices.

Provided herein are articles of manufacture or kits that comprise an antibody or antigen-binding fragment for detecting a placental protein biomarker as described. In some embodiments, the kits are compatible for operation in connection with a system or a device for detecting the placental protein biomarker in one or more samples in accord with any of the provided methods. In some embodiments, the kit further includes the device.

In some embodiments, the kits further contain reagents for performing the methods. Kits can optionally include one or more components such as instructions for use, devices and additional reagents (e.g., sterilized water or saline solutions for dilution of the compositions and/or reconstitution of lyophilized protein), and components, such as tubes, containers and syringes for practice of the methods. In some embodiments, the kits can further contain reagents for collection of samples, preparation and processing of samples, and/or reagents for quantitating the amount of placental protein in a sample, such as, but not limited to, detection reagents, such as antibodies, buffers, substrates for enzymatic staining, chromagens or other materials, such as slides, containers, microtiter plates, and optionally, instructions for performing the methods. Those of skill in the art will recognize many other possible containers and plates and reagents that can be used in accord with the provided methods.

In some embodiments, the kit or article of manufacturer comprises reagents or components for carrying out any of the provided methods. In some embodiments, the article of manufacture or kit comprises a solid support, including a solid support formed of glass (e.g., controlled pore glass), polysaccharides (e.g., agarose), polyacrylamides, polystyrene, polyvinyl alcohol, nitrocellulose, cellulose, nylon, silicones and other material well known in the art that is used in a solid support for direct or indirect attachment of an antibody. Solid supports included in the articles of manufacture or kits provided herein include, but are not limited to, a bead, column (e.g., chromatography column, etc.), an array (e.g., microarray, nanoarray, etc.), an assay plate, a cartridge, a stick, a filter, a strip or any other solid support described herein. In some embodiments, the article of manufacture or kit comprises instructions for attaching one or more antibodies to the solid support. In some embodiments, the article of manufacture or kit comprises one or more antibodies attached directly or indirectly to the solid support.

In some embodiments, the article of manufacture or kit comprises one or more reagent or other materials desirable from a commercial, therapeutic, and user standpoint including secondary antibodies, affinity labels, capture reagents, buffers, diluents, signal detection agents, filters, needles, syringes, capillary tubes, and package inserts with instructions for use.

In some embodiments, the kits can be provided as articles of manufacture that include packing materials for the packaging of the antibodies or compositions thereof or the one or more additional reagents or components. For example, the kits can contain containers, bottles, tubes, vial and any packaging material suitable for separating or organizing the components of the kit.

In some embodiments, the kit includes one or more containers. Suitable containers include, for example, bottles, vials (e.g., dual chamber vials), syringes (such as single or dual chamber syringes) and test tubes. The one or more containers may be formed from a variety of materials such as glass or plastic. The one or more containers hold a composition comprising an antibody or other reagents for use in the methods. The article of manufacture or kit herein may comprise the antibodies or reagents in separate containers or in the same container. In some embodiments, the one or more containers holding the composition may be a single-use vial or a multi-use vial, which, in some cases, may allow for repeat use of the reconstituted composition.

In some embodiments, the article of manufacture or kit may further comprise a second container comprising a suitable diluent. The article of manufacture or kit may further include other materials desirable from a commercial, therapeutic, and user standpoint, including other buffers, diluents, filters, needles, syringes, therapeutic agents and/or package inserts with instructions for use.

In some embodiments, the kit can, optionally, include instructions. Instructions typically include a tangible expression describing the antibodies and, optionally, other components included in the kit, and methods for using the antibodies to detect or measure placental proteins in a sample, such as in accord with any of the provided methods. In some embodiments, the instructions are provided as a label or a package insert, which is on or associated with the container. In some embodiments, the instructions may indicate directions for reconstitution and/or use of the composition.

In some embodiments, the kit or article of manufacture is suitable for use or is for use with a device (also called an instrument) for detecting the bound antibodies in accord with the provided methods. In some embodiments, the device is one that can be used in association with the provided antibodies and reagents to permit protein detection using one or more techniques well known in the art such as, but not limited to, spectrophotometry, high performance liquid chromatography (HPLC), immunoassays such as enzyme-linked immunosorbent assay (ELISA), western blot, automated imaging, immunohistochemistry, flow cytometry, high-throughput screening of an array such as a microarray or nanoarray and surface plasmon resonance. In some embodiments, the device comprises a system for reading an assay output, such as comprises an automated cellular imaging system (ACIS), fluorometer, luminometer, or spectrophotometer for assay detection. In some embodiments, the kit or article of manufacture includes the device.

In some embodiments, the device comprises a solid support such as a solid support described herein. In some embodiments, a solid support may be or comprise a bead, column, an array, a microwell, an assay plate, a cartridge, a stick, a filter, or a strip. In some embodiments, the solid support is inserted into the device, attached to the device and/or held by the device, for example, when the device is operating for detection of one or more protein biomarkers (e.g. placental protein biomarker(s)) in a sample. In some embodiments, the solid support, e.g. one or more microwells, may contain at least an immobilized binding agent, for example a capture reagent, such as an antibody, e.g. a first antibody as described herein for capturing the protein. In some embodiments, the solid support is configured in the device to receive a sample loaded into the device. In some embodiments, the sample is added to the solid support prior to its insertion or attachment of the solid support with or into the device. In some embodiments, the device is further configured to add solution from a dispenser into the solid support and/or remove solution from the solid support. In some embodiments, the solution is or comprises a binding agent, for example a detection reagent, such as an antibody, e.g. a second antibody as described herein for detecting the protein. In some embodiments, the solution is or comprises a wash solution. In some embodiments, the solution is or comprises a substrate or stop solution. In some embodiments, the device is configured to hold one or more of the above solutions and to individually dispense each solution at an appropriate time into the solid support held or inserted in the device.

In some embodiments, the device automates or partially automates an assay method that detects a particular biomarker or biomarkers, such as placental protein biomarkers as described. In some embodiments, actions that may be automated by the instrument include, but are not limited to, mixing or agitation of a sample during an incubation phase, dispensing or adding one or more solutions, washing of a sample, controlling incubation times, optical illumination and/or reading of an assay, and calculation of a biomarker amount in the sample. In some embodiments, the timing of any of the above automated steps can be preset or predetermined, such as to assay specific guidelines.

In some embodiments, the device is a portable device such as a handheld device. In some embodiments, the device is a stationary device. In some embodiments, the device may be the size of a desktop printer, or smaller, and may be suitable for use in a physician's office, hospital lab, or residential dwelling. The device may be manually operated or automatically operated. In some embodiments, the device is an electronic device.

In some embodiments, the device comprises a computing system or processor. In some embodiments, the computing system comprises one or more computer executable logic (e.g., one or more computer program) that is recorded on a computer readable medium. For example, the computing system or processor is configured to execute some or all of the following functions: (i) processing a signal representative of the detected protein, (ii) comparing data as detected from the sample with a reference standard (iii) calculating an amount or concentration of the protein biomarker in the sample; and/or (iv) displaying or outputting a value representative of the calculated amount or concentration of the protein. The computing system can be configured to perform any one of the methods described herein.

The computer executable logic can work in any computer that may be any of a variety of types of general-purpose computers such as a personal computer, network server, workstation, handheld device or other computer platform now or later developed. In some embodiments, a computing system is described comprising a computer usable medium having the computer executable logic (computer software program, including program code) stored therein. The computer executable logic can be executed by a processor, causing the processor to perform functions described herein. In other embodiments, some functions are implemented primarily in hardware using, for example, a hardware state machine. Implementation of the hardware state machine so as to perform the functions described herein will be apparent to those skilled in the relevant arts.

IV. EXEMPLARY EMBODIMENTS

Among the provided embodiments are:
1. A method for classifying the gestational age (GA) of a pregnancy, the method comprising:
  (a) measuring the concentration of a placental protein from a sample from a pregnant subject, wherein the placental protein is selected from ADAM-12, PAPP-A, PSG1, and HPL;

(b) comparing the concentration to a predetermined threshold level for the placental protein; and (c) determining if the gestational age of the pregnancy is greater than or equal to a predetermined GA cutpoint, wherein the predetermined GA cutpoint is a timepoint between at or about 5 weeks and at or about 40 weeks, thereby classifying the gestational age as predicted to be greater than or equal to the predetermined GA cutpoint or less than the predetermined GA cutpoint.

2. The method of embodiment 1, wherein the measuring is carried out by an immunoassay.

3. The method of embodiment 2, wherein the immunoassay is a solid-phase immunoassay.

4. The method of embodiment 2 or embodiment 3, wherein the immunoassay is an Enzyme linked immunosorbent assay (ELISA).

5. The method of any of embodiments 2-4, wherein the immunoassay is a sandwich ELISA.

6. The method of any of embodiments 1-5, wherein the method further comprises selecting the subject as a candidate for a prenatal care or a clinical treatment if the gestational age is predicted to be less than the predetermined GA cutpoint.

7. The method of any of embodiments 1-6, wherein the placental protein is ADAM-12.

8. The method of any of embodiments 1-6, wherein the placental protein is PAPP-A.

9. The method of any of embodiments 1-6, wherein the placental protein is PSG1.

10. The method of any of embodiments 1-6, wherein the placental protein is HPL.

11. The method of embodiments 1-10, wherein steps (a)-(c) are repeated for each of one or more further placental protein for the same predetermined GA cutpoint.

12. The method of embodiment 11, wherein each of the one or more further placental protein is another one or more placental protein selected from among ADAM-12, PAPP-A, PSG1 and HPL.

13. The method of embodiment 11 or embodiment 12, wherein the one or more further placental protein is 1 further placental protein or 2 further placental proteins.

14. The method of any of embodiments 11-13, wherein the placental protein and the one or more further placental protein are ADAM-12/PAPP-A, ADAM-12/PSG1, ADAM-12/HPL, PAPP-A/PSG1, PAPP-A/HPL, PSG1/HPL, ADAM-12/PAPP-A/PSG1, ADAM-12/PAPP-A/HPL, ADAM-12/PSG1/HPL, PAPP-A/PSG1/HPL.

15. The method of any of embodiments 11-14, wherein the method further comprises selecting the subject as a candidate for a prenatal care or a clinical treatment if the gestational age is predicted to be less than the predetermined GA cutpoint for the placental protein and for each of the one or more further placental protein.

16. The method of any of embodiments 1-15, wherein the predetermined GA cutpoint is a timepoint between at or about 5 weeks and at or about 20 weeks, inclusive.

17. The method of any of embodiments 1-16, wherein the placental protein (or the one or more placental protein) is PAPP-A and the predetermined threshold level of PAPP-A is a value between 3 ng/mL and 130 ng/mL, inclusive.

18. The method of any of embodiments 1-16, wherein the placental protein (or the one or more placental protein) is ADAM-12 and the predetermined threshold level of ADAM-12 is a value between at or about 0.5 ng/mL and at or about 15 ng/mL, inclusive.

19. The method of any of embodiments 1-16, wherein the placental protein (or the one or more placental protein) is PSG1 and the predetermined threshold level of PSG1 is a value between at or and the predetermined threshold level is a value between at or about 5 ng/mL and at or about 4000 ng/mL, optionally a value between at or about 10 ng/mL and at or about 25 ng/mL or a value between at or about 3000 ng/mL and at or about 4000 ng/mL.

20. The method of any of embodiments 1-16, wherein the placental protein (or the one or more placental protein) is HPL and the predetermined threshold level of HPL is a value between at or 0.02 mg/L and at or about 4 mg/L, inclusive.

21. The method of any of embodiments 1-20, wherein the predetermined GA cutpoint is a timepoint between 64 days and at or about 140 days, inclusive, optionally wherein the GA cutpoint is or is about 70 days.

22. The method of any of embodiments 1-21, wherein:
the placental protein is PAPP-A and the predetermined threshold level is a value between at or about 3 ng/mL and at or about 10 ng/mL, optionally a value between at or about 5 ng/mL and 6 ng/mL;
the placental protein is ADAM-12 and the predetermined threshold level is a value between at or about 0.5 ng/mL and at or about 4 ng/mL, optionally a value between at or about 2 ng/mL and at or about 3 ng/mL;
the placental protein is PSG1 and the predetermined threshold level is a value between at or about 5 ng/mL and at or about 500 ng/mL;
the placental protein is HPL and the predetermined threshold level is a value between at or about 0.02 mg/L and at or about 0.1 mg/L, optionally a value of at or about 0.03 mg/L.

23. The method of any of embodiments 1-21, wherein the predetermined GA cutpoint is a timepoint between 80 days and at or about 140 days, inclusive.

24. The method of any of embodiments 1-21 and 22, wherein the GA cutpoint is or is about 104 days.

25. The method of any of embodiments 1-21, 23 and 24, wherein:
the placental protein is PAPP-A and the predetermined threshold level is a value between at or about 10 ng/mL and at or about 70 ng/mL, optionally a value between at or about 40 ng/mL and 50 ng/mL;
the placental protein is ADAM-12 and the predetermined threshold level is a value between at or about 3.5 ng/mL and at or about 8 ng/mL, optionally a value between at or about 4 ng/mL and at or about 5 ng/mL;
the placental protein is PSG1 and the predetermined threshold level is a value between at or about 2000 ng/mL and at or about 5000 ng/mL, optionally a value between at or about 3000 ng/mL and at or about 4000 ng/mL;
the placental protein is HPL and the predetermined threshold level is a value between at or about 0.1 mg/L and at or about 1 mg/L, optionally a value between at or about 0.09 mg/L and at or about 1 mg/L.

26. The method of any of embodiments 1-21 and 23, wherein the GA cutpoint is or is about 140 days.

27. The method of any of embodiments 1-21, 23 and 26, wherein:
the placental protein is PAPP-A and the predetermined threshold level is a value between at or about 60 ng/mL and at or about 130 ng/mL, optionally a value between at or about 70 ng/mL and 80 ng/mL;
the placental protein is ADAM-12 and the predetermined threshold level is a value between at or about 8 ng/mL and at or about 14 ng/mL, optionally a value between at or about 9 ng/mL and at or about 10 ng/mL;

the placental protein is PSG1 and the predetermined threshold level is a value between at or about 2000 ng/mL and at or about 5000 ng/mL, optionally a value between at or about 3000 ng/mL and at or about 4000 ng/mL;

the placental protein is HPL and the predetermined threshold level is a value between at or about 1 mg/L and at or about 3 mg/L, optionally a value between at or about 1 mg/L and at or about 2 mg/L.

28. The method of any of embodiments 1-27, wherein the sample is a whole blood or serum sample.

29. The method of any of embodiments 1-28, wherein the method is carried out using a point-of-care device.

30. The method of any of embodiments 1-28, wherein the method is carried out in a laboratory.

31. The method of any of embodiments 1-30, wherein the method is carried out without an ultrasound.

32. The method of any of embodiments 1-30, wherein the method further comprises performing an ultrasound.

33. A method for screening a subject for a prenatal care or clinical treatment, the method comprising:
(a) classifying the gestational age (GA) of a pregnancy according to the method of any of embodiments 1-32; and
(b) based on the classifying, (i) selecting a subject as eligible for a prenatal care or clinical treatment if the classified gestational age is less than the predetermined GA cutpoint; or (ii) selecting a subject as not eligible from a prenatal care or clinical treatment and/or as a candidate for further assessment for a prenatal care or clinical treatment if the classified gestational age is greater than or equal to the predetermined GA cutpoint.

34. The method of embodiment 33, wherein if a subject of (i) is selected, performing a prenatal care or clinical treatment on the subject.

35. The method of embodiment 33, wherein if a subject of (ii) is selected, further administering a medical assessment of the subject to determine the gestational age, optionally wherein the medical assessment is or comprises an ultrasound.

36. A method for performing a prenatal care or clinical treatment on a subject, the method comprising performing a prenatal care of clinical treatment of a subject selected as eligible for the prenatal care or clinical treatment according to the method of embodiment 33 or embodiment 34.

37. The method of embodiment 6, embodiment 15, embodiment 33, embodiment 34 or embodiment 36 wherein the prenatal care or clinical treatment is a medical abortion or early aspiration, optionally wherein the GA cutpoint is at or about 10 weeks.

38. The method of embodiment 6, embodiment 15, embodiment 33, embodiment 34, or embodiment 36 wherein the prenatal care or clinical treatment is a test for a chromosomal abnormality or a test that involves amniocentesis, optionally wherein the GA cutpoint is a timepoint between at or about 15 weeks and 18 weeks, inclusive, optionally at or about 104 days.

39. The method of embodiment 6, embodiment 15, embodiment 33, embodiment 34 or embodiment 36 wherein the prenatal care or clinical treatment is a glucose tolerance test, optionally wherein the GA cutpoint is a timepoint at or greater than 20 weeks, optionally between at or about 26 and at or about 28 weeks, inclusive, optionally at or about 140 days.

40. The method of embodiment 6, embodiment 15, embodiment 33 or embodiment 34 or embodiment 36, wherein the prenatal care or clinical treatment is a decision about the risk of embryotoxicity, optionally wherein the GA cutpoint is a timepoint between at or about 8 weeks and at or about 10 weeks, inclusive, optionally wherein the GA cutpoint is at or about 10 weeks.

41. A device for carrying out the methods of any of embodiments 1-40.

42. The device of embodiment 41 that is hand-held device or point-of-care device.

43. A method for performing a prenatal care or prenatal clinical treatment on a pregnant subject, the method comprising:
(a) measuring the concentration of a placental protein from a sample from a pregnant subject, wherein the placental protein is selected from ADAM-12, PAPP-A, PSG1, and HPL;
(b) predicting the gestational age of the pregnancy based on the concentration, wherein the predicting comprises providing the concentration as input to a process that uses concentration of the placental protein as a continuous predictor of gestational age;
(c) selecting a prenatal care or prenatal clinical treatment for the pregnant subject based on the gestational age of the pregnancy; and
(d) performing the prenatal care or prenatal clinical treatment on the pregnant subject.

44. The method of embodiment 43, wherein the measuring is carried out by an immunoassay.

45. The method of embodiment 44 or embodiment 45, wherein steps (a)-(b) are repeated for each of one or more further placental protein.

46. The method of embodiment 46, wherein the prenatal care or prenatal clinical treatment is selected based on the predicted gestational ages for the placental protein and the one or more further placental protein.

47. A method for performing a prenatal care or prenatal clinical treatment on a pregnant subject, the method comprising performing on a pregnant subject a prenatal care or prenatal clinical treatment selected for the pregnant subject based on the gestational age of the pregnancy, wherein the gestational age of the pregnancy is predicted based on a measured concentration of a placental protein from a sample from the pregnant subject, wherein:
the predicting comprises providing the concentration as input to a process that uses concentration of the placental protein as a continuous predictor of gestational age; and
the placental protein is selected from ADAM-12, PAPP-A, PSG1, and HPL.

48. The method of embodiment 48, wherein the concentration is measured by an immunoassay.

49. The method of embodiment 48 or embodiment 49, wherein gestational age is predicted using each of one or more further placental protein.

50. The method of embodiment 50, wherein the prenatal care or prenatal clinical treatment is selected based on the predicted gestational ages for the placental protein and the one or more further placental protein.

51. The method of any of embodiments 44-51, wherein the process comprises a regression model trained using gestational ages and concentrations of the placental protein from a plurality of pregnant subjects.

52. The method of any of embodiments 44, 45, 48, and 49, wherein the process comprises a regression model that is a multiple regression model, and the multiple regression model is trained using gestational ages, concentrations of the placental protein, and concentrations of each of one or more further placental protein.

53. The method of embodiment 52 or embodiment 53, wherein the regression model is a linear regression model, a piecewise linear model, a polynomial regression model, or a Bayesian model.

54. The method of any of embodiments 45-47 and 49-54, wherein the immunoassay is a solid-phase immunoassay.

55. The method of any of embodiments 45-47 and 49-55, wherein the immunoassay is an Enzyme linked immunosorbent assay (ELISA).

56. The method of any of embodiments 45-47 and 49-56, wherein the immunoassay is a sandwich ELISA.

57. The method of any of embodiments 44-57, wherein the placental protein is ADAM-12.

58. The method of any of embodiments 44-57, wherein the placental protein is PAPP-A.

59. The method of any of embodiments 44-57, wherein the placental protein is PSG1.

60. The method of any of embodiments 44-57, wherein the placental protein is HPL.

61. The method of any of embodiments 46, 47, and 50-61, wherein each of the one or more further placental protein is another placental protein selected from among ADAM-12, PAPP-A, PSG1 and HPL.

62. The method of any of embodiments 46, 47, and 50-62, wherein the one or more further placental protein is 1 further placental protein or 2 further placental proteins.

63. The method of any of embodiments 46, 47, and 50-63, wherein the placental protein and the one or more further placental protein are ADAM-12/PAPP-A, ADAM-12/PSG1, ADAM-12/HPL, PAPP-A/PSG1, PAPP-1/HPL, PSG1/HPL, ADAM-12/PAPP-A/PSG1, ADAM-12/PAPP-A/HPL, ADAM-12/PSG1/HPL, or PAPP-A/PSG1/HPL.

64. The method of any of embodiments 44-64, wherein the sample is a whole blood or serum sample.

65. The method of any of embodiments 44-65, wherein the method is carried out using a point-of-care device.

66. The method of any of embodiments 44-65, wherein the method is carried out in a laboratory.

67. The method of any of embodiments 44-67, wherein the method is carried out without an ultrasound.

68. The method of any of embodiments 44-67, wherein the method further comprises performing an ultrasound.

69. The method of any of embodiments 44-69, wherein the prenatal care or prenatal clinical treatment is selected from a medical abortion or early aspiration; a test for a chromosomal abnormality or a test that involves amniocentesis; a glucose tolerance test; a decision about the risk of embryotoxicity; a clinical examination; a vaccination; a risk assessment; a fetal assessment; a blood assay; a urine assay; vitamin supplementation; a test for disease; education; counseling; and any combination of any of the foregoing.

70. The method of any of embodiments 44-70, wherein the prenatal care or prenatal clinical treatment is a medical abortion or early aspiration.

71. The method of any of embodiments 44-70, wherein the prenatal care or prenatal clinical treatment is a test for a chromosomal abnormality or a test that involves amniocentesis.

72. The method of any of embodiments 44-70, wherein the prenatal care or prenatal clinical treatment is a glucose tolerance test.

73. The method of any of embodiments 44-70, wherein the prenatal care or prenatal clinical treatment is a decision about the risk of embryotoxicity.

74. A device for carrying out the method of any of embodiments 44-74.

75. The device of embodiment 75 that is a hand-held device or a point-of-care device.

V. EXAMPLES

The following examples are included for illustrative purposes only and are not intended to limit the scope of the invention.

Example 1: Assessment of Placental Proteins Across Gestational Age Ranges

A study was conducted that included 245 female subjects with pregnancies within various Gestational Age (GA) ranges. Subjects were selected based on the following inclusion criteria: confirmed intrauterine pregnancy by ultrasound; no evidence of maternal or fetal conditions (pregnancy-induced hypertension (pre-eclampsia) or diabetes; not known to have a non-viable pregnancy, multiple pregnancy, a pregnancy with a fetal, chromosomal or other abnormality, or a pregnancy with a fetal growth restriction; not currently having substantial maternal bleeding such as vaginal bleeding, or other unusual pelvic pain or other symptom that may indicate a pregnancy complication; no anticoagulant use; and no use of assisted reproductive technology in current pregnancy. Subjects ranged in weight from 43-150 kilograms (median 66 kilograms) and had body mass indices ranging from 17 to 52 $kg/m^2$ (median 24 $kg/m^2$). Additional characteristics are outlined in Table 1.

TABLE 1

| Characteristics of Enrolled Subjects | | |
|---|---|---|
| | N | (%) |
| Age (years) | | |
| ≤24 | 80 | 33% |
| 25-29 | 65 | 27% |
| 30-34 | 66 | 27% |
| ≥35 | 34 | 14% |
| Race | | |
| Hispanic | 7 | 3% |
| White | 87 | 36% |
| Black | 116 | 47% |
| Asian | 12 | 5% |
| Other | 10 | 4% |
| Multiple | 13 | 5% |
| Maternal conditions | | |
| Current tobacco use | 25 | 10% |
| Alcohol use in this pregnancy | 33 | 13% |
| Used medications in the past week | 98 | 40% |
| Medical conditions | 89 | 36% |

GA was determined from reported findings from the earliest ultrasound present in the patient's medical chart. Enrollment quotas were established to ensure representation across the GA spectrum, with oversampling of patients between 5 and 15 weeks (105 days) of gestation. Table 2 outlines the distribution of subjects across the GA spectrum for this group of assessed subjects.

TABLE 2

Gestational age at sample collection (days)

| Gestational age | Number of subjects | Percent of subjects |
|---|---|---|
| 34-41 | 21 | 9% |
| 42-48 | 20 | 8% |
| 49-55 | 20 | 8% |
| 56-62 | 20 | 8% |
| 63-69 | 21 | 9% |
| 70-76 | 20 | 8% |
| 77-83 | 20 | 8% |
| 84-90 | 21 | 9% |
| 91-97 | 21 | 9% |
| 98-104 | 21 | 9% |
| 105-139 | 10 | 4% |
| 140-174 | 10 | 4% |
| 175-209 | 10 | 4% |
| 210-273 | 10 | 4% |

Serum specimens were obtained from all 245 women enrolled in the study. Blood was drawn from a vein into a non-heparinized tube, allowed to clot and then centrifuged. All specimens were refrigerated and then frozen to −80° C. on the day of collection. The amount of several placental proteins, including HPL, PSG-1, PAPP-A, and ADAM-12, were analyzed by immunoassay from the collected blood samples. Illustrative immunoassay kits and reagents used in performing the analysis included Human ADAM-12 Quantikine ELISA (R&D Systems, catalog #DAD120), Human Pappalysin-1/PAPP-A Quantikine ELISA (R&D Systems, catalog #DPPA00), Human PSG1 Quantikine ELISA (R&D Systems, catalog #DPSG10), Human Placental Lactogen (HPL) ELISA (ALPCO Diagnostics, Catalog #20-HPLHU-E01). All assay runs included proper controls and all the controls were within the appropriate range. At this time point in the study, PAPP-A, and hPL have been assessed for all 245 subjects, biomarker ADAM-12 has been assessed for 243 subjects, and biomarker PSG1 has been assessed for 242 subjects. PAPP-A and ADAM-12 in urine were also assayed.

For each assessed protein, scatterplots were generated of the serum concentrations plotted by GA as determined by ultrasound. Values below the lower limit of detection of the assay were assigned as ⅔ of the limit.

Figure 3A:
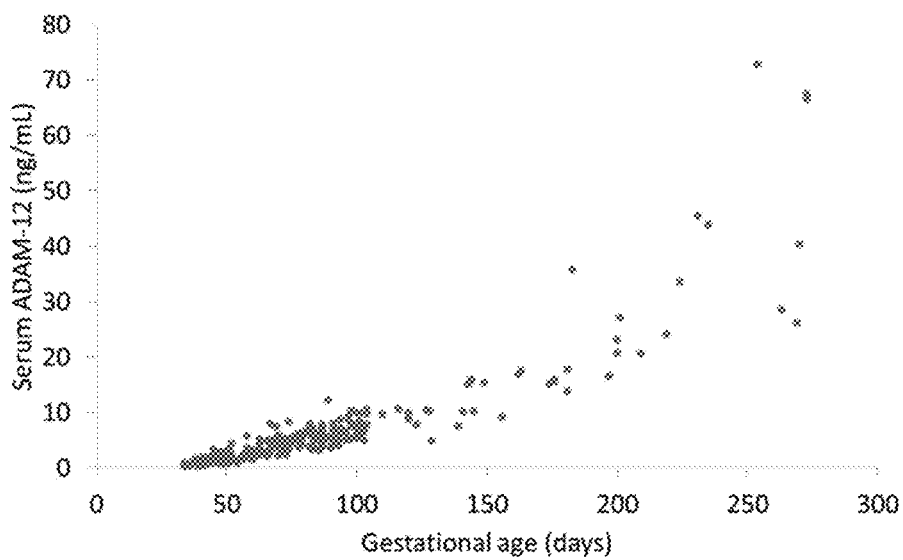
FIGS. 3A and 3B show results for serum concentration of ADAM-12 (ng/mL) plotted by gestational age of pregnancy of female subjects.
Figure 3B:
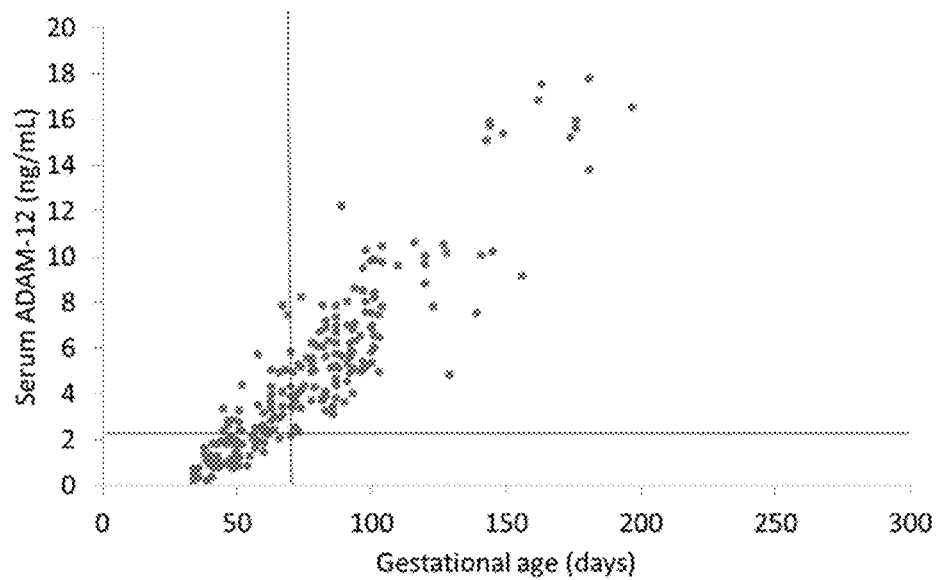
Figure 4A:
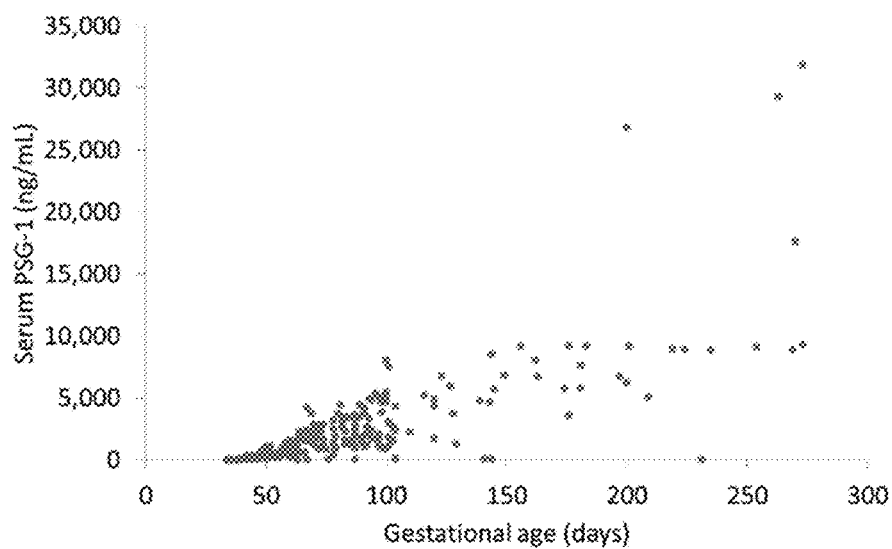
FIGS. 4A and 4B show results for serum concentration of PSG-1 (ng/mL) plotted by gestational age of pregnancy of female subjects.
Figure 4B:
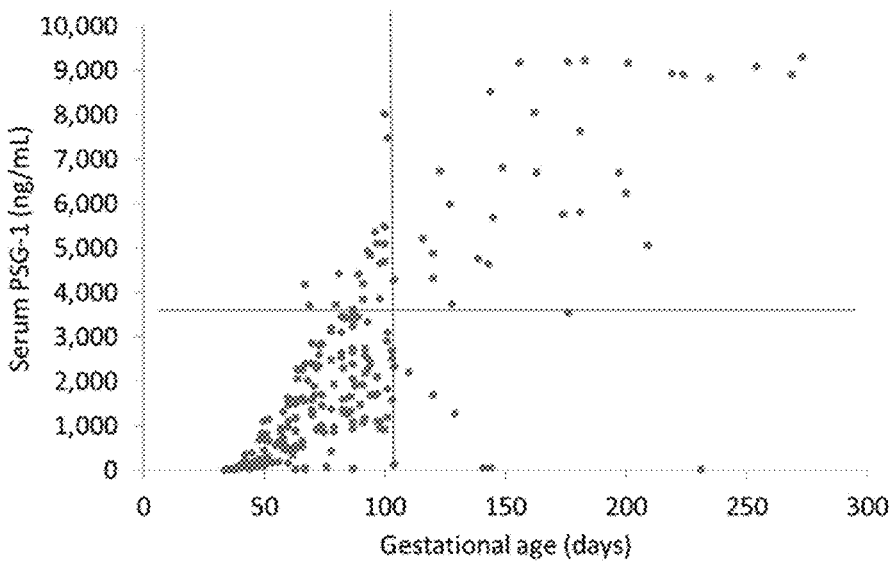
Figure 5A:
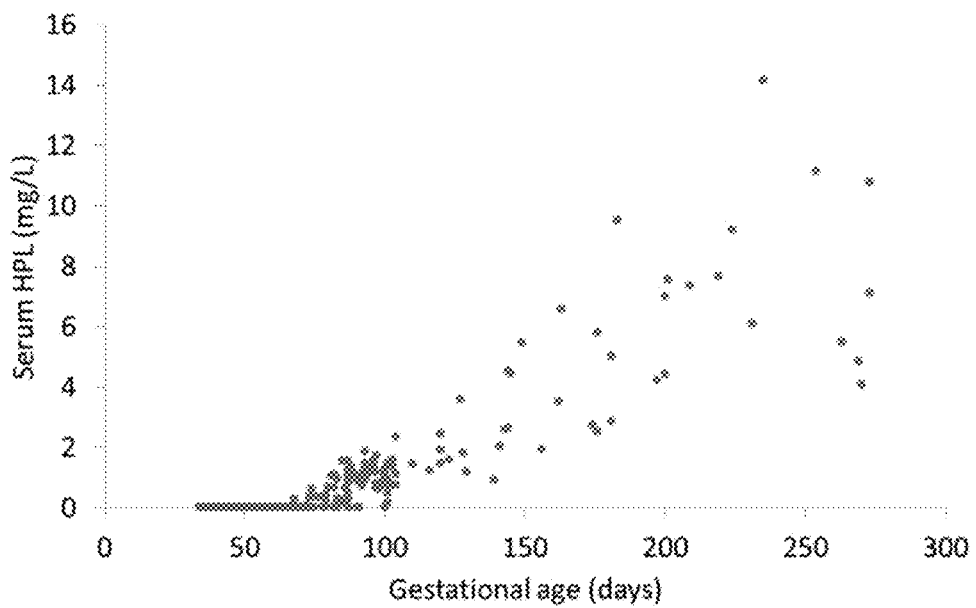
FIGS. 5A and 5B show results for serum concentration of hPL (mg/L) plotted by gestational age of pregnancy of female subjects.
Figure 5B:
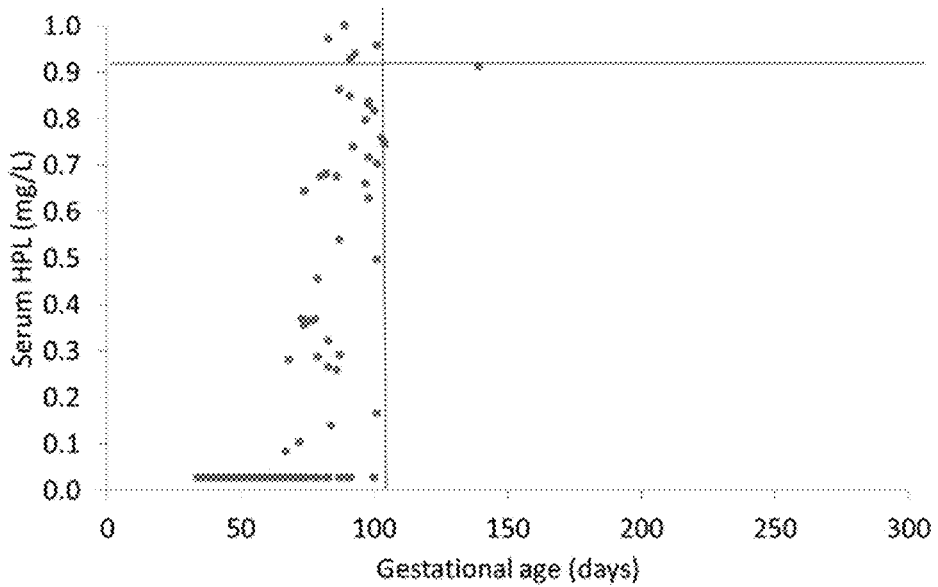

Scatterplots of serum concentration by GA are shown for PAPP-A (FIG. 2A-2E), ADAM-12 (FIGS. 3A and 3B), PSG1 (FIGS. 4A and 4B), and HPL (FIGS. 5A and 5B). In FIGS. 2A, 3A, 4A, and 5A, the serum concentration of each protein is shown across the full spectrum of GA. As shown, concentrations of the assessed placental protein biomarkers increased with GA over some portion of pregnancy.

To establish a protein concentration (threshold level) that may distinguish pregnancies of less than a particular GA cutpoint from pregnancies greater than a particular GA cutpoint, zoomed plots were created around exemplary GA cutpoints for each protein to either maximize specificity or positive predictive value or to maximize sensitivity or negative predictive value. Illustrative zoomed plots are shown for the respective proteins in corresponding FIGS. 2B-2E, 3B, 4B, 5B and 6B; for each zoomed plot a line is drawn marking an exemplary GA cutpoint and threshold level concentration. In the exemplary zoomed plot in FIG. 2B (PAPP-A), an illustrative line at GA cutpoint is shown at 70 days, with a threshold level of 5.6 ng/ml. In the exemplary zoomed plot in FIG. 2C (PAPP-A), an illustrative line at GA cutpoint is shown at 104 days, with a threshold level of 41.053 ng/ml. In the exemplary zoomed plot in FIG. 2D (PAPP-A), an illustrative line at GA cutpoint is shown at 140 days, with a threshold level of 80.256 ng/ml. In the exemplary zoomed plot in FIG. 2E (PAPP-A), an illustrative line at GA cutpoint is shown at 140 days, with a threshold level of 122.752 ng/ml. In the exemplary zoomed plot in FIG. 3B (ADAM-12), an illustrative line at GA cutpoint is shown at GA 70 days, with a threshold levels of 2.3 ng/ml. In the exemplary zoomed plot in FIG. 4B (PSG-1), an illustrative line at GA cutpoint is shown at GA 104 days, with a threshold level of 3537 ng/ml. In the exemplary zoomed plot in FIG. 5B (HPL), an illustrative line at GA cutpoint is shown at GA 104 days, with a threshold level of 0.9 mg/L.

Lines on all zoomed plots are for illustrative purposes only and should not be interpreted as the only combination of concentration (threshold level) and GA cutoffs.

Exemplary threshold levels that maximize sensitivity and negative predictive value were determined for each assessed placental protein biomarker at various GA cutpoints. In a first analysis, separate simple logistic regression models were used to estimate receiver operating characteristic (ROC) curves to evaluate the potential for concentrations of each protein in serum and urine to differentiate pregnancies with GAs more or less than 70 days. Urine values were adjusted for urinary creatinine concentration by dividing the former by the latter to correct for variation in urine diluteness. For each ROC curve, the area under the curve (AUC) was estimated along with 95% confidence intervals. AUCs were compared between proteins using a nonparametric approach; an overall test was conducted by comparing all AUCs, and if this test was significant at the 5% level pairwise comparisons were made, with no adjustment for multiple comparisons. Considering that for medical abortion screening, underestimation of GA was clinically undesirable, maximum concentration of each protein was identified that would predict a GA>70 days with 100% sensitivity (or equivalently, the lowest concentration among specimens obtained at GA>70 days), and the sensitivity and specificity of that threshold was estimated using exact binomial 95% confidence limits. In a secondary, illustrative analysis the same exercise was performed but aiming to predict the exemplary GA>105 days (15 weeks+0 days). In this analysis, specimens obtained at GA>252 days (36 weeks+0 days) were excluded based on the presumption that in clinical practice, use of the test after that point in pregnancy would be unlikely. Similar analyses can be carried out on other exemplary GA cutpoints.

The accuracy of using selected proteins was also assessed by on differences by age, race (black vs white), body mass index, time since last food ingestion, any alcohol use during pregnancy, and current tobacco use; for this analysis, continuous variables at the median value were dichotomized, and separate ROC curves were estimated for each subgroup and chi-squared tests were used to compare AUCs between subgroups. Comparisons between serum and urine concentrations, both as reported and adjusted for urinary creatinine concentration, were also examined. In all analyses, protein concentrations reported as below the lower limit of detection of the assay were reported as ⅔ of the limit. All analyses were conducted using SAS, version 9.4 (SAS Institute, Cary, NC).

Table 3 provides a summary of exemplary threshold levels based on a GA cutpoint of 70 days. Table 4 provides a summary of results based on an exemplary GA cutpoint of 104 days. Table 5 provides a summary of results based on an exemplary GA cutpoint of 104 days.

TABLE 3

Exemplary 70 day GA Cutpoint

| | Total N | Concentration threshold | Women with GA ≤70 days | |
|---|---|---|---|---|
| | | | N | % with serum concentration < cutpoint |
| PAPPA | 245 | 5.591 ng/mL | 108 | 90% |
| ADAM 12 | 243 | 2.33 ng/mL | 107 | 60% |
| PSG 1 | 242 | 10.30 ng/mL | 107 | 5% |
| HPL | 245 | 0.03 mg/L | 108 | 0% |

TABLE 4

Exemplary 104 day GA Cutpoint

| | Total N | Concentration threshold | Women with GA ≤104 days | |
|---|---|---|---|---|
| | | | N | % with serum concentration < cutpoint |
| PAPPA | 245 | 41.053 ng/mL | 205 | 91% |
| ADAM 12 | 243 | 4.82 ng/mL | 203 | 61% |
| PSG 1 | 242 | 10.3 ng/mL | 202 | 3% |
| HPL | 245 | 0.913 mg/L | 205 | 82% |

TABLE 5

Exemplary 140 day GA Cutpoint

| | Total N | Concentration threshold | Women with GA ≤140 days | |
|---|---|---|---|---|
| | | | N | % with serum concentration < cutpoint |
| PAPPA | 245 | 80.256 ng/mL | 215 | 96% |
| ADAM 12 | 243 | 9.135 ng/mL | 213 | 94% |
| PSG 1 | 242 | 10.3 ng/mL | 212 | 2% |
| HPL | 245 | 1.95 mg/L | 215 | 99% |

Notably, the ROC curve AUCs for PAPP-A and ADAM-12 were both >0.95. The AUC for PAPP-A was significantly higher than the AUC for any other protein (all p-values <0.01), and the AUC for ADAM-12 was significantly higher than the AUC for any of the other proteins (all p-values <0.01). For PAPP-A, the maximum concentration that provided 100% sensitivity was 5.591 ng/ml (Table 3); this value also identified 90% of people with GAs<70 days (i.e., it had 90% specificity). For ADAM-12, the perfectly sensitive threshold for identifying GAs>70 days provided a specificity of only 60%; however, reducing that threshold to a concentration that provided a sensitivity of 98.5% (3.11 ng/ml) increased the specificity to 77%. For other proteins, no concentration that provided a sensitivity >95% also provided >70% specificity for a 70 day GA cutpoint. No significant differences by age, race, body mass index, tobacco or alcohol use, or time since last food ingestion were found in area under ROC curves for PAPP-A or ADAM-12.

ROC curves calculated using specimens obtained at GA<252 days indicated that all proteins were able to distinguish GAs>105 days from earlier GAs; areas under the curve were >95%. For PAPP-A, the maximum concentration that provided 100% sensitivity also provided >91% specificity in identifying GAs<105 days.

In this study, the assay did not detect any PAPP-A in urine. The urinary ADAM-12 concentration showed poor ability to distinguish GAs above either the 70 day or 105 day cutpoints, whether or not the concentration was adjusted for creatinine. The correlation between serum and urine ADAM-12 concentrations was 0.13, and between serum and creatinine-adjusted ADAM-12 concentrations, it was 0.46.

Together, the results in this example are consistent with a finding that placental biomarkers PAPP-A, ADAM-12, PSG-1, and/or HPL can be used to differentiate pregnancies of less than a predetermined cutpoint GA from later pregnancies. In particular, PAPP-A and ADAM-12 can reliably be used to distinguish gestational ages above or below a predetermined GA cutpoint, such as an exemplary 70 day GA. The results also indicate that several other proteins can be used to distinguish gestational ages above or below higher GA cutpoints, including and PSG-1.

Figure 6:
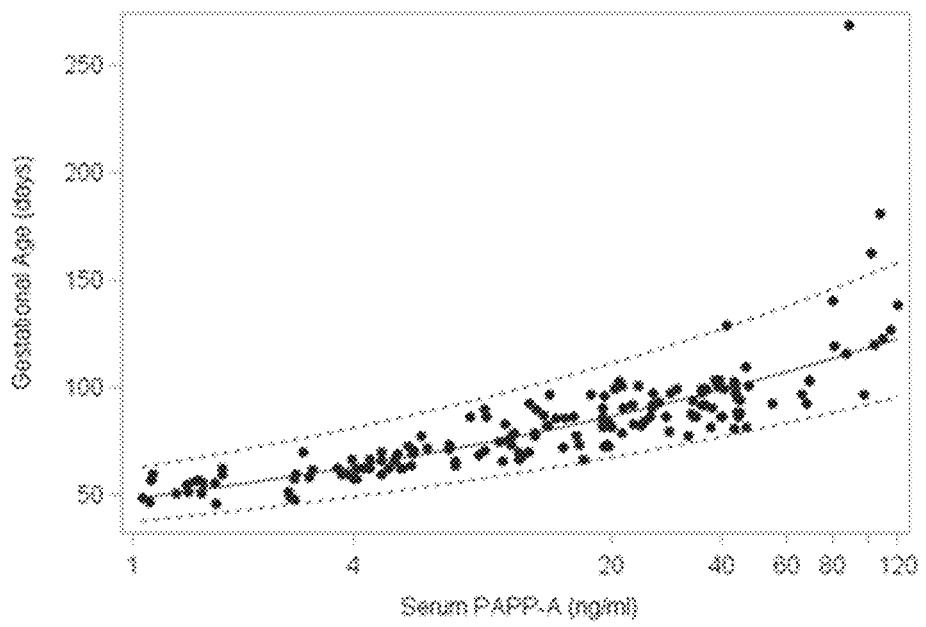
FIG. 6 shows the results of a simple linear regression model that uses serum PAPP-A concentration values to predict gestational age. The dashed lines represent 95% prediction intervals.

Example 2: Serum PAPP-A Concentration as a Continuous Predictor of Gestational Age Using the same data described in Example 1 herein, a simple linear regression model was fit using log-transformed gestational age (GA) as the dependent variable and log-transformed PAPP-A serum concentration values as the independent variable. The model was fit using data points with PAPP-A serum concentration values between one and 120 ng/mL. FIG. 6 shows the back-transformed predicted results of this model as well as dashed lines representing 95% prediction intervals. As shown in FIG. 6, serum PAPP-A concentration values accurately model GA across pregnancy. There were no immediately apparent violations of model assumptions.

These results show that serum PAPP-A concentration values can be used to accurately predict GA in pregnant subjects.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

What is claimed:

1. A method for performing a prenatal care or prenatal clinical treatment on a pregnant subject, wherein the prenatal care or prenatal clinical treatment is a medical abortion or early aspiration, the method comprising:
   (a) measuring the concentration of PAPP-A from a sample from a pregnant subject seeking the medical abortion or early aspiration, wherein:
       the concentration of PAPP-A is measured by an immunoassay; and
       the sample is a whole blood or serum sample;
   (b) determining the gestational age (GA) of the pregnancy as less than 70 days, wherein
       the subject is determined to have a GA of less than 70 days if the measured concentration of PAPP-A is lower than a predetermined threshold level for PAPP-A; and
       the pregnant subject with GA classified as less than 70 days is eligible for a medical abortion or early aspiration; and
   (c) performing the medical abortion or early aspiration on the pregnant subject.

2. The method of claim 1, wherein the predetermined threshold level of PAPP-A is a value between at or about 3 ng/mL and at or about 10 ng/mL, inclusive.

3. The method of claim 1, wherein the medical abortion or early aspiration is a medical abortion, and performing the medical abortion comprises administering mifepristone and misoprostol to the pregnant subject.

4. The method of claim 1, wherein the predetermined threshold level for PAPP-A is determined using GAs and measured concentrations of PAPP-A from a plurality of pregnant subjects.

5. The method of claim 4, wherein the GAs from the plurality of pregnant subjects are determined using ultrasound.

6. The method of claim 4, wherein the plurality of pregnant subjects comprise pregnant subjects with GAs less than 70 days.

7. The method of claim 1, wherein the sample is a whole blood sample.

8. The method of claim 1, wherein the sample is a serum sample.

* * * * *